US009084745B2

(12) United States Patent
Nykjaer et al.

(10) Patent No.: US 9,084,745 B2
(45) Date of Patent: Jul. 21, 2015

(54) MODULATION OF THE VPS10P-DOMAIN FOR THE TREATMENT OF CARDIOVASCULAR DISEASE

(75) Inventors: Anders Nykjaer, Risskov (DK); Mads Fuglsang Kjolby, Arhus (DK)

(73) Assignee: H. Lundback A/S, Valby (DK)

( * ) Notice: Subject to any disclaimer, the term of this patent is extended or adjusted under 35 U.S.C. 154(b) by 762 days.

(21) Appl. No.: 12/993,919

(22) PCT Filed: May 20, 2009

(86) PCT No.: PCT/DK2009/050115
§ 371 (c)(1),
(2), (4) Date: Mar. 7, 2011

(87) PCT Pub. No.: WO2009/140972
PCT Pub. Date: Nov. 26, 2009

(65) Prior Publication Data
US 2011/0166036 A1     Jul. 7, 2011

Related U.S. Application Data

(60) Provisional application No. 61/055,385, filed on May 22, 2008.

(30) Foreign Application Priority Data

May 22, 2008 (DK) .................................. 2008 00711

(51) Int. Cl.
*C40B 30/00* (2006.01)
*A61K 49/00* (2006.01)
(Continued)

(52) U.S. Cl.
CPC ............... *A61K 31/00* (2013.01); *A61K 39/395* (2013.01); *A61K 45/06* (2013.01); *C07K 16/286* (2013.01); *G01N 33/92* (2013.01); *A61K 38/00* (2013.01); *C07K 2316/96* (2013.01); *C07K 2317/77* (2013.01); *G01N 2500/04* (2013.01); *G01N 2500/10* (2013.01); *G01N 2800/32* (2013.01)

(58) Field of Classification Search
CPC ... A61K 38/00; A61K 39/00; A61K 39/3955; A61K 39/39541; C07K 16/00; C07K 16/22; C07K 16/28; C07K 16/2863; C07K 16/2875; G01N 2500/00; G01N 2500/02; G01N 2500/04; G01N 2500/10
See application file for complete search history.

(56) References Cited

FOREIGN PATENT DOCUMENTS

WO    2004056385 A2    7/2004
WO    WO 2004/056385    *    8/2004 ............. A61K 38/00
(Continued)

OTHER PUBLICATIONS

Nykjaer et al., Sortilin is essential for proNGF-induced neuronal cell death, Nature, vol. 427, Feb. 26, 2004.*
(Continued)

*Primary Examiner* — Reza Ghafoorian
(74) *Attorney, Agent, or Firm* — Mary Catherine Di Nunzio

(57) ABSTRACT

The present invention relates to methods for modulating the activity of one or more Vps10p-domain receptors selected from the group consisting of Sortilin, SorLA, SorCS1, SorCS2 and SorCS3, in an animal and methods for preparation of a medicament for the treatment of abnormal plasma lipid concentrations and associated diseases and/or disorders. The modulation is carried out by inhibiting or promoting the binding of ligands to the Vps10p-domain receptor. In vitro and in vivo methods for screening for agents capable of modulation of said Vps10p-domain receptor activity are also provided. The invention furthermore relates to methods of altering expression of said receptors in vivo.

11 Claims, 16 Drawing Sheets

Figure 4:
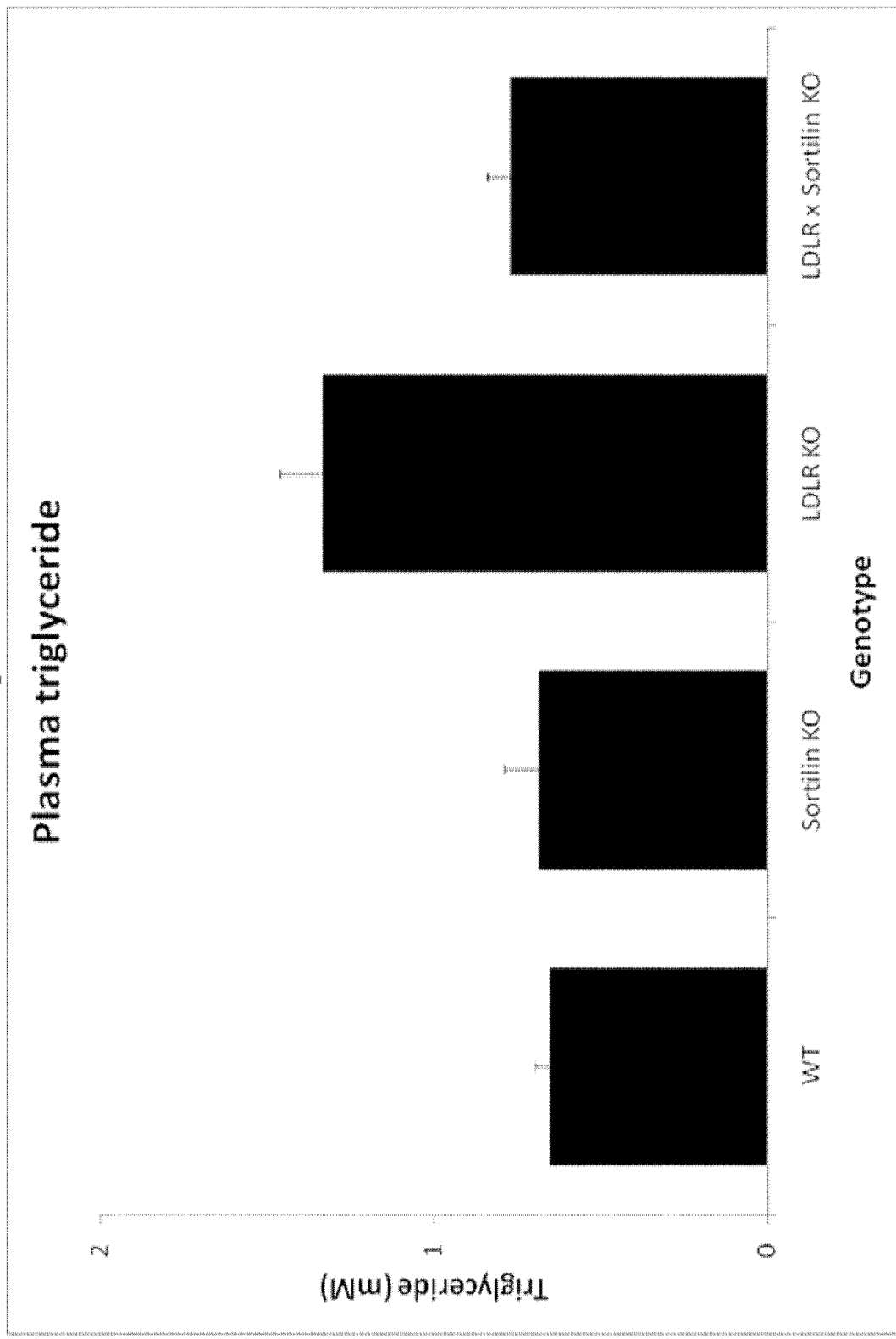

(51) Int. Cl.

| | | |
|---|---|---|
| *A61K 31/00* | (2006.01) | |
| *A61K 39/395* | (2006.01) | |
| *A61K 45/06* | (2006.01) | |
| *C07K 16/28* | (2006.01) | |
| *G01N 33/92* | (2006.01) | |
| *A61K 38/00* | (2006.01) | |

(56) References Cited

FOREIGN PATENT DOCUMENTS

| WO | WO 2005/044293 | * | 5/2005 | ............. A61K 38/00 |
|---|---|---|---|---|
| WO | 2008074329 A2 | | 6/2008 | |

OTHER PUBLICATIONS

Tall et al., Sorting Out Sortilin, Circ Res. 2011;108:158-160.*

Nilsson et al., Endocytosis of Apolipoprotein A-V by Members of the Low Density Lipoprotein Receptor and the Vps10p Domain Receptor Families, The Journal of Biological Chemistry, vol. 274, No. 13, Issue of Mar. 26, pp. 8832-8836, 1999.*

Wu et al., Effect of human apolipoprotein E isoforms on plasma lipids, lipoproteins and apolipoproteins in apolipoprotein E-deficient mice, Atherosclerosis 141 (1998) 287-296.*

Taira et al., LR11, a Mosaic LDL Receptor Family Member, Mediates the Uptake of ApoE-Rich Lipoproteins In Vitro, Arterioscler Thromb Vasc Biol. 2001; 21:1501-1506.*

Dipaola, E.D. And Richelson, E., 1990, Cardiovascular effects of neurotension and some analogues on rats, Eur. J. Pharmacol., 175(3):279-283.

Fiete, a et al., Jan. 19, 2007, N-Linked oligosaccharides on the low density lipoprotein receptor homolog SorLA/ LR11 are modified with terminal GalNac-4-SO4 in kidney and brain, J. Biol. Chem, 282(3):1873-1881.

Jiang, M. et al., 2006, Pitavastatin attenuates the Pdgf-induced LR11/uPA receptor-mediated migration of smooth muscle cells, Biochem. Biophys. Res. Comm., 348(4):1367-1377.

Motoi, Y. et al, 1999, Neuronal localization of a novel mosaic apolipoprotein E receptor, LR11, in rat and human brain, Brain Res., 833(2):209-215.

Munck Petersen, C. et al., 1999, Propeptide cleavage conditions sortilin/neurotensin receptor-3 for ligand binding, Embo J., 18(3):595-604.

Muraki, K. et al, Jun. 30, 1987, Neurotensin receptors on the rat liver plasma membranes, Biochem. Biophys. Res. Comm., 145(3):1071-1079.

Riedel, I.B. et al, 2002, SorLA, a member of the LDL receptor family, is expressed in the collecting duct of the murine kidney, Histochem. Cell. Biol., 118(3):183-191.

Schmidt V. et al, Nov. 9, 2007, SorLA/LR11 regulates processing of amyloid precursor protein via interaction with adaptors GGA and PACS-1, J. Biol. Chem., 282(45):32956-32964.

Yamauchi, R. et al., 2003, Beta-Lactotensin and Neurotensin rapidly reduce serum cholesterol via NT2 receptor, Peptides, 24(12):1955-1961.

Zhu, Y. And Hui, D. Y., 2006, Hypertriglyceridemia in LR11-deficiency mice, The FASEB Journal, 20:A84.

* cited by examiner

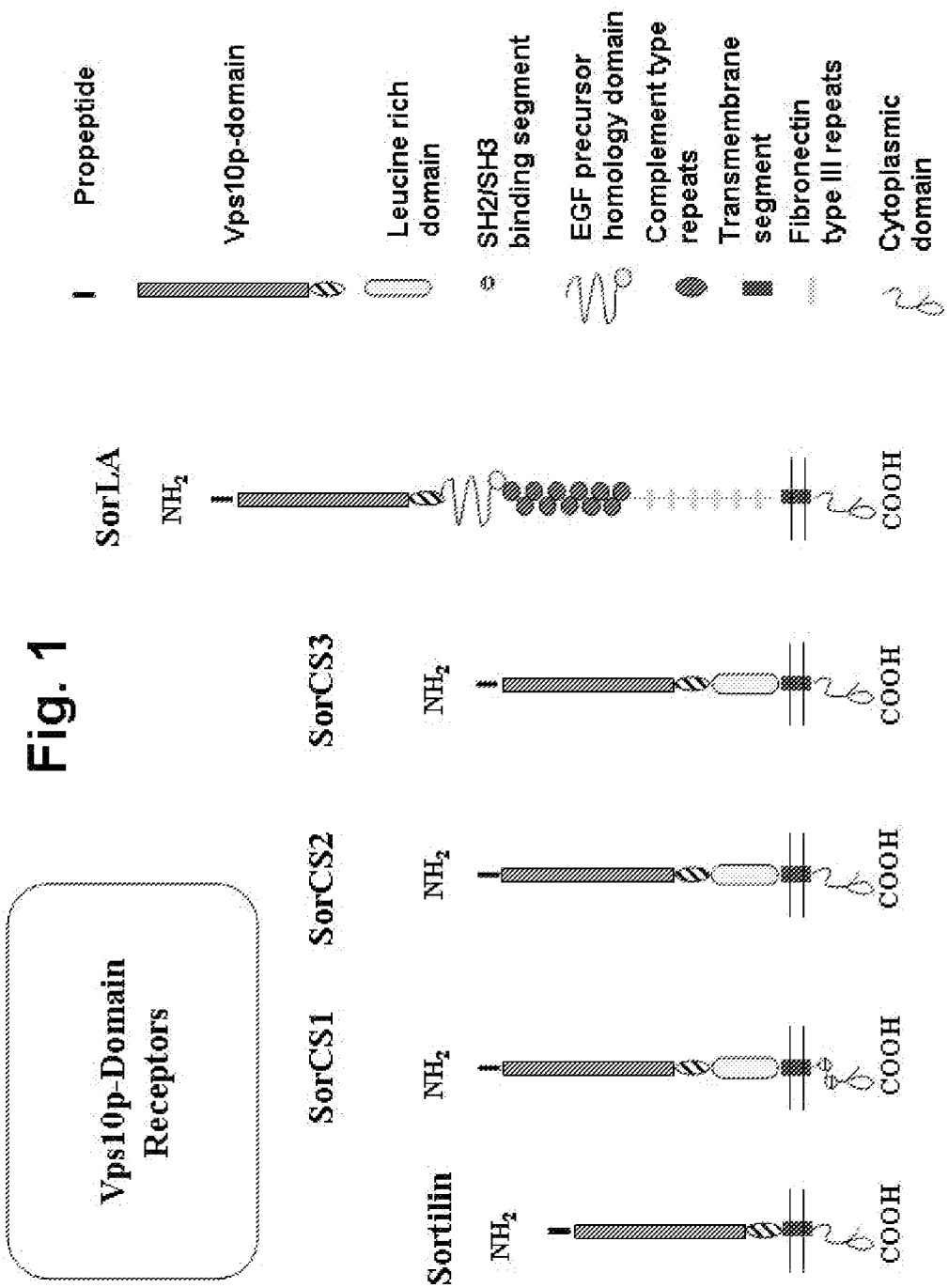

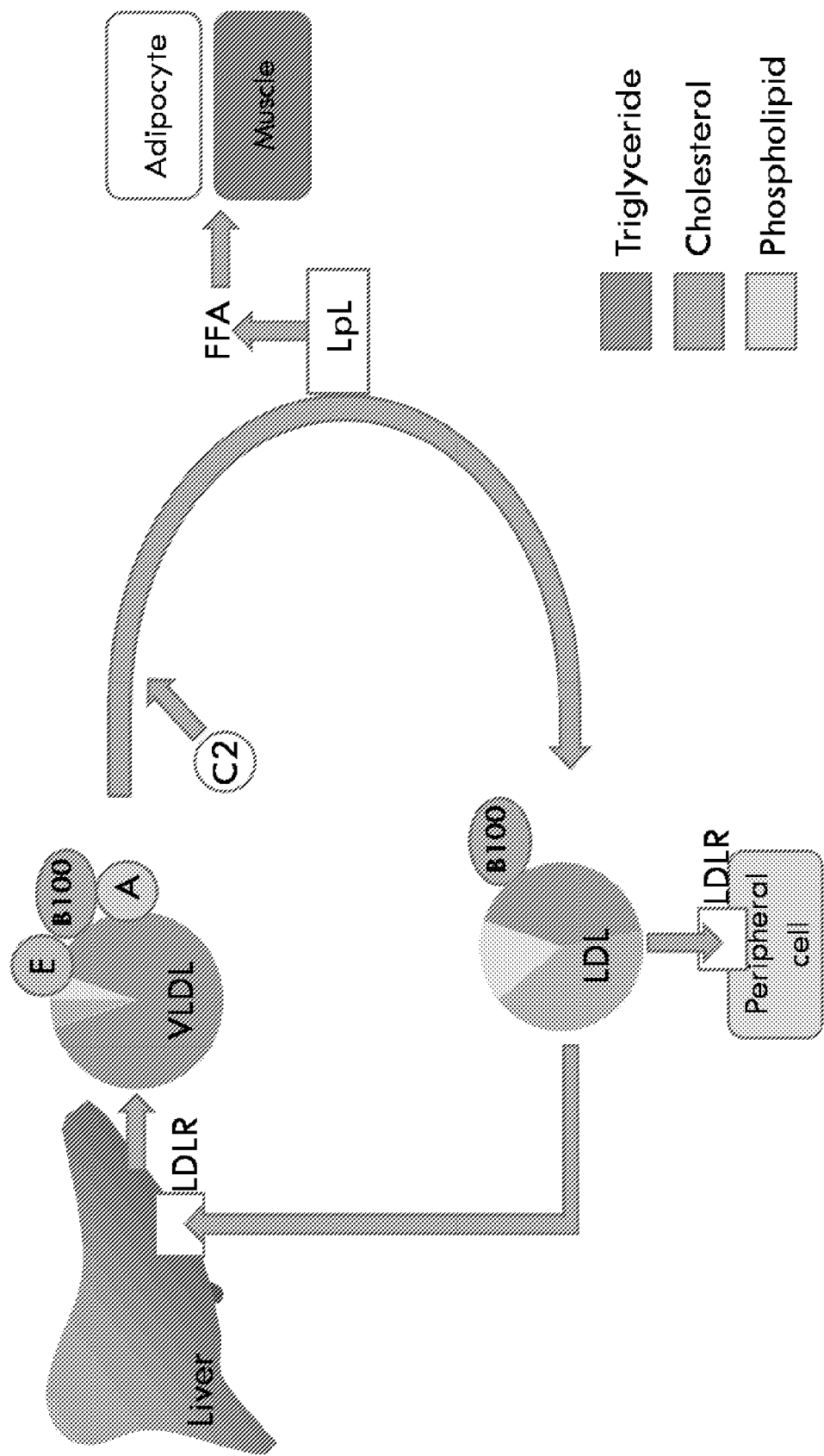

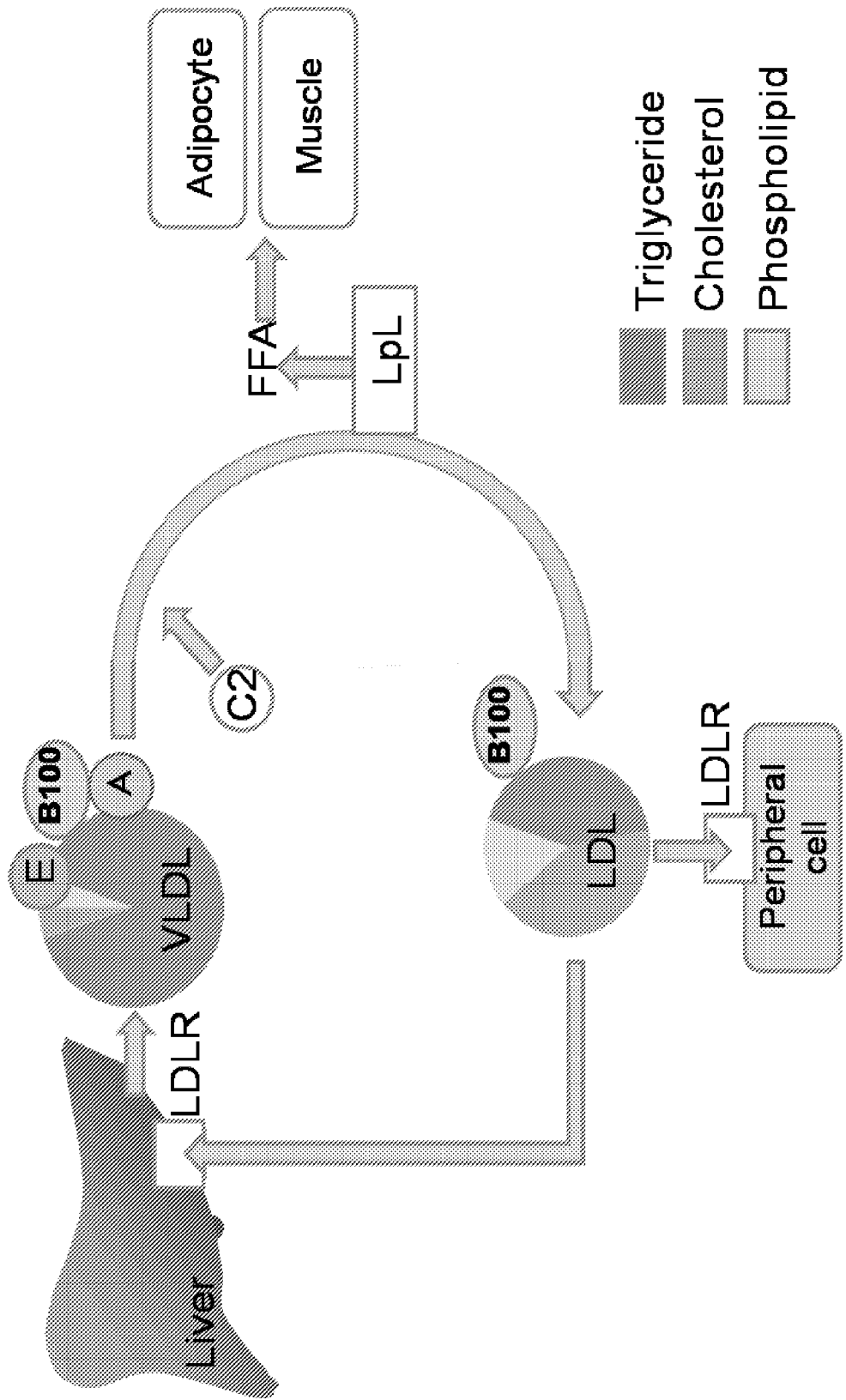

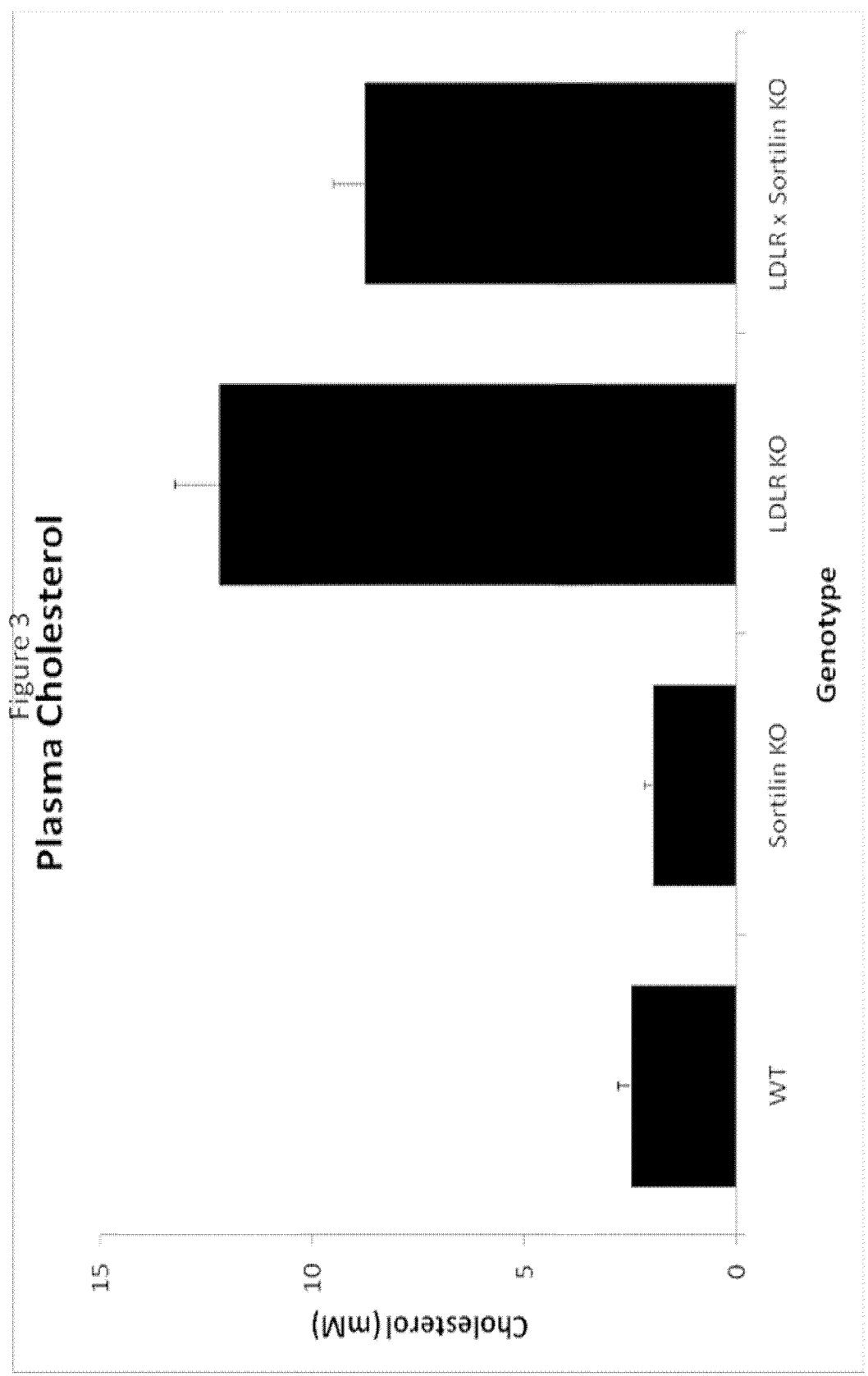

Lipoprotein profile - cholesterol

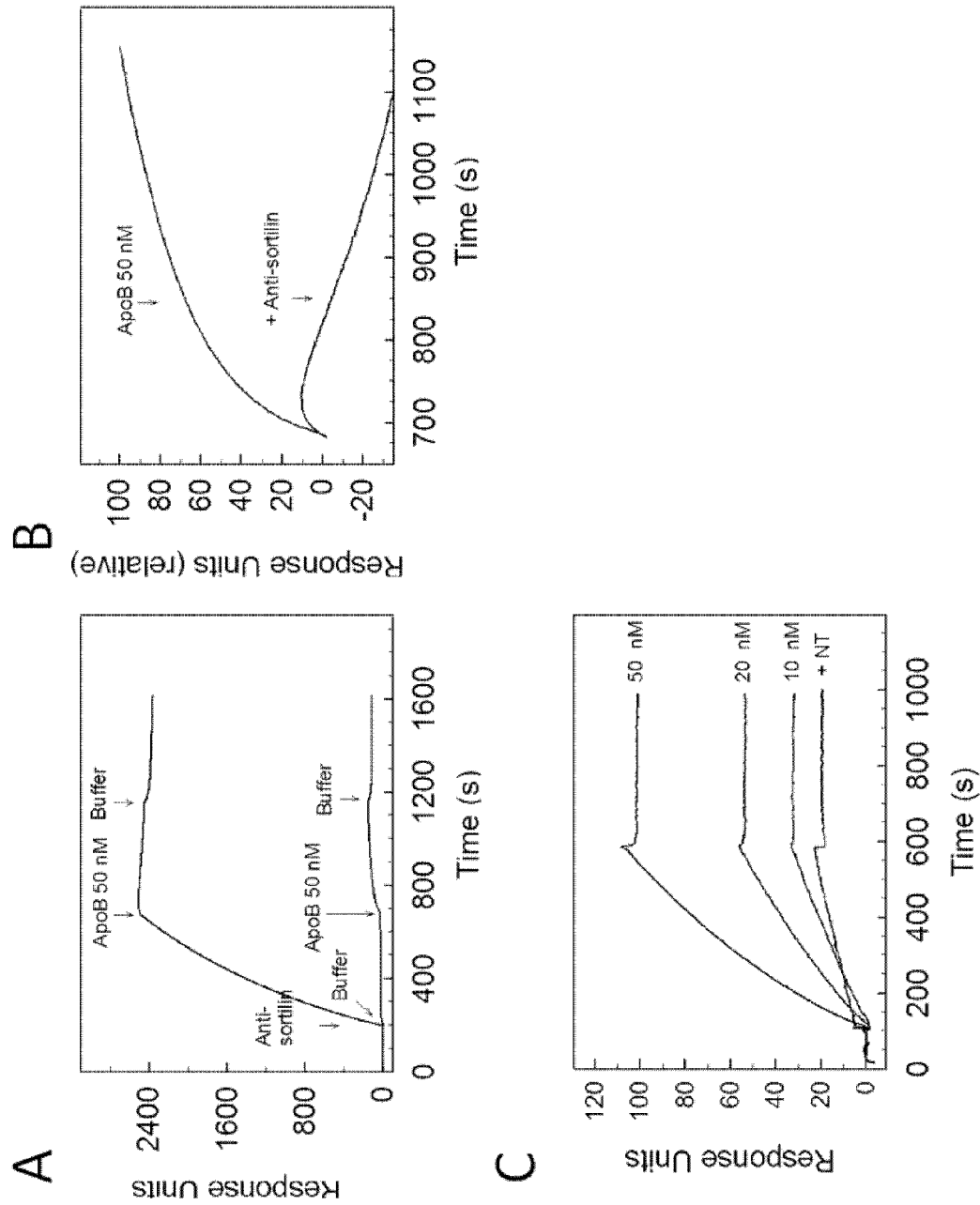

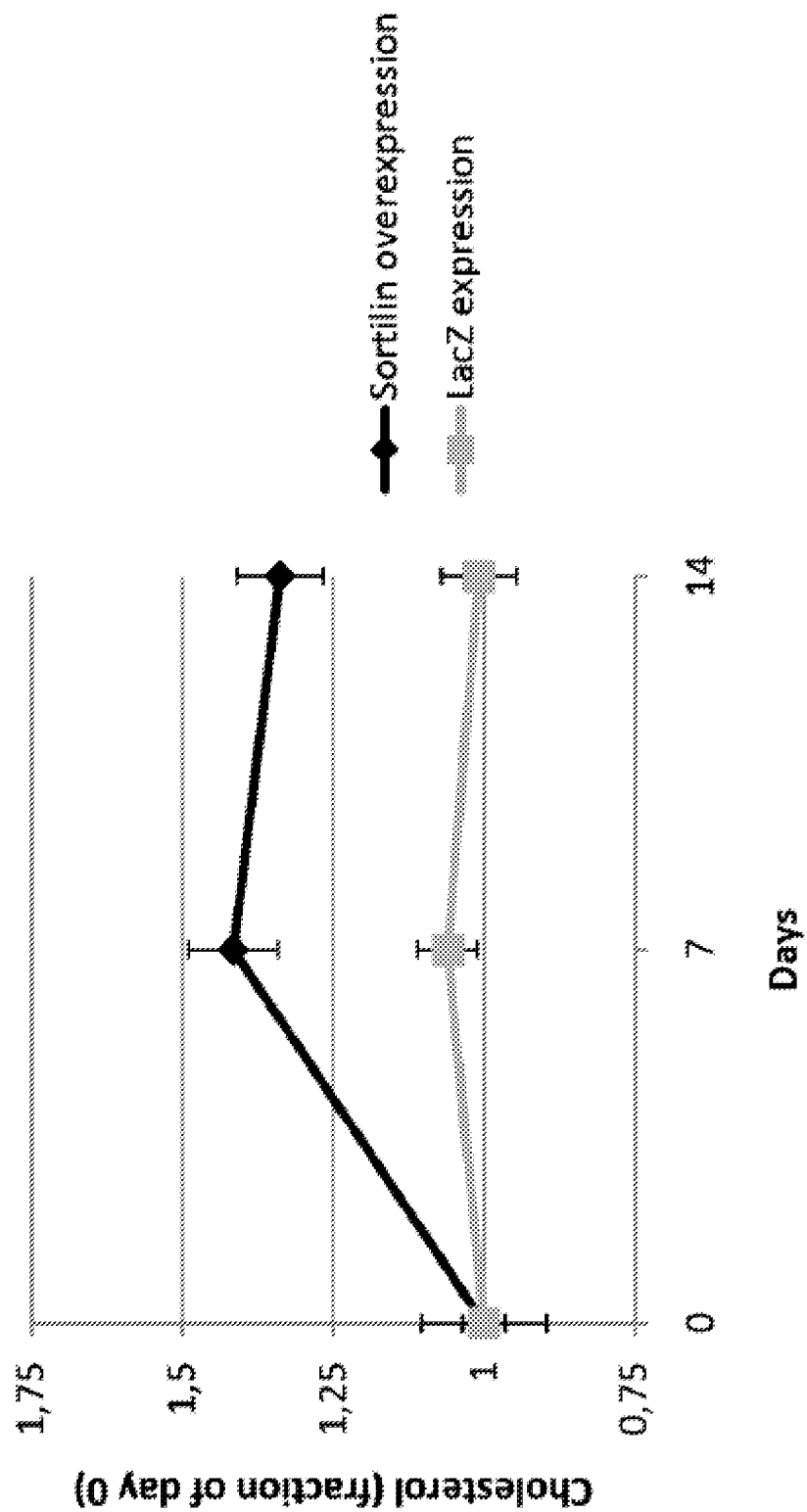

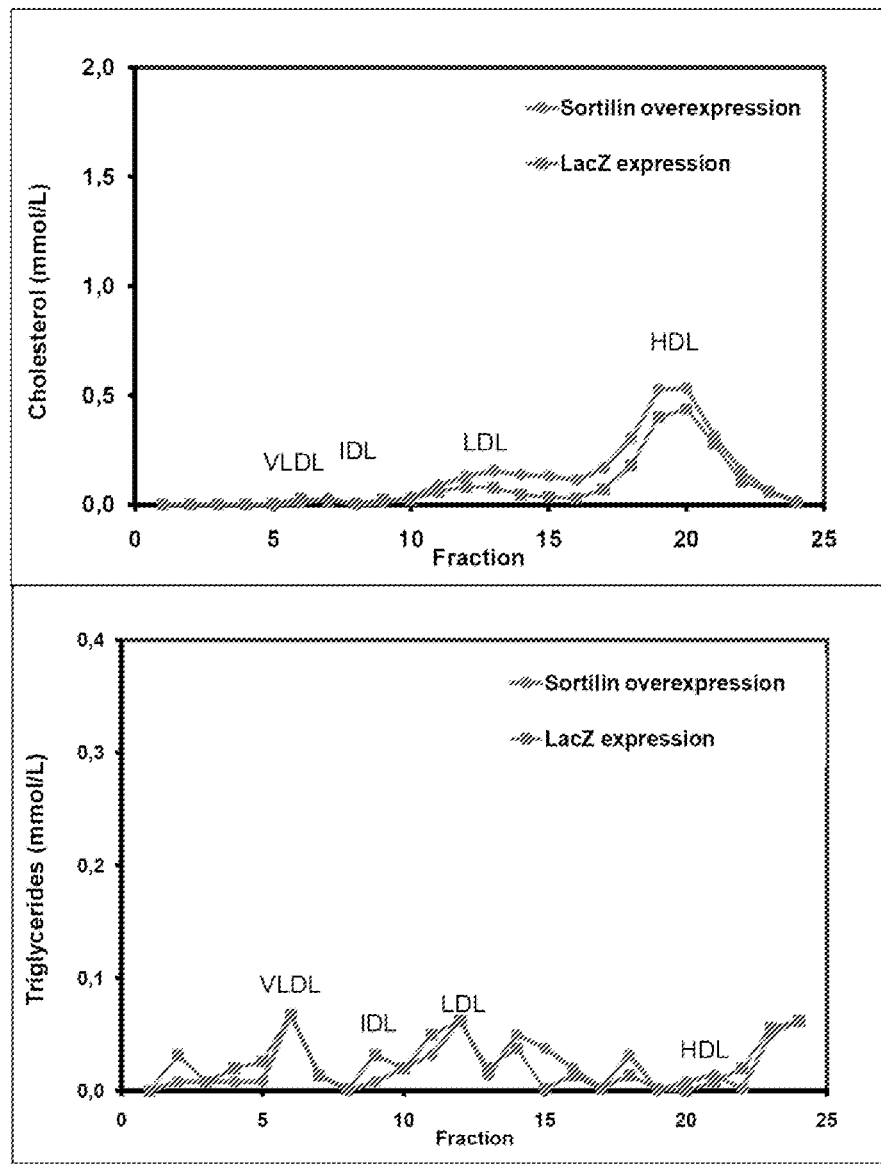
Fig. 6, continued

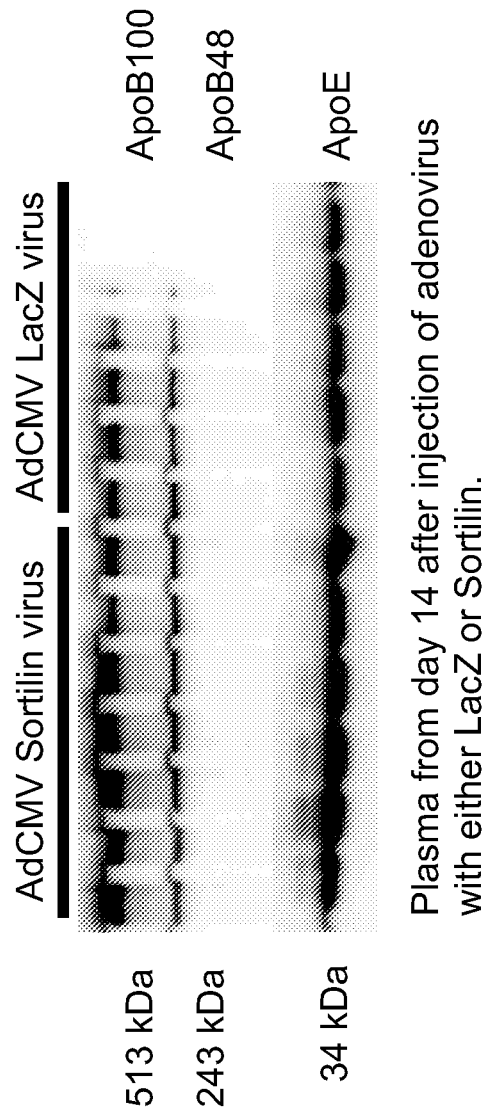

Cholesterol and triglyceride from SorLA/ApoE KO

Apoproteins and lipid profile

Competition for binding to immobilized sSortilin between 100 nM GST tagged YIL (GST-YIL) and the specified peptides.
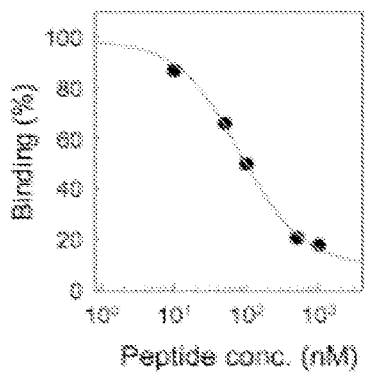
Peptide: NT
EC50: 81nM
Sequence: pELYENKPRRPYIL
Structure:
LYENKPRRPYIL
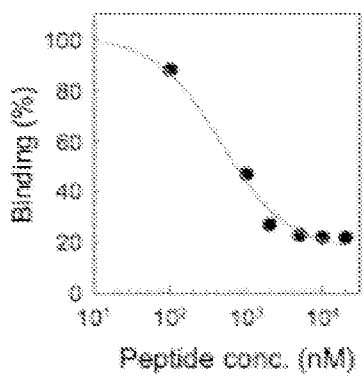
Peptide: NT8-13
EC50: 460nM
Sequence: RRPYIL
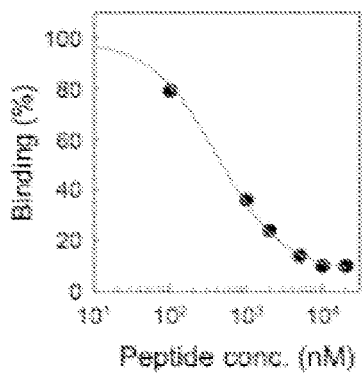
Peptide: RRPYI(chg)
EC50: 420nM
Sequence: RRPYI-cyclo-hexyl-glycine
Structure:
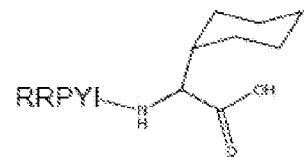
RRPYI
Fig. 10

Competition for binding to immobilized sSortilin between 100 nM GST tagged YIL (GST-YIL) and the specified peptides.
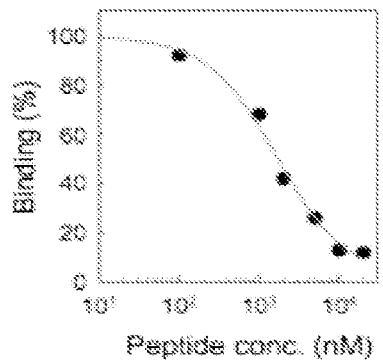
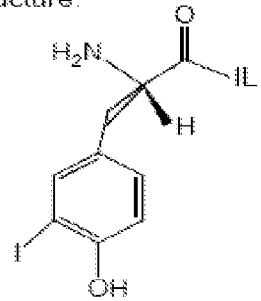
Peptide: iodoYIL
EC50: 1675 nM
Sequence: iodoYIL
Structure:
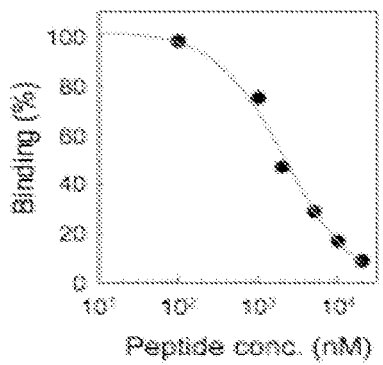
Peptide: QIL
EC50: 1700 nM
Sequence: QIL
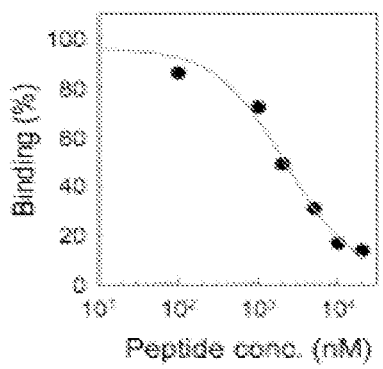
Peptide: YCL
EC50: 2230 nM
Sequence: YCL
Fig. 10, continued Competition for binding to immobilized sSortilin between 100 nM GST tagged YIL (GST-YIL) and the specified peptides.
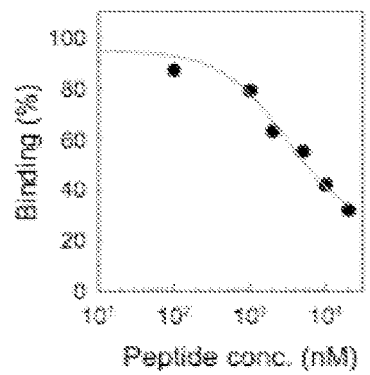
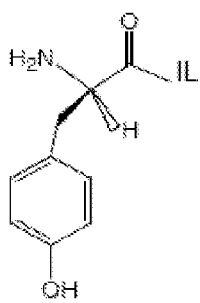
Peptide: dYIL
EC50: 3000 nM
Sequence: dYIL
Structure:
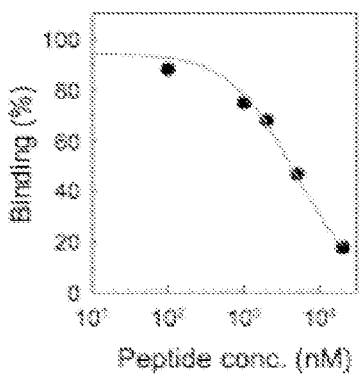
Peptide: YHL
EC50: 4580 nM
Sequence: YHL
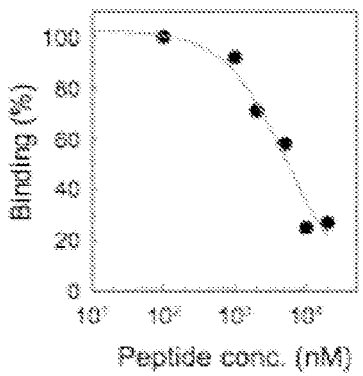
Peptide: NT69L
EC50: 5100 nM
Sequence:
Structure:
Fig. 10, continued Competition for binding to immobilized sSortilin between 100 nM GST tagged YIL (GST-YIL) and the specified peptides.
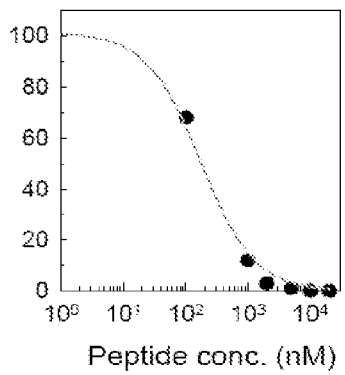
Peptide: GST-YIL (100nM)
EC50: 200nM
Sequence: YIL
Structure:
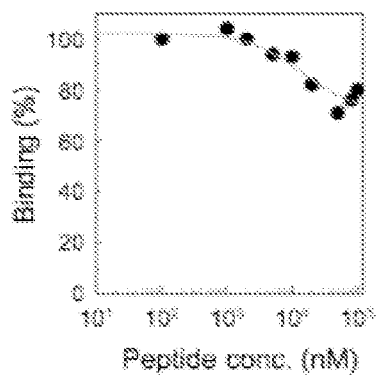
Peptide: RRPYI(acc)
EC50: 14000 nM
Sequence: RRPYI-1-amino-1-carboxy-cyclohexyl
Structure:
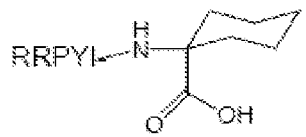
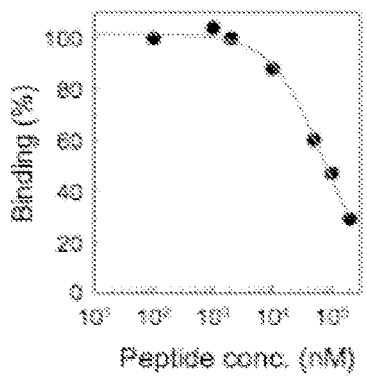
Peptide: RRPYI(nMe)L
EC50: 68000 nM
Sequence: RRPYI-N-methyl-Leucine
Structure:
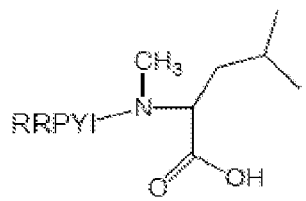
Fig. 10, continued

MODULATION OF THE VPS10P-DOMAIN FOR THE TREATMENT OF CARDIOVASCULAR DISEASE

CROSS-REFERENCE TO RELATED APPLICATIONS

The present application is a §371 U.S. National Stage Application of International Application No. PCT/DK2009/050115, filed May 20, 2009, which claims the benefit of priority under 35 U.S.C. §119(e) of U.S. Provisional Application No. 61/055,385, filed May 22, 2008, and under 35 U.S.C. §119(a)-(d) of Danish Patent Application No. PA200800592, filed May 22, 2008. Each of these applications is hereby incorporated by reference in its entirety.

This application contains a Sequence Listing, submitted in electronic form as filename 0717_Sequence_listing_as_filed.txt, of size 76,487 bytes, created on Nov. 18, 2010. The sequence listing is hereby incorporated by reference in its entirety.

All patent and non-patent references cited in the application, or in the present application, are hereby incorporated by reference in their entirety.

FIELD OF INVENTION

The present invention relates to the modulation of the Vps10p-domain receptors for the modulation of abnormal plasma lipid concentrations for the treatment of specific cardiovascular diseases. The invention further relates to identification of ligands capable of acting as antagonists/inhibitors of the Vps10p-domain receptors. The present invention also relates to the preparation and use of such ligands for treating cardiovascular disease or disorders.

BACKGROUND OF INVENTION

Plasma concentration of low-density lipoproteins (LDL) that transport cholesterol in the human circulation is one of the most important risk factors of cardiovascular morbidity and mortality (1). Excessive amounts of circulating cholesterol are deposited in the walls of coronary vessels causing closure of the vessel lumen and obstruction of blood flow to the heart (and other organs). This disease process is known as atherosclerosis. As a consequence of atherosclerotic events, coronary artery disease and myocardial infarction occur. Given the importance of management of LDL levels in patients, LDL cholesterol remains the primary target of cardiovascular therapy today (2, 3).

Risk for development of diseases and conditions like atherosclerosis, coronary artery disease, and coronary heart disease has been demonstrated to be strongly correlated with high levels of LDL-cholesterol and triglycerides. Elevated levels of low density lipoprotein-cholesterol (LDL-cholesterol) is a significant lipid associated contributor to e.g. coronary heart disease.

Atherosclerosis and its associated coronary artery disease is the leading cause of mortality in the industrialized world. Despite attempts to modify secondary risk factors (smoking, obesity, lack of exercise) and treatment of dyslipidemia with dietary modification and drug therapy, coronary heart disease remains the most common cause of death in the U.S., where cardiovascular disease accounts for 44% of all deaths, with 53% of these associated with atherosclerotic coronary heart disease.

A number of biochemical pathways that affect plasma levels of cholesterol are known and have been considered as targets in therapeutic intervention. These steps include the rate with which cholesterol is produced in the organism and introduced into very low-density lipoproteins (VLDL), the extent of conversion of VLDL into LDL, as well as the efficiency of LDL clearance into hepatic tissues. Furthermore, the conversion of cholesterol into bile acids that are secreted into the gut affect circulating lipid levels.

The Vps10p-Domain Receptor Family

The present inventors have studied the effect of modulation of activity of Vps10p-domain receptors on plasma levels of LDL-cholesterol and triglycerides. The members of this family of receptors are Sortilin, SorLA, SorCS1, SorCS2 and SorCS3.

Sortilin

Sortilin, the archetypal member of the Vps10p-domain receptor family is occasionally also referred to as Neurotensin receptor 3 (NTR3), Glycoprotein 95 (Gp95) or 100 kDa NT receptor. Human Sortilin is accessed in Swiss Prot under ID No. Q99523.

Sortilin, (SEQ ID NO. 1) is a type I membrane receptor expressed in a number of tissues, including the brain, spinal cord, testis, liver and skeletal muscle (6-7). Sortilin belongs to a family of receptors comprising Sortilin, SorLA (8), SorCS1, SorCS2 and SorCS3.

All the receptors in this family share the structural feature of an approximately 600-amino acid N-terminal domain with a strong resemblance to each of the two domains which constitute the luminal portion of the yeast sorting receptor Vps10p (9). The Vps10p-domain (Vps10p-D) that among other ligands binds neurotrophic factors and neuropeptides (10-14), constitutes the entire luminal part of Sortilin (sSortilin) and is activated for ligand binding by enzymatic propeptide cleavage (10, 11). Sortilin is a multifunctional type-1 receptor capable of endocytosis as well as intracellular sorting (9-11), and as shown recently, it also engages in signaling by triggering proneurotrophin-induction of $p75^{NTR}$-mediated neuronal apoptosis (12, 13, 18, 19). Sortilin is synthesized as a proprotein, which is converted to mature Sortilin by enzymatic cleavage and removal of a short N-terminal propeptide. Only the mature receptor binds ligands and interestingly, all its known ligands, e.g. Neurotensin (NT), lipoprotein lipase, the proforms of nerve growth factor-β (proNGF) and brain derived neurotrophic factor (proBDNF), receptor associated protein (RAP), and its own propeptide, compete for binding (11-13, 16), indicating that the diverse ligands target a shared or partially shared binding site. NT is a tridecapeptide, which binds to Sortilin, SorLA and the two G-protein coupled receptors NTR1 and NTR2 (10, 20-22). The physiological role of NT in relation to Sortilin has not been fully elucidated (23), still NT is an important tool, as it inhibits all other ligands from binding to the Sortilin Vps10p-D.

SorLA

Sorting protein-related receptor abbreviated SorLA (Swiss prot ID no Q92673), also known as LR11, is a 250-kDa type-1 membrane protein and the second member identified in the Vps10p-domain receptor family SorLA, like sortilin, whose lumenal domain consists of a Vps10p domain only, is synthesized as a proreceptor that is cleaved by furin in late Golgi compartments. It has been demonstrated that the truncation conditions the Vps10p domain for propeptide inhibitable binding of neuropeptides and the receptor-associated protein. It has been demonstrated (21) that avid binding of the receptor-associated protein, apolipoprotein E, and lipoprotein lipase not inhibited by propeptide occurs to sites located in other lumenal domains. In transfected cells, about 10% of fulllength SorLA is expressed on the cell surface capable mediating endocytosis. The major pool of receptors is found in late Golgi compartments, and interaction with newly synthesized ligands has been suggested.

SorCS-3

SorCS1 (Swiss prot ID no Q8WY21), SorCS2 (Swiss prot ID no Q96PQ0) and SorCS3 (Swiss prot ID no Q9UPU3) constitute a subgroup of mutually highly similar proteins containing both a Vps10p-D and a leucine-rich domain bordering the transmembrane domain (14, 26). SorCS1 may play an important role outside the nervous system as its region on the gene was identified as a type 2 diabetes quantitative trait locus in mice (27), and variations in the human SorCS1 gene are associated with diabetes-related traits (28). Further indications in this direction are presented in another study (29) wherein SorCS1 is associated with the major glucose-controlling 16-Mb Niddm1i region in the diabetic GK rat, a region which causes defective insulin secretion and which also corresponds to loci in humans and mice associated with type 2 diabetes.

STATE OF THE ART

The current state of the art for therapy of high plasma LDL is the application of statins, inhibitors that interfere with endogenous cholesterol production and thereby reduce the output of cholesterol-rich LDL particles. However, the use of statins is associated with a substantial risk of side affects such as adverse effects on muscle and liver functions, as well as on cognitive abilities (4, 5). Thus, extensive research efforts are directed towards identification of novel factors contributing to the regulation of plasma cholesterol metabolism. These factors may represent safer alternatives to therapeutic intervention with high plasma LDL levels.

Recently, a number of groups have used genome-wide association studies to identify chromosomal regions in the human genome that may be associated with control of plasma lipid values. Notably, these studies merely suggest certain regions on particular chromosomes that may have some predictive value for lipid concentrations and cardiovascular risk. None of these studies provides experimental evidence to confirm a causal role of candidate genes in said chromosomal region in control of lipid homeostasis.

For example, Willer et al. (6) as well as Kathiresan et al. (7) both have mapped a chromosomal locus associated with LDL cholesterol to 1p13. This locus contains several candidate genes among which are CELSR2, PSRC1 and SORT1. Whether any of the three genes, or others ones in this region may be relevant for determination of LDL cholesterol is unclear as stated by Kathiresan et al on page 191: "It is not yet clear what causal variants or even the causal genes are at the new locus". Even more confusing, Kathiresan et al. identify an increase in mRNA levels for SORT1 with the C-allele that predisposes its carrier to low plasma LDL. The authors conclude " . . . these observations suggest a mechanism by which increased sortilin expression seen with the C allele (at SNP rs646776) could lead to lower circulating LDL cholesterol concentrations". In the authors' argumentation, sortilin acts as a protective factor reducing circulating LDL levels. The higher the mRNA levels for sortilin (SORT1), the lower the plasma LDL concentration.

This assumption, however, is incorrect as demonstrated by the present inventors by functional studies using sortilin-deficient mouse models wherein loss of sortilin expression in fact is associated with low plasma LDL. Thus, normal sortilin activity increases rather than decreases LDL concentrations. The increase seen in the C allele in the study by Kathiresan et al. is likely to reflects a compensatory up-regulation of a dysfunctional sortilin allele.

The patent application WO 2004/056385 discloses a method of treating a disease or disorder selected from inflammatory pain, diseases or disorders of pancreas, kidney disorders, lung disorders, cardiovascular disorders, various types of tumours, psychiatric disorders or neuronal disorders by use of agents capable of inhibiting Vps10p-domain receptors, in particular Sortilin. However, WO 2004/056385 do not disclose that Sortilin is involved in the regulation of plasma lipid levels.

Other patent applications such as WO 2006/138343 and WO 2007/035716 discloses compositions comprising receptor-associated protein (RAP) binding CR containing receptors/proteins for treating a large number of diseases including cardiovascular disease. The listing in this document of Sortilin as a protein comprising CR repeats is incorrect however as is the referral to SwissProt access number O92673 along with Sortilin. Q92673 is the SwissProt access number for the Vps10p-domain receptor SorLA which do indeed comprise CR repeats to which RAP may bind.

A further patent application WO 2007/141346 discloses genes regulating intracellular cholesterol trafficking as targets for treatment of cholesterol-related diseases. The Vps10p-domain receptor member SorCS1 is disclosed as one out of several potential targets without further disclosure of a mechanism or association to other Vps10p-domain receptors.

SUMMARY OF THE INVENTION

In a main aspect the present invention relate to the use of at least one antagonist capable of binding to a receptor of the Vps10p-domain family thus inhibiting the activity of said Vps10p-domain receptor, in the manufacture of a medicament, for the treatment and/or prevention of abnormal plasma lipid concentrations in an animal.

In another aspect, the invention relate to the use of at least one antagonist capable of binding to at least one amino acid residue of a Vps10p-domain receptor agonist selected from the group consisting of SEQ ID NOs. 6, 7, 8, 9, 10, 14 or 15 or a fragment or variant thereof, in the manufacture of a medicament, for the treatment and/or prevention of abnormal plasma lipid concentrations in an animal.

In a further aspect, the invention concerns an in vitro method for screening for an antagonist capable of binding to a Vps10p-domain receptor, comprising the steps of:

a) providing a Vps10p-domain receptor, and
b) providing an agonist,
c) providing a library of potential antagonists, and
d) providing an assay for measuring the binding of an agonist to a Vps10p-domain receptor, and
e) adding the library of potential antagonists to be tested to the assay, and
f) determining the amount of agonist bound to the Vps10p-domain receptor, and
g) comparing the amount determined in step f) with an amount measured in the absence of the antagonist to be tested,
h) wherein the difference in the two amounts identifies an antagonist which alters the binding of the agonist to the Vps10p-domain receptor.

In yet another aspect the present invention relates to a method for determining the degree of inhibition of an antagonist on activity of a Vps10p-domain receptor in a cell culture expressing said receptor, wherein said Vps10p-domain receptor comprises an amino acid sequence having at least 60% sequence identity to SEQ ID NO. 1, SEQ ID NO. 2, SEQ ID NO. 3, SEQ ID NO. 4 or SEQ ID NO. 5, said method comprising the steps of:

a) providing a cell culture expressing a Vps10p-domain receptor, and b) providing an agonist of the Vps10p-domain receptor, and c) providing a library of potential antagonists, and d) providing an assay for determination of binding to, internalisation of and signalling through, a Vps10p-domain receptor, said assay comprising e) adding the library of potential antagonists to be tested c) to the cell culture a), in the presence of the agonist b), and f) determining
  i) the amount of antagonist bound to the Vps10p-domain receptor, and/or
  ii) the amount of antagonist internalised by the Vps10p-domain receptor, and/or
  iii) the degree of signalling through the Vps10p-domain receptor, and g) comparing the amount determined in step f) with an amount measured in the absence of the antagonist to be tested, h) wherein the difference in the two amounts identifies an antagonist
  i) capable of binding to a Vps10p-domain receptor, and/or
  ii) capable of inhibiting signalling through a Vps10p-domain receptor, and/or
  iii) capable of inhibiting internalisation of an agonist of said Vps10p-domain receptor.

In a further aspect the present invention relates to a method for determining the degree of inhibition of an antagonist on activity of a Vps10p-domain receptor in a cell culture expressing said receptor and with the a cell culture lacking expression of said receptor, said method comprising the steps of:

a) providing a cell culture expressing a Vps10p-domain receptor, and b) providing a cell culture not expressing a Vps10p-domain receptor, and c) optionally providing a cell culture overexpressing a Vps10p-domain receptor d) providing an agonist of the Vps10p-domain receptor, and e) providing a library of potential antagonists, and f) providing a first assay comprising a) and a second assay comprising b) and optionally a third assay comprising c), and g) adding the library of potential antagonists to be tested to the three assays, and h) determining
  i) the amount of antagonist bound to the Vps10p-domain receptor, and/or
  ii) the amount of antagonist internalised by the Vps10p-domain receptor, and/or
  iii) the degree of signalling through the Vps10p-domain receptor, and i) comparing the amount of antagonist determined in step g) using a) with the amount determined in g) using b) and the amount determined in g) using c), j) wherein the difference in the amounts identifies an antagonist
  i) capable of binding to a Vps10p-domain receptor, and/or
  ii) capable of inhibiting signalling through a Vps10p-domain receptor, and/or
  iii) capable of inhibiting internalisation of an agonist of said Vps10p-domain receptor.

In a further aspect the present invention relates to a method for determining the degree of inhibition of an antagonist on activity of a Vps10p-domain receptor in a mammal expressing said receptor, said method comprising the steps of:

a) administering said antagonist to a mammal naturally expressing the receptor, b) determining
  i) the amount of antagonist bound to the Vps10p-domain receptor, and/or
  ii) the amount of antagonist internalised by the Vps10p-domain receptor, and/or
  iii) the degree of signalling through the Vps10p-domain receptor, and c) comparing the measurement of step b) with a measurement obtained in the absence of the compound to be tested, d) wherein the difference in the two measurements identifies the effect of said antagonist on said mammal naturally expressing the receptor.

In yet another aspect the present invention relate to a method for determining the degree of inhibition of an antagonist on activity of a Vps10p-domain receptor in a mammal expressing said receptor with a second mammal, lacking expression of said receptor and a third mammal overexpressing said receptor, said method comprising the steps of:

a) providing a mammal expressing a Vps10p-domain receptor, and b) providing a mammal not expressing a Vps10p-domain receptor, and c) providing a mammal overexpressing a Vps10p-domain receptor, and d) providing an agonist of the Vps10p-domain receptor, and e) providing a library of potential antagonists, and f) administering said library of antagonists to said mammal of a), b) and c) respectively, and g) determining
  i) the amount of antagonist bound to the Vps10p-domain receptor, and/or
  ii) the amount of antagonist internalised by the Vps10p-domain receptor, and/or
  iii) the degree of signalling through the Vps10p-domain receptor, in each of the mammals defined in a), b) and c), and h) comparing the amount of antagonist determined in step g) using a) with the amount determined in g) using b) with the amount determined in g) using c), i) wherein the difference in the amounts identifies an antagonist
  i) capable of binding to a Vps10p-domain receptor, and/or
  ii) capable of inhibiting signalling through a Vps10p-domain receptor, and/or
  iii) capable of inhibiting internalisation of an agonist of said Vps10p-domain receptor.

In a further aspect the present invention relates to a pharmaceutical composition comprising the antagonist of claim 1, said antagonist selected from the group consisting of small organic compounds, oligo-peptides, proteins and monoclonal or polyclonal antibodies.

In an important aspect the present invention relate to the use of the pharmaceutical composition described herein above for the preparation of a medicament for the treatment or prevention of a disease or disorder associated with abnormal plasma lipid concentrations.

In a further aspect the present invention relates to a method of treatment of a pathological condition of the cardiovascular system associated with abnormal plasma lipid concentrations in a subject comprising administering to an individual in need thereof a therapeutically effective amount of the pharmaceutical composition defined herein above.

In a further aspect the present invention relates to a kit in parts comprising:

a pharmaceutical composition as defined herein above,
a medical instrument or other means for administering the medicament,
instructions on how to use the kit in parts.

In a further aspect the present invention relates to the use at least one antagonist wherein said antagonist is capable of inhibiting expression of a Vps10p-domain receptor in an animal.

OVERVIEW OF THE DRAWINGS

FIG. 1: Receptor overview
FIG. 2a: Cholesterol and triglyceride metabolism
FIG. 2b: Cholesterol and triglyceride metabolism
FIG. 3: Plasma cholesterol diagram
FIG. 4: Plasma triglyceride diagram
FIG. 5a: Lipoprotein profile—cholesterol and triglyceride
FIG. 5b: Surface plasmon resonance analysis of ApoB binding to sortilin.
FIG. 6: Time-course for increase in cholesterol levels and FPLC profile in mice that over-express Sortilin.
FIG. 7: Western Blot (WB) of plasma from mice that over-express sortilin
FIG. 8: Cholesterol and triglyceride
FIG. 9: Apoproteins and lipid profile
FIG. 10: Competition binding to immobilized sortilin using peptides

DETAILED DESCRIPTION ON THE INVENTION

Definitions

Abnormal plasma lipid concentrations: The expression abnormal plasma lipid concentrations as used herein refer to the level of one or more of the following plasma lipid levels: total cholesterol, LDL-cholesterol, HDL cholesterol and triglyceride. Abnormal levels as such are levels (i.e. concentrations) falling outside one or more of the following intervals of Table 1:

TABLE 1

| Normal plasma lipid levels | |
|---|---|
| Patient group | Concentration |
| A: Total cholesterol | |
| Men and women aged 19-29 years | 3.5-6.2 mM |
| Men and women aged 30-59 years | 4.4-7.8 mM |
| Women over 59 years of age | 4.8-8.0 mM |
| Men over 59 years of age | 4.3-7.3 mM |
| Children under 1 year of age | 1.5-4.5 mM |
| Children aged 1-18 years | 2.7-6.0 mM |
| Recommended limit for treatment in patients suffering from cardiovascular disorders, when total cholesterol is higher than: | 5 mM |
| Recommended limit for treatment in patients suffering from diabetes, when total cholesterol is higher than: | 4.5 mM |
| B: LDL-cholesterol | |
| Women aged 20-29 years | 1.5-4.3 mM |
| Women aged 30-45 years | 1.9-4.5 mM |
| Women over 45 years of age | 2.4-5.5 mM |
| Men aged 20-29 years | 1.7-4.3 mM |
| Men aged 30-45 years | 2.1-5.0 mM |
| Men aged 46-69 years | 2.3-5.3 mM |
| Men over 69 years of age | 2.3-4.8 mM |
| Children aged 10-19 years | 1.8-3.5 mM |
| Adults with increased risk of cardiovascular disorder when LDL-cholesterol is higher than: | 3 mM |

TABLE 1-continued

| Normal plasma lipid levels | |
|---|---|
| Patient group | Concentration |
| C: HDL-cholesterol | |
| Women aged 20-40 years | 1.0-2.0 mM |
| Women over 4o years of age | 1.0-2.3 |
| Men aged 20-60 years | 0.7-1.7 mM |
| Men over 60 years of age | 0.8-1.9 mM |
| Adults with increased risk of cardiovascular disorder when HDL-cholesterol is higher than: | 1 mM |
| D: Triglycerides | |
| Men and women aged 20-40 years | 0.4-1.6 mM |
| Men and women over 40 years of age | 0.5-2.5 mM |
| Children 0-9 years | 0.3-1.2 mM |
| Adults with increased risk of cardiovascular disorder when triglyceride level is higher than: | 2 mM |

Table 1 Sources:
"Dansk Laboratorie medicin, En Håndbog" Jørgen Lyngbye, 2001
Konsensus, www.cardio.dk on 18 May 2009 (Dansk Kardiologisk Selskab).

Adjuvant: Any substance whose admixture with an administered immunogenic determinant/antigen increases or otherwise modifies the immune response to said determinant.

Affinity: The interaction of most ligands with their binding sites can be characterized in terms of a binding affinity. In general, high affinity ligand binding results from greater intermolecular force between the ligand and its receptor while low affinity ligand binding involves less intermolecular force between the ligand and its receptor. In general, high affinity binding involves a longer residence time for the ligand at its receptor binding site than is the case for low affinity binding. High affinity binding of ligands to receptors is often physiologically important when some of the binding energy can be used to cause a conformational change in the receptor, resulting in altered behavior of an associated ion channel or enzyme.

A ligand that can bind to a receptor, alter the function of the receptor and trigger a physiological response is called an agonist for that receptor. Agonist binding to a receptor can be characterized both in terms of how much physiological response can be triggered and the concentration of the agonist that is required to produce the physiological response. High affinity ligand binding implies that a relatively low concentration of a ligand is adequate to maximally occupy a ligand binding site and trigger a physiological response. Low affinity binding implies that a relatively high concentration of a ligand is required before the binding site is maximally occupied and the maximum physiological response to the ligand is achieved. Ligand binding is often characterized in terms of the concentration of ligand at which half of the receptor binding sites are occupied, known as the dissociation constant ($k_d$). Accordingly, an antagonist capable of binding to a receptor of the Vps10p-domain family thus inhibiting the activity of said Vps10p-domain receptor may be an antagonist having higher affinity to the binding site of a Vps10p-domain agonist than said agonist itself.

Alcohol: A class of organic compounds containing one or more hydroxyl groups (OH). In this context a saturated or unsaturated, branched or unbranched hydrocarbon group sitting as a substituent on a larger molecule.

Alicyclic group: the term "alicyclic group" means a cyclic hydrocarbon group having properties resembling those of aliphatic groups.

Aliphatic group: in the context of the present invention, the term "aliphatic group" means a saturated or unsaturated linear or branched hydrocarbon group. This term is used to encompass alkyl, alkenyl, and alkynyl groups, for example.

Alkyl group: the term "alkyl group" means a saturated linear or branched hydrocarbon group including, for example, methyl, ethyl, isopropyl, t-butyl, heptyl, dodecyl, octadecyl, amyl, 2-ethylhexyl, and the like.

Alkenyl group: the term "alkenyl group" means an unsaturated, linear or branched hydrocarbon group with one or more carbon-carbon double bonds, such as a vinyl group.

Alkynyl group: the term "alkynyl group" means an unsaturated, linear or branched hydrocarbon group with one or more carbon-carbon triple bonds.

Amphiphil: substance containing both polar, water-soluble and nonpolar, water-insoluble groups.

Agonist: An agonist is a compound capable of increasing or effecting the activity of a receptor. Specifically, a Vps10p-domain receptor agonist is a compound capable of binding to one or more of binding sites of a Vps10p-domain receptor thereby inducing the same physiological response as a given endogenous agonist ligand compound.

Antagonist: An antagonist is in this case synonymous with an inhibitor. An antagonist is a compound capable of decreasing the activity of an effector such as a receptor. Specifically, a Vps10p-domain receptor antagonist is a compound capable of binding to one or more of binding sites of Vps10p-domain receptor thereby inhibiting binding of another ligand thus inhibiting a physiological resonse.

antisense-RNA: an RNA molecule capable of causing gene silencing by specifically binding to an mRNA molecule of interest.

antisense-DNA: a DNA molecule capable of causing gene silencing by specifically binding to an mRNA molecule of interest.

Apoptosis: Apoptosis is a process of suicide by a cell in a multi-cellular organism. It is one of the main types of programmed cell death (PCD), and involves an orchestrated series of biochemical events leading to a characteristic cell morphology and death.

Apoptosis inhibitor: Any compound capable of decreasing the process of apoptosis.

Aromatic group: the term "aromatic group" or "aryl group" means a mono- or polycyclic aromatic hydrocarbon group.

Binding: The term "binding" or "associated with" refers to a condition of proximity between chemical entities or compounds, or portions thereof. The association may be non-covalent-wherein the juxtaposition is energetically favoured by hydrogen bonding or van der Waals or electrostatic interactions- or it may be covalent.

Binding site: The term "binding site" or "binding pocket", as used herein, refers to a region of a molecule or molecular complex that, as a result of its shape, favourably associates with another molecule, molecular complex, chemical entity or compound. As used herein, the pocket comprises at least a deep cavity and, optionally a shallow cavity.

Binding site 1 of Sortilin: A high affinity binding site of neurotensin or synonymously binding site 1 is a binding site of sortilin (SEQ ID NO. 1) having high affinity for neurotensin or a fragment or variant of neurotensin, and having affinity for the sortilin propeptide or a fragment thereof (Amino acid residues 34-77 of SEQ ID NO. 1) said binding site comprising amino acid residues R325, S316, Y351, I353, K260, I327, F314, F350 to M363, S305, F306, T398 to G400, I303-G309, Q349-A356, Y395 and T402 of SEQ ID NO. 1. More preferably, binding site 1 comprises amino acids R325, S316, Y351, I353, K260, I327, F314, F350 to M363, S305, F306 and T398 to G400 of SEQ ID NO. 1. Most preferably binding site 1 of sortilin comprises amino acids R325, S316, Y351, I353, K260, I327, F314 and F350 to M363 of SEQ ID NO. 1. Binding site 1 is a promiscuous binding site.

Binding site 2 of Sortilin: A binding site of sortilin having low affinity for neurotensin or a fragment or variant of neurotensin, said binding site comprising amino acid residues L572, L114, V112, R109 to S111, S115 to G118, T570, G571, W586, W597, T168-I174, L572, A573 and S584 to F588 of SEQ ID NO. 1. More preferably the sortilin low affinity binding site of neurotensin comprises amino acids L572, L114, V112, R109 to S111, S115 to G118, T570, G571, W586 and W597 of SEQ ID NO. 1. Most preferably the sortilin low affinity binding site of neurotensin comprises amino acids L572, L114 and V112. Binding site 2 is promiscuous and may bind the propeptide of Sortilin (amino acid residues 34-77 of SEQ ID NO. 1).

Binding site 3 of Sortilin: A promiscuous binding site of sortilin comprising amino acid residues D403, S420, D422, N423, S424, I425, Q426, E444, T451, Y466, E470, I498, S499 and V500 of SEQ ID NO. 1, more preferably comprising amino acid residues D403, N423, S424, I425, T451, Y466, I498 and V500 of SEQ ID NO. 1, most preferably comprising amino acid residues T451, Y466, I498 and V500 of SEQ ID NO. 1.

Bioreactive agent: The term "bioactive agent" as used herein refers to any a substance which may be used in connection with an application that is therapeutic or diagnostic, such as, for example, in methods for diagnosing the presence or absence of a disease in a patient and/or methods for the treatment of a disease in a patient. "Bioactive agent" refers to substances, which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, polypeptides, peptides, vitamins, steroids, steroid analogues and genetic determinants, including nucleosides, nucleotides and polynucleotides.

Cerebral ischemia: Global cerebral ischemia is an ischemic condition where the brain does not receive enough blood flow to maintain normal neurological function.

Coma: A prolonged period of unconsciousness following brain injury or metabolic disorders. The person in coma may have a simple reflex in response to touch or pain, but essentially there is no meaningful response to external stimuli.

Cationic group: A chemical group capable of functioning as a proton donor when a compound comprising the chemical group is dissolved in a solvent, preferably when dissolved in water.

Complex: As used herein the term "complex" refers to the combination of a molecule or a protein, conservative analogues or truncations thereof associated with a chemical entity.

Coordinate: The term "coordinate" as use herein, refers to the information of the three dimen-sional organization of the atoms contributing to a protein structure. The final map containing the atomic coordinates of the constituents of the crystal may be stored on a data carrier; typically the data is stored in PDB format or in mmCIF format, both of which are known to the person skilled in the art. However, crystal coordinates may as well be stored in simple tables or text formats. The PDB format is organized according to the instructions and guidelines given by the Research Collaboratory for Structural Biology.

Cyclic group: the term "cyclic group" means a closed ring hydrocarbon group that is classified as an alicyclic group, aromatic group, or heterocyclic group.

Cycloalkenyl: means a monovalent unsaturated carbocyclic radical consisting of one, two or three rings, of three to eight carbons per ring, which can optionally be substituted with one or two substituents selected from the group consisting of hydroxy, cyano, lower alkenyl, lower alkoxy, lower haloalkoxy, alkenylthio, halo, haloalkenyl, hydroxyalkenyl, nitro, alkoxycarbonenyl, amino, alkenylamino, alkenylsulfonyl, arylsulfonyl, alkenylaminosulfonyl, arylaminosulfonyl, alkylsulfonylamino, arylsulfonylamino, alkenylaminocarbonyl, arylaminocarbonyl, alkenylcarbonylamino and arylcarbonylamino.

Cycloalkyl: means a monovalent saturated carbocyclic radical consisting of one, two or three rings, of three to eight carbons per ring, which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino and arylcarbonylamino.

Dipole-dipole interaction: The term "dipole-dipole interaction" as used herein refers to the attraction which can occur among two or more polar molecules. Thus, "dipole-dipole interaction" refers to the attraction of the uncharged, partial positive end of a first polar molecule to the uncharged, partial negative end of a second polar molecule. "Dipole-dipole interaction" also refers to intermolecular hydrogen bonding.

Electrostatic interaction: The term "electrostatic interaction" as used herein refers to any interaction occurring between charged components, molecules or ions, due to attractive forces when components of opposite electric charge are attracted to each other. Examples include, but are not limited to: ionic interactions, covalent interactions, interactions between a ion and a dipole (ion and polar molecule), interactions between two dipoles (partial charges of polar molecules), hydrogen bonds and London dispersion bonds (induced dipoles of polarizable molecules). Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent.

Familial hypercholesterolemia: (Familial hypercholesterolemia (abbreviated FH and also spelled familial hypercholesterolaemia) is a genetic disorder characterized by high cholesterol levels, specifically very high low-density lipoprotein (LDL, "bad cholesterol") levels, in the blood and early cardiovascular disease. Many patients have mutations in the LDLR gene that encodes the LDL receptor protein (c.f. FIG. 3) which removes LDL from the circulation, or apolipoprotein B (ApoB), which is the part of LDL that binds to the LDL receptor. Mutations in other genes are rare. Patients who have one abnormal copy (are heterozygous) of the LDLR gene may have premature cardiovascular disease at the age of 30 to 40. Having two abnormal copies (being homozygous) may cause severe cardiovascular disease in childhood. Heterozygous FH is a common genetic disorder, occurring in 1:500 people in most countries; homozygous FH is much rarer, occurring in 1 in a million births. Treatment of heterozygous FH is normally with statins, bile acid sequestrants or other drugs that lower cholesterol levels (hypolipidemic agents). New cases are generally offered genetic counseling. Homozygous FH often does not respond to medical therapy and may require other treatments, including LDL apheresis (removal of LDL in a method similar to dialysis) and occasionally liver transplantation. The present invention provides novel means for the preparation of a medicament for the treatment of FH and provides a method of treatment of FH. The invention does so by providing antagonists of Vps10p-domain receptors, in particular antagonists binding specifically to binding sites of Sortilin and/or SorLA.

Form a ring: means that the atoms mentioned are connected through a bond when the ring structure is formed.

Fragments: The polypeptide fragments according to the present invention, including any functional equivalents thereof, may in one embodiment comprise less than 500 amino acid residues, such as less than 450 amino acid residues, for example less than 400 amino acid residues, such as less than 350 amino acid residues, for example less than 300 amino acid residues, for example less than 250 amino acid residues, such as less than 240 amino acid residues, for example less than 225 amino acid residues, such as less than 200 amino acid residues, for example less than 180 amino acid residues, such as less than 160 amino acid residues, for example less than 150 amino acid residues, such as less than 140 amino acid residues, for example less than 130 amino acid residues, such as less than 120 amino acid residues, for example less than 110 amino acid residues, such as less than 100 amino acid residues, for example less than 90 amino acid residues, such as less than 85 amino acid residues, for example less than 80 amino acid residues, such as less than 75 amino acid residues, for example less than 70 amino acid residues, such as less than 65 amino acid residues, for example less than 60 amino acid residues, such as less than 55 amino acid residues, for example less than 50 amino acid residues. Fragments of neurotensin include, but are not limited to the C-terminal amino acids of neurotensin PYIL and YIL. In one aspect the fragment is selected from the group consisting of LYENKPRRPYIL, YENKPRRPYIL, ENKPRRPYIL, NKPRRPYIL, KPRRPYIL, PRRPYIL, RRPYIL, RPYIL, PYIL, YIL and IL and natural or artificial variants thereof. In one embodiment of the present invention, the antagonist is not neurotensin or a fragment thereof.

Functional equivalency: "Functional equivalency" as used in the present invention is, according to one preferred embodiment, established by means of reference to the corresponding functionality of a predetermined fragment of the sequence.

Functional equivalents or variants of a Vps10p-domain receptor antagonist will be understood to exhibit amino acid sequences gradually differing from the preferred predetermined peptide or polypeptide based Vps10p domain antagonist sequence, as the number and scope of insertions, deletions and substitutions including conservative substitutions increase. This difference is measured as a reduction in homology between the preferred predetermined sequence and the fragment or functional equivalent.

A functional variant obtained by substitution may well exhibit some form or degree of native Vps10p domain antagonist activity, and yet be less homologous, if residues containing functionally similar amino acid side chains are substituted. Functionally similar in this respect refers to dominant characteristics of the side chains such as hydrophobic, basic, neutral or acidic, or the presence or absence of steric bulk. Accordingly, in one embodiment of the invention, the degree of identity is not a principal measure of a fragment being a variant or functional equivalent of a preferred predetermined fragment according to the present invention.

Gene "silencing": a process leading to reduced expression of endogenous genes. Gene silencing is preferably the result of post-transcriptional reduction of gene expression.

Global ischemia: Anoxia resultant from ceased blood supply to the entire body resulting in tissue damage through a variety of mechanisms including apoptosis.

Group: (Moiety/substitution) as is well understood in this technical area, a large degree of substitution is not only tolerated, but is often advisable. Substitution is anticipated on the materials of the present invention. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, or S atoms, for example, in the chain as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, t-butyl, and the like. The same definitions apply to "alkenyl group" and "alkenyl moiety"; to "alkynyl group" and "alkynyl moiety"; to "cyclic group" and "cyclic moiety; to "alicyclic group" and "alicyclic moiety"; to "aromatic group" or "aryl group" and to "aromatic moiety" or "aryl moiety"; as well as to "heterocyclic group" and "heterocyclic moiety".

Heterocyclic group: the term "heterocyclic group" means a closed ring hydrocarbon in which one or more of the atoms in the ring is an element other than carbon (e.g., nitrogen, oxygen, sulphur, etc.).

Heterocyclyl means a monovalent saturated cyclic radical, consisting of one to two rings, of three to eight atoms per ring, incorporating one or two ring heteroatoms (chosen from N, O or $S(O)_{0-2}$, and which can optionally be substituted with one or two substituents selected from the group consisting of hydroxyl, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminofarbonyl, arylaminocarbonyl, alkylcarbonylamino, or arylcarbonylamino.

Heteroaryl means a monovalent aromatic cyclic radical having one to three rings, of four to eight atoms per ring, incorporating one or two heteroatoms (chosen from nitrogen, oxygen, or sulphur) within the ring which can optionally be substituted with one or two substituents selected from the group consisting of hydroxy, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonlamino and arylcarbonylamino.

Homology: as used herein should be understood as being synonymous to the expression sequence identity. Thus "homologous with" is synonymous to "identical to". The homology between amino acid sequences may be calculated using well known scoring matrices such as any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Fragments sharing homology with fragments of SEQ ID NO:1 to 13, respectively, are to be considered as falling within the scope of the present invention when they are preferably at least about 60 percent homologous, for example at least 65 percent homologous, for example at least 70 percent homologous, for example at least 75 percent homologous, for example at least 80 percent homologous, for example at least 85 percent homologous, for example at least 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with said predetermined fragment sequences, respectively. According to one embodiment of the invention, the homology percentages refer to identity percentages.

A further suitably adaptable method for determining structure and function relationships of peptide fragments is described in U.S. Pat. No. 6,013,478, which is herein incorporated by reference. Also, methods of assaying the binding of an amino acid sequence to a receptor moiety are known to the skilled artisan.

In addition to conservative substitutions introduced into any position of a preferred predetermined peptide or polypeptide based Vps10p domain antagonist, or a fragment thereof, it may also be desirable to introduce non-conservative substitutions in any one or more positions of such an antagonist.

A non-conservative substitution leading to the formation of a functionally equivalent fragment of a peptide or polypeptide based Vps10p domain antagonist would for example i) differ substantially in polarity, for example a residue with a non-polar side chain (Ala, Leu, Pro, Trp, Val, Ile, Leu, Phe or Met) substituted for a residue with a polar side chain such as Gly, Ser, Thr, Cys, Tyr, Asn, or Gin or a charged amino acid such as Asp, Glu, Arg, or Lys, or substituting a charged or a polar residue for a non-polar one; and/or ii) differ substantially in its effect on polypeptide backbone orientation such as substitution of or for Pro or Gly by another residue; and/or iii) differ substantially in electric charge, for example substitution of a negatively charged residue such as Glu or Asp for a positively charged residue such as Lys, His or Arg (and vice versa); and/or iv) differ substantially in steric bulk, for example substitution of a bulky residue such as His, Trp, Phe or Tyr for one having a minor side chain, e.g. Ala, Gly or Ser (and vice versa).

Variants obtained by substitution of amino acids may in one preferred embodiment be made based upon the hydrophobicity and hydrophilicity values and the relative similarity of the amino acid side-chain substituents, including charge, size, and the like. Exemplary amino acid substitutions which take various of the foregoing characteristics into consideration are well known to those of skill in the art and include: arginine and lysine; glutamate and aspartate; serine and threonine; glutamine and asparagine; and valine, leucine and isoleucine.

In addition to the variants described herein, sterically similar variants may be formulated to mimic the key portions of the variant structure and that such compounds may also be used in the same manner as the variants of the invention. This may be achieved by techniques of modelling and chemical designing known to those of skill in the art. It will be understood that all such sterically similar constructs fall within the scope of the present invention.

In a further embodiment the present invention relates to functional variants comprising substituted amino acids having hydrophilic values or hydropathic indices that are within +/−4.9, for example within +/−4.7, such as within +/−4.5, for example within +/−4.3, such as within +/−4.1, for example within +/−3.9, such as within +/−3.7, for example within +/−3.5, such as within +/−3.3, for example within +/−3.1, such as within +/−2.9, for example within +/−2.7, such as within +/−2.5, for example within +/−2.3, such as within +/−2.1, for example within +/−2.0, such as within +/−1.8, for example within +/−1.6, such as within +/−1.5, for example within +/−1.4, such as within +/−1.3 for example within +/−1.2, such as within +/−1.1, for example within +/−1.0, such as within +/−0.9, for example within +/−0.8, such as within +/−0.7, for example within +/−0.6, such as within +/−0.5, for example within +/−0.4, such as within +/−0.3, for example within +/−0.25, such as within +/−0.2 of the value of the amino acid it has substituted.

The importance of the hydrophilic and hydropathic amino acid indices in conferring interactive biologic function on a protein is well understood in the art (Kyte & Doolittle, 1982 and Hopp, U.S. Pat. No. 4,554,101, each incorporated herein by reference).

The amino acid hydropathic index values as used herein are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte & Doolittle, 1982).

The amino acid hydrophilicity values are: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4) (U.S. Pat. No. 4,554,101).

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same or other Vps10-p domain antagonists, including dimers or unrelated chemical moieties. Such functional equivalents are prepared by linkage of functionalities to groups which are found in fragment including at any one or both of the N- and C-termini, by means known in the art.

Functional equivalents may thus comprise fragments conjugated to aliphatic or acyl esters or amides of the carboxyl terminus, alkylamines or residues containing carboxyl side chains, e.g., conjugates to alkylamines at aspartic acid residues; O-acyl derivatives of hydroxyl group-containing residues and N-acyl derivatives of the amino terminal amino acid or amino-group containing residues, e.g. conjugates with fMet-Leu-Phe or immunogenic proteins. Derivatives of the acyl groups are selected from the group of alkyl-moieties (including C3 to C10 normal alkyl), thereby forming alkanoyl species, and carbocyclic or heterocyclic compounds, thereby forming aroyl species. The reactive groups preferably are difunctional compounds known per se for use in cross-linking proteins to insoluble matrices through reactive side groups.

Covalent or aggregative functional equivalents and derivatives thereof are useful as reagents in immunoassays or for affinity purification procedures. For example, a fragment of a peptide Vps10p domain antagonist according to the present invention may be insolubilized by covalent bonding to cyanogen bromide-activated Sepharose by methods known per se or adsorbed to polyolefin surfaces, either with or without glutaraldehyde cross-linking, for use in an assay or purification of anti-Vps10p-domain antibodies or cell surface receptors. Fragments may also be labelled with a detectable group, e.g., radioiodinated by the chloramine T procedure, covalently bound to rare earth chelates or conjugated to another fluorescent moiety for use in e.g. diagnostic assays.

Mutagenesis of a preferred predetermined fragment of a peptide based Vps10p domain antagonist can be conducted by making amino acid insertions, usually on the order of about from 1 to 10 amino acid residues, preferably from about 1 to 5 amino acid residues, or deletions of from about from 1 to 10 residues, such as from about 2 to 5 residues.

In one embodiment the ligand of binding site 1, 2 or 3 is an oligopeptide synthesised by automated synthesis. Any of the commercially available solid-phase techniques may be employed, such as the Merrifield solid phase synthesis method, in which amino acids are sequentially added to a growing amino acid chain (see Merrifield, J. Am. Chem. Soc. 85:2149-2146, 1963).

Equipment for automated synthesis of polypeptides is commercially available from suppliers such as Applied Biosystems, Inc. of Foster City, Calif., and may generally be operated according to the manufacturer's instructions. Solid phase synthesis will enable the incorporation of desirable amino acid substitutions into any fragment of a peptide based Vps10p domain antagonist according to the present invention. It will be understood that substitutions, deletions, insertions or any subcombination thereof may be combined to arrive at a final sequence of a functional equivalent. Insertions shall be understood to include amino-terminal and/or carboxyl-terminal fusions, e.g. with a hydrophobic or immunogenic protein or a carrier such as any polypeptide or scaffold structure capable as serving as a carrier.

Oligomers including dimers including homodimers and heterodimers of fragments of sortilin inhibitors according to the invention are also provided and fall under the scope of the invention. Functional equivalents and variants of Vps10p domain peptide or polypeptide antagonist can be produced as homodimers or heterodimers with other amino acid sequences or with native sortilin inhibitor sequences. Heterodimers include dimers containing immunoreactive sortilin inhibiting fragments as well as sortilin inhibiting fragments that need not have or exert any biological activity.

Vps10p-domain receptor antagonists including but not limited to Sortilin inhibiting peptide fragments may be synthesised both in vitro and in vivo. Method for in vitro synthesis are well known, and methods being suitable or suitably adaptable to the synthesis in vivo of sortilin inhibitors are also described in the prior art. When synthesized in vivo, a host cell is transformed with vectors containing DNA encoding a sortilin peptide inhibitor or a fragment thereof. A vector is defined as a replicable nucleic acid construct. Vectors are used to mediate expression of a peptide based Vps10p domain antagonist. An expression vector is a replicable DNA construct in which a nucleic acid sequence encoding the predetermined sortilin inhibiting fragment, or any functional equivalent thereof that can be expressed in vivo, is operably linked to suitable control sequences capable of effecting the expression of the fragment or equivalent in a suitable host. Such control sequences are well known in the art. Both prokaryotic and eukaryotic cells may be used for synthesising ligands. Cultures of cells derived from multicellular organisms however represent preferred host cells. In principle, any higher eukaryotic cell culture is workable, whether from vertebrate or invertebrate culture. Examples of useful host cell lines are VERO and HeLa cells, Chinese hamster ovary (CHO) cell lines, and WI38, BHK, COS-7, 293 and MDCK cell lines. Preferred host cells are eukaryotic cells known to synthesize endogenous sortilin inhibitors. Cultures of such host cells may be isolated and used as a source of the fragment, or used in therapeutic methods of treatment, including therapeutic methods aimed at promoting or inhibiting a growth state, or diagnostic methods carried out on the human or animal body.

Hydrophobic bond: The term "hydrogen bond" as used herein refers to an attractive force, or bridge, which may occur between a hydrogen atom which is bonded covalently to an electronegative atom, for example, oxygen, sulphur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

Hydrophobic interaction: The term "hydrophobic interaction" as used herein refers to any interaction occurring between essentially non-polar (hydrophobic) components located within attraction range of one another in a polar environment (e.g. water). As used herein, attraction range is on the scale of from 0.1 up to 2 nm. A particular type of hydrophobic interaction is exerted by "Van der Waal's forces", i.e. the attractive forces between non-polar molecules that are accounted for by quantum mechanics. Van der Waal's forces are generally associated with momentary dipole moments which are induced by neighbouring molecules and which involve changes in electron distribution.

Hyperlipidemia: which is also known as hyperlipoproteinemia or dyslipidemia is the presence of raised or abnormal levels of lipids and/or lipoproteins in the blood. Lipids (fatty molecules) are transported in a protein capsule, and the density of the lipids and type of protein determines the fate of the particle and its influence on metabolism. Lipid and lipoprotein abnormalities are extremely common in the general population, and are regarded as a highly modifiable risk factor for cardiovascular disease due to the influence of cholesterol, one of the most clinically relevant lipid substances, on atherosclerosis. In addition, some forms may predispose to acute pancreatitis. Hyperlipoproteinemia may be classified into the following subtypes: Hyperlipidemia as used herein is to be understood as a condition characterized by blood plasma concentrations of HDL-cholesterol and/or LDL-cholesterol and/or triglycerides higher than the recommended values listed in table 1 herein.

Hyperlipoproteinemia Type I

This very rare form (also known as Buerger-Gruetz syndrome, primary hyperlipoproteinaemia, or familial hyperchylomicronemia) is due to a deficiency of lipoprotein lipase (LPL) or altered apolipoprotein C2, resulting in elevated chylomicrons, the particles that transfer fatty acids from the digestive tract to the liver. Lipoprotein lipase is also responsible for the initial breakdown of endogenously made triacylglycerides in the form of very low density lipoprotein (VLDL). As such, one would expect a defect in LPL to also result in elevated VLDL. Its prevalence is 0.1% of the population.

Hyperlipoproteinemia Type II

Hyperlipoproteinemia type II, by far the most common form, is further classified into type IIa and type IIb, depending mainly on whether there is elevation in the triglyceride level in addition to LDL cholesterol.

Hyperlipoproteinemia Type IIa

Familial hypercholesterolemia—This may be sporadic (due to dietary factors), polygenic, or truly familial as a result of a mutation either in the LDL receptor gene on chromosome 19 (0.2% of the population) or the ApoB gene (0.2%). The familial form is characterized by tendon xanthoma, xanthelasma and premature cardiovascular disease.

Hyperlipoproteinemia Type IIb

The high VLDL levels are due to overproduction of substrates, including triglycerides, acetyl CoA, and an increase in B-100 synthesis. They may also be caused by the decreased clearance of LDL. Prevalence in the population is 10%.

Familial Combined Hyperlipoproteinemia (FCH)

Secondary combined hyperlipoproteinemia (usually in the context of metabolic syndrome, for which it is a diagnostic criterion). While dietary modification is the initial approach for treatment of the above mentioned types of hyperlipoproteinemia, many patients require treatment with statins (HMG-CoA reductase inhibitors) to reduce cardiovascular risk. If the triglyceride level is markedly raised, fibrates may be preferable due to their beneficial effects. Combination treatment of statins and fibrates, while highly effective, causes a markedly increased risk of myopathy and rhabdomyolysis and is therefore only done under close supervision. Other agents commonly added to statins are ezetimibe, niacin and bile acid sequestrants. There is some evidence for benefit of plant sterol-containing products and w3-fatty acids. The present invention provide a novel strategy for controlling the lipid levels of patients in need thereof.

Hyperlipoproteinemia Type III

This form is due to high chylomicrons and IDL (intermediate density lipoprotein). Also known as broad beta disease or dysbetalipoproteinemia, the most common cause for this form is the presence of ApoE E2/E2 genotype. It is due to cholesterol-rich VLDL (β-VLDL). Prevalence is 0.02% of the population.

Hyperlipoproteinemia Type IV

This form is due to high triglycerides. It is also known as hypertriglyceridemia (or pure hypertriglyceridemia). According to the NCEP-ATPIII definition of high triglycerides (>200 mg/dl), prevalence is about 16% of adult population.

Hyperlipoproteinemia Type V

This type is very similar to Hyperlipoproteinemia type I, but with high VLDL in addition to chylomicrons. It is also associated with glucose intolerance and hyperuricemia. Further, unclassified and rare forms include Hypo-alpha lipoproteinemia and Hypo-beta lipoproteinemia.

Antagonists according to the present invention can be used for the preparation of a medicament for the treatment or prevention of hyperlipoproteinemia I, IIa, IIb, III, IV and V.

Inhibiting: The term inhibiting as used herein refers to the prevention of binding between two or more components.

Ligands identified by the present invention are capable of inhibiting binding between a Vps10p-domain receptor and a proneurotrophin.

Inhibiting binding: The term inhibiting binding between e.g. a proneurotrophin and sortilin as used herein refer to a method of providing a ligand identified by the present invention said ligand being capable of preventing the binding of a proneurotrophin to binding site 3 of sortilin thus preventing formation of a ternary complex between sortilin, proNGF and p75$^{NTR}$ or any fragment or variant thereof. The term inhibiting binding may also refer to inhibiting binding of neurotensin and/or Sortilin propeptide to binding site 1 or 2 of the Vps10p-domain receptor Sortilin.

In vitro/in vivo: the terms are used in their normal meaning.

In silico: a method of performing an in vitro or in vivo operation by computer simulation.

Ischemia: Restriction in blood supply with resultant dysfunction or damage of tissue.

Ischemic tissue damage: Tissue damage due to ischemia.

Ligand: a substance or compound that is able to bind to and form a complex with a biomolecule to serve a biological purpose. In a narrower sense, it is a signal triggering molecule binding to a site on a target protein, by intermolecular forces such as ionic bonds, hydrogen bonds and Van der Waals forces. The docking (association) is usually reversible (dissociation). Actual irreversible covalent binding between a ligand and its target molecule is rare in biological systems. As opposed to the meaning in metalorganic and inorganic chemistry, it is irrelevant, whether or not the ligand actually binds at a metal site, as it is the case in hemoglobin. Ligand binding to receptors may alter the chemical conformation, i.e. the three dimensional shape of the receptor protein. The conformational state of a receptor protein determines the functional state of a receptor. The tendency or strength of binding is called affinity. Ligands include substrates, inhibitors, activators, and neurotransmitters. Radioligands are radioisotope labeled compounds and used in vivo as tracers in PET studies and for in vitro binding studies.

Moieties of a particular compound cover group(s) or part(s) of said particular compound.

Pharmaceutical agent: The terms "pharmaceutical agent" or "drug" or "medicament" refer to any therapeutic or prophylactic agent which may be used in the treatment (including the prevention, diagnosis, alleviation, or cure) of a malady, affliction, condition, disease or injury in a patient. Therapeutically useful genetic determinants, peptides, polypeptides and polynucleotides may be included within the meaning of the term pharmaceutical or drug. As defined herein, a "therapeutic agent," "pharmaceutical agent" or "drug" or "medicament" is a type of bioactive agent.

Pharmaceutical composition: or drug, medicament or agent refers to any chemical or biological material, compound, or composition capable of inducing a desired therapeutic effect when properly administered to a patient. Some drugs are sold in an inactive form that is converted in vivo into a metabolite with pharmaceutical activity. For purposes of the present invention, the terms "pharmaceutical composition" and "medicament" encompass both the inactive drug and the active metabolite.

Polypeptide: The term "polypeptide" as used herein refers to a molecule comprising at least two amino acids. The amino acids may be natural or synthetic. "Oligopeptides" are defined herein as being polypeptides of length not more than 100 amino acids. The term "polypeptide" is also intended to include proteins, i.e. functional biomolecules comprising at least one polypeptide; when comprising at least two polypeptides, these may form complexes, be covalently linked or may be non-covalently linked. The polypeptides in a protein can be glycosylated and/or lipidated and/or comprise prosthetic groups.

Polynucleotide: "Polynucleotide" as used herein refers to a molecule comprising at least two nucleic acids. The nucleic acids may be naturally occurring or modified, such as locked nucleic acids (LNA), or peptide nucleic acids (PNA). Polynucleotide as used herein generally pertains to
  i) a polynucleotide comprising a predetermined coding sequence, or
  ii) a polynucleotide encoding a predetermined amino acid sequence, or
  iii) a polynucleotide encoding a fragment of a polypeptide encoded by polynucleotides (i) or (ii), wherein said fragment has at least one predetermined activity as specified herein; and
  iv) a polynucleotide the complementary strand of which hybridizes under stringent conditions with a polynucleotide as defined in any one of (i), (ii) and (iii), and encodes a polypeptide, or a fragment thereof, having at least one predetermined activity as specified herein; and
  v) a polynucleotide comprising a nucleotide sequence which is degenerate to the nucleotide sequence of polynucleotides (iii) or (iv);
  or the complementary strand of such a polynucleotide.

Purified antibody: The term a "purified antibody" is an antibody at least 60 weight percent of which is free from the polypeptides and naturally-occurring organic molecules with which it is naturally associated. Preferably, the preparation comprises antibody in an amount of at least 75 weight percent, more preferably at least 90 weight percent, and most preferably at least 99 weight percent.

Preferably the antibody of the present invention is a rabbit anti-Sortilin antibody.

Root mean square deviation: The term "root mean square deviation" (rmsd) is used as a mean of comparing two closely related structures and relates to a deviation in the distance between related atoms of the two structures after structurally minimizing this distance in an alignment. Related proteins with closely related structures will be characterized by relatively low RMSD values whereas larger differences will result in an increase of the RMSD value.

Sequence identity: Sequence identity is determined in one embodiment by utilising fragments of a peptide or polypeptide based Vps10p domain antagonist comprising at least 25 contiguous amino acids and having an amino acid sequence which is at least 80%, such as 85%, for example 90%, such as 95%, for example 99% identical to the amino acid sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14 and SEQ ID NO: 15 respectively, wherein the percent identity is determined with the algorithm GAP, BESTFIT, or FASTA in the Wisconsin Genetics Software Package Release 7.0, using default gap weights.

The following terms are used to describe the sequence relationships between two or more polynucleotides: "predetermined sequence", "comparison window", "sequence identity", "percentage of sequence identity", and "substantial identity".

A "predetermined sequence" is a defined sequence used as a basis for a sequence comparison; a predetermined sequence may be a subset of a larger sequence, for example, as a segment of a full-length DNA or gene sequence given in a sequence listing, such as a polynucleotide sequence of SEQ ID NO:1, or may comprise a complete DNA or gene sequence. Generally, a predetermined sequence is at least 20 nucleotides in length, frequently at least 25 nucleotides in length, and often at least 50 nucleotides in length.

Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a predetermined sequence of at least 20 contiguous nucleotides and wherein the portion of the polynucleotide sequence in the comparison window may comprise additions or deletions (i.e., gaps) of 20 percent or less as compared to the predetermined sequence (which does not comprise additions or deletions) for optimal alignment of the two sequences.

Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a predetermined sequence over a comparison window of at least 20 nucleotide positions, frequently over a window of at least 25-50 nucleotides, wherein the percentage of sequence identity is calculated by comparing the predetermined sequence to the polynucleotide sequence which may include deletions or additions which total 20 percent or less of the predetermined sequence over the window of comparison. The predetermined sequence may be a subset of a larger sequence, for example, as a segment of the full-length SEQ ID NO:1 polynucleotide sequence illustrated herein.

As applied to polypeptides, a degree of identity of amino acid sequences is a function of the number of identical amino acids at positions shared by the amino acid sequences. A degree of homology or similarity of amino acid sequences is a function of the number of amino acids, i.e. structurally related, at positions shared by the amino acid sequences.

An "unrelated" or "non-homologous" sequence shares less than 40% identity, though preferably less than 25% identity, with a peptide or polypeptide based Vps10p domain antagonist of the present invention. The term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine, a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine.

Additionally, variants are also determined based on a predetermined number of conservative amino acid substitutions as defined herein below. Conservative amino acid substitution as used herein relates to the substitution of one amino acid (within a predetermined group of amino acids) for another amino acid (within the same group), wherein the amino acids exhibit similar or substantially similar characteristics.

Within the meaning of the term "conservative amino acid substitution" as applied herein, one amino acid may be substituted for another within the groups of amino acids indicated herein below:

i) Amino acids having polar side chains (Asp, Glu, Lys, Arg, His, Asn, Gln, Ser, Thr, Tyr, and Cys,)
ii) Amino acids having non-polar side chains (Gly, Ala, Val, Leu, Ile, Phe, Trp, Pro, and Met)
iii) Amino acids having aliphatic side chains (Gly, Ala Val, Leu, Ile)
iv) Amino acids having cyclic side chains (Phe, Tyr, Trp, His, Pro)
v) Amino acids having aromatic side chains (Phe, Tyr, Trp)
vi) Amino acids having acidic side chains (Asp, Glu)
vii) Amino acids having basic side chains (Lys, Arg, His)
viii) Amino acids having amide side chains (Asn, Gln)
ix) Amino acids having hydroxy side chains (Ser, Thr)
x) Amino acids having sulphur-containing side chains (Cys, Met),
xi) Neutral, weakly hydrophobic amino acids (Pro, Ala, Gly, Ser, Thr)
xii) Hydrophilic, acidic amino acids (Gln, Asn, Glu, Asp), and
xiii) Hydrophobic amino acids (Leu, Ile, Val)

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

The addition or deletion of at least one amino acid may be an addition or deletion of from preferably 2 to 250 amino acids, such as from 10 to 20 amino acids, for example from 20 to 30 amino acids, such as from 40 to 50 amino acids. However, additions or deletions of more than 50 amino acids, such as additions from 50 to 100 amino acids, addition of 100 to 150 amino acids, addition of 150-250 amino acids, are also comprised within the present invention. The deletion and/or the addition may—independently of one another—be a deletion and/or an addition within a sequence and/or at the end of a sequence.

siRNA: "small interfering RNA" (siRNA) is a short (often, but not restricted to, less than 30 nucleotides long) double-stranded RNA molecule capable of causing gene-specific silencing in mammalian cells.

Substituted lower alkyl means a lower alkyl having one to three substituents selected from the group consisting of hydroxyl, alkoxy, amino, amido, carboxyl, acyl, halogen, cyano, nitro and thiol.

Treatment: The term "treatment" as used herein refers to a method involving therapy including surgery of a clinical condition in an individual including a human or animal body. The therapy may be ameliorating, curative or prophylactic, i.e. reducing the risk of acquiring a disease.

Variants: The term "variants" as used herein refers to amino acid sequence variants said variants preferably having at least 60% identity, for example at least 63% identity, such as at least 66% identity, for example at least 70% sequence identity, for example at least 72% sequence identity, for example at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with any of the predetermined sequences. Variants of neurotensin include but not limited to artificial variants of neurotensin such as NT69L.

Up-regulation of expression: a process leading to increased expression of genes, preferably of endogenous genes.

Antagonist/Inhibitor to the Vps10p-Domain Receptor

In a main aspect the present invention relate to the use of at least one antagonist capable of binding to a receptor of the Vps10p-domain selected family thus inhibiting the activity of said Vps10p-domain receptor, in the manufacture of a medicament, for the treatment and/or prevention of abnormal plasma lipid concentrations in an animal.

In a main aspect the present invention relate to the use of at least one antagonist capable of binding to the Vps10p-domain receptor Sortilin (SEQ ID NO. 1) or a fragment or variant thereof, thus inhibiting the activity of said the Vps10p-domain receptor Sortilin (SEQ ID NO. 1), in the manufacture of a medicament, for the treatment and/or prevention of abnormal plasma lipid concentrations in an animal.

In a main aspect the present invention relate to the use of at least one antagonist capable of binding to the Vps10p-domain receptor SorLA (SEQ ID NO. 2) or a fragment or variant thereof, thus inhibiting the activity of said the Vps10p-domain receptor SorLA (SEQ ID NO. 2), in the manufacture of a medicament, for the treatment and/or prevention of abnormal plasma lipid concentrations in an animal.

In a main aspect the present invention relate to the use of at least one antagonist capable of binding to the Vps10p-domain receptor SorCS1 (SEQ ID NO. 3) or a fragment or variant thereof, thus inhibiting the activity of said the Vps10p-domain receptor SorCS1 (SEQ ID NO. 3), in the manufacture of a medicament, for the treatment and/or prevention of abnormal plasma lipid concentrations in an animal.

In a main aspect the present invention relate to the use of at least one antagonist capable of binding to the Vps10p-domain receptor SorCS2 (SEQ ID NO. 4) or a fragment or variant thereof, thus inhibiting the activity of said the Vps10p-domain receptor SorCS2 (SEQ ID NO. 4), in the manufacture of a medicament, for the treatment and/or prevention of abnormal plasma lipid concentrations in an animal.

In a main aspect the present invention relate to the use of at least one antagonist capable of binding to the Vps10p-domain receptor SorCS3 (SEQ ID NO. 5) or a fragment or variant thereof, thus inhibiting the activity of said the Vps10p-domain receptor SorCS3 (SEQ ID NO. 5), in the manufacture of a medicament, for the treatment and/or prevention of abnormal plasma lipid concentrations in an animal.

In a main aspect of the present invention the antagonist has the general structure of formula (I):

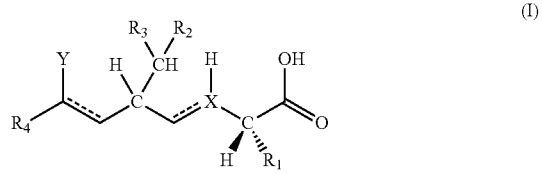

wherein X is an atom acting as hydrogen donor said atom selected from the group consisting of N, O, S, P and wherein Y is an electronegative atom acting as hydrogen bond acceptor selected from the group consisting of O, N, S, F, Cl, Br, I, and wherein $R_1$ is C3-6 alkyl, C4-6 cyclyl, a heterocyclic or a heteroaromatic structure having one ring, 4 to 6 ring members in each and 1 to 3 heteroatoms, or a heteroalkyl comprising 1 to 3 heteroatoms selected from the group consisting of N, O, $S(O)_{0-2}$, and wherein $R_2$ is a hydrogen, a C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, $S(O)_{0-2}$, and wherein $R_3$ is hydrogen, SH, imidazole, C1-12 alkyl or an aromatic, a carbocyclic, a heterocyclic or a heteroaromatic structure having 1-3 rings, 3-8 ring members in each and 0 to 4 heteroatoms, or a heteroalkyl comprising 1 to 8 heteroatoms selected from the group consisting of N, O, S, and wherein $R_4$ is selected from the functional groups C1-100 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), thiocyanate, disulfide, a linker L2 or L3, and an amino acid sequence being at least 50% identical to SEQ ID NO: 10 or a fragment thereof.

The antagonist of formula (I) is specific for binding site 1 (high affinity Neurotensin binding site) of Sortilin.

In another main aspect the antagonist has the general structure of formula (II):

$$\text{(II)}$$

[Structure of formula (II) showing peptide backbone with R$_{10}$, R$_9$, R$_8$, R$_7$, R$_6$, R$_5$, and Z substituents]

wherein Z is a hydrogen bond donor or acceptor selected from the group consisting of carbonyl, hydroxyl, amino, imino, amide, sulfhydryl, chloro, fluoro, and wherein $R_5$ is selected from the group consisting of H, CH$_3$, and a linker L2, and wherein $R_6$ is selected from the group consisting of H, —CH$_3$, —CH$_2$CH$_3$ and —OCH$_3$, and wherein $R_7$ is selected from the group consisting of side chains of glutamate, glutamine, lysine, arginine, histidine, tyrosine, methionine, cysteine, aliphatic C4-6 groups, and wherein $R_8$ is selected from the group consisting of side chains of tyrosine, histidine, serine, threonine, aspartate, asparagine, cysteine, phenylalanine, iodo-tyrosine and —CH$_2$—NH$_2$, and wherein $R_9$ is selected from the group consisting of side chain of lysine, arginine, glutamine, C3-8 aliphatic and heteroaliphatic groups, carbocyclic and heterocyclic groups comprising 5 or 6 membered rings, and wherein $R_{10}$ is selected from the group consisting of a pyroglutamate, poly-carbohydrates and a polypeptide of length greater than equal to 10, and wherein $R_{11}$ and $R_{12}$ individually are selected from the group consisting of H, C1-12 linear or branched alkyl, linear or branched alkenyl, linear or branched alkynyl, phenyl, benzyl, haloalkane, chloroalkane, bromoalkane, iodoalkane, haloformyl, hydroxyl, carbonyl, aldehyde, carbonate ester, carboxylate, carboxyl, ether, ester, hydroperoxy, peroxy, carboxamide, primary amine, secondary amine, tertiary amine, ammonium, primary ketimine, secondary ketimine, primary aldimine, secondary aldimine, imide, azide, azo (diimide), cyanate, isocyanide, isothiocyanate, nitrate, nitrile, nitrosooxy, nitro, nitroso, priidyl, phosphino, phosphate, phosphono, sulfonyl, sulfinyl, sulfhydryl (SH), and wherein the covalent bonds (1) and (2) individually are selected from the group consisting of single bonds and double bonds.

The antagonist of formula (II) is specific for binding site 2 (low affinity Neurotensin binding site) of Sortilin.

In another main aspect the antagonist has the general structure of formula (III):

$$\text{(III)}$$

[Structure of formula (III) showing peptide backbone with R$_{18}$, R$_{17}$, R$_{16}$, R$_{15}$, R$_{14}$, R$_{13}$ substituents]

wherein $R_{13}$ is selected from the group consisting of H, C1-12 alkyl, alkenyl, alkynyl and a linker L3, and wherein $R_{14}$, $R_{15}$, $R_{17}$, $R_{19}$, $R_{20}$ individually are selected from the group consisting of H, C1-12 alkyl, alkenyl and alkynyl, and wherein $R_{16}$ is selected from the group consisting of sidechains of phenylalanine, leucine, isoleucine, valine, methionine, histidine, cysteine, lysine and aliphatic C3-7, and wherein $R_{18}$ is selected from the group consisting of H, —CH$_3$ and —CH$_2$OH, and wherein the covalent bonds (1) and (2) individually are selected from the group consisting of single bonds and double bonds.

The antagonist of formula (I) or (II), wherein the linker L2 is selected from the group consisting of a peptide backbone of 5 to 6 residues, C15-20 alkyl, C15-20 alkenyl and C15-20 alkynyl.

The antagonist of formula (III) is specific for binding site 3 (proneurotrophin binding site) of Sortilin.

In one embodiment the antagonist of formula (I) is linked to the antagonist of formula (II) by a linker L2, thereby forming the general formula (IV):

[Formula (I)]–[Linker L2]–[Formula (II)]    (IV)

In one embodiment the linker L3 is selected from the group consisting of a peptide backbone of 12 to 20 residues, C30-60 alkyl, C30-60 alkenyl, C30-60 alkynyl.

The antagonist of formula (I) linked to the antagonist of formula (III) by the linker L3, thereby forming the general formula (V):

[Formula (I)]–[Linker L3]–[Formula (III)]    (V)

The antagonist as defined herein above wherein said antagonist is selected from the group consisting of RRPYI (chg), iodoYIL, QIL, YCL, dYIL, YHL, RRPYI(acc), RRPYI (nMe)L, YIL depicted in FIG. 10.

The antagonist as defined herein above wherein said antagonist is RRPYI(chg) depicted in FIG. 10.

The antagonist as defined herein above wherein said antagonist is iodoYIL depicted in FIG. 10.

The antagonist as defined herein above wherein said antagonist is QIL depicted in FIG. 10.

The antagonist as defined herein above wherein said antagonist is YCL depicted in FIG. 10.

The antagonist as defined herein above wherein said antagonist is dYIL depicted in FIG. 10.

The antagonist as defined herein above wherein said antagonist is YHL depicted in FIG. 10.

The antagonist as defined herein above wherein said antagonist is RRPYI(acc) depicted in FIG. 10.

The antagonist as defined herein above wherein said antagonist is RRPYI(nMe)L depicted in FIG. 10.

The antagonist as defined herein above wherein said antagonist is YIL depicted in FIG. 10.

In one embodiment of the present invention the animal is a human being (*Homo Sapiens Sapiens*).

In one embodiment of the present invention the animal is selected from the group consisting of mouse, rat, rabbit, canine and dog.

Indications

In one embodiment of the present invention the abnormal plasma lipid concentration is hyperlipoproteinemia.

In one embodiment of the present invention the hyperlipoproteinemia is selected from the group consisting of Types I, IIa, IIb, III, IV or V hyperlipoproteinemia.

In a further embodiment of the present invention the Type I hyperlipoproteinemia is selected from the group consisting of Buerger-Gruetz syndrome, Primary hyperlipoproteinaemia, or Familial hyperchylomicronemia.

In a further embodiment of the present invention the Type IIa hyperlipoproteinemia is selected from the group consisting of Polygenic hypercholesterolemia or Familial hypercholesterolemia.

In a further embodiment of the present invention the Type IIb hyperlipoproteinemia is Combined hyperlipidemia.

In a further embodiment of the present invention the Type III hyperlipoproteinemia is Familial Dysbetalipoproteinemia.

In a further embodiment of the present invention the Type IV hyperlipoproteinemia is Endogenous Hyperlipemia.

In a further embodiment of the present invention the Type V hyperlipoproteinemia is Familial Hypertriglyceridemia.

In a further embodiment of the present invention the hyperlipoproteinemia effect a disease or disorder selected from the group consisting of Aneurysm, Angina pectoris, Atherosclerosis, Cerebrovascular Accident (Stroke), Cerebrovascular disease, Congenital heart disease, Congestive Heart Failure, Coronary Artery Disease, Dilated cardiomyopathy, Diastolic dysfunction, Endocarditis, Hypercholesterolemia, Hypertension, Hyperlipidemia, Hypertrophic cardiomyopathy, Mitral valve prolapse, Myocardial infarction (Heart Attack) and Venous Thromboembolism, in an animal.

In a further embodiment of the present invention the Vps10p-domain receptor comprises an amino acid sequence having at least 60% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 65% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 70% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 75% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 80% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 85% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 90% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 91% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 92% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 93% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 94% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 95% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 96% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 97% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 98% sequence identity to SEQ ID NO. 1, SEQ ID NO. 2, SEQ ID NO. 3, SEQ ID NO. 4 or SEQ ID NO. 5. In a further embodiment of the present invention the Vps10p-domain receptor comprises an amino acid sequence having at least 99% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 99.5% sequence identity to SEQ ID NO. 1, SEQ ID NO. 2, SEQ ID NO. 3, SEQ ID NO. 4 or SEQ ID NO. 5.

In a further embodiment of the present invention the Vps10p-domain receptor comprises an amino acid sequence having at least 99.9% sequence identity to SEQ ID NO. 1, SEQ ID NO. 2, SEQ ID NO. 3, SEQ ID NO. 4 or SEQ ID NO. 5.

In one embodiment of the present invention the at least one antagonist as defined herein is capable of inhibiting binding of an agonist selected from the group consisting of SEQ ID NO. 6 (proNGF), SEQ ID NO. 7 (proBDNF), SEQ ID NO. 8 (proNT3), SEQ ID NO. 9 (pro-NT4/5), SEQ ID NO. 14 (ApoE) or SEQ ID NO. 15 (LpL) or a fragment or variant thereof, to said Vps10p-domain receptor.

In another embodiment of the present invention the at least one antagonist as defined herein above is bound to at least one amino acid residue of the binding site comprising amino acid residues R325, S316, Y351, I353, K260, I327, F314, F350 to M363, S305, F306, T398 to G400, I303-G309, Q349-A356, Y395 and T402 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In yet another embodiment of the present invention the at least one antagonist as defined herein above is bound to at least one amino acid residue of the binding site comprising amino acid residues R325, S316, Y351, I353, K260, I327, F314, F350 to M363, S305, F306 and T398 to G400 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In yet another embodiment of the present invention the at least one antagonist as defined herein above is bound to at least one amino acid residue of the binding site comprising amino acid residues R325, S316, Y351, I353, K260, I327, F314 and F350 to M363 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In yet another embodiment of the present invention the at least one antagonist as defined herein above is bound to at least one amino acid residue of the binding site comprising amino acid residues L572, L114, V112, R109 to S111, S115 to G118, T570, G571, W586, W597, T168-I174, L572, A573 and S584 to F588 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In yet another embodiment of the present invention the at least one antagonist as defined herein above is bound to at least one amino acid residue of the binding site comprising amino acid residues L572, L114, V112, R109 to S111, S115 to G118, T570, G571, W586 and W597 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In yet another embodiment of the present invention the at least one antagonist as defined herein above is bound to at least one amino acid residue of the binding site comprising amino acid residues L572, L114 and V112 of SEQ ID NO. 1

(Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In an important embodiment of the present invention the at least one antagonist as defined herein above is bound to at least one amino acid residue of the binding site comprising amino acid residues D403, S420, D422, N423, S424, I425, Q426, E444, T451, Y466, E470, I498, S499 and V500 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In a preferred embodiment of the present invention the at least one antagonist as defined herein above is bound to at least one amino acid residue of the binding site comprising amino acid residues D403, N423, S424, I425, E444, T451, Y466, I498 and V500 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

In a highly preferred embodiment of the present invention the at least one antagonist as defined herein above is bound to at least one amino acid residue of the binding site comprising amino acid residues E444, T451, Y466, I498 and V500 of SEQ ID NO. 1 (Sortilin) or a fragment or variant thereof wherein the fragment is selected from, but not limited to the group comprising soluble Sortilin, pro-Sortilin and mature Sortilin and the variant is selected from, but not limited to the group comprising a sequence having at least 60% sequence identity to SEQ ID NO. 1, or any of the fragments soluble Sortilin, pro-Sortilin and mature Sortilin and a sequence having at least 65% sequence identity to SEQ ID NO. 1, or any of the fragments soluble Sortilin, pro-Sortilin and mature Sortilin and a sequence having at least 70% sequence identity to SEQ ID NO. 1, or any of the fragments soluble Sortilin, pro-Sortilin and mature Sortilin and a sequence having at least 75% sequence identity to SEQ ID NO. 1, or any of the fragments soluble Sortilin, pro-Sortilin and mature Sortilin and a sequence having at least 80% sequence identity to SEQ ID NO. 1, or any of the fragments soluble Sortilin, pro-Sortilin and mature Sortilin and a sequence having at least 85% sequence identity to SEQ ID NO. 1, or any of the fragments soluble Sortilin, pro-Sortilin and mature Sortilin a sequence having at least 90% sequence identity to SEQ ID NO. 1, or any of the fragments soluble Sortilin, pro-Sortilin and mature Sortilin a sequence having at least 95% sequence identity to SEQ ID NO. 1, or any of the fragments soluble Sortilin, pro-Sortilin and mature Sortilin and a sequence having at least 99% sequence identity to SEQ ID NO. 1, or any of the fragments soluble Sortilin, pro-Sortilin and mature Sortilin.

The antagonist which in this sense is synonymous with an inhibitor to the Vps10p-domain receptor is selected from but not limited to the group comprising proteins, peptides, polypeptides, antibodies, antisense RNA, antisense-DNA, small organic molecules and siRNA.

Antibodies Against Vps10p-Domain Receptor

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Conceptually, antibodies directed against a target receptor may inhibit ligand binding in two ways: competitive or allosteric. Competitive inhibition involves the direct binding of the antibody to or near the ligand binding site on the receptor, thereby displacing the ligand from its receptor or sterically inhibiting the approach of the ligand to the ligand binding site. Allosteric inhibition involves the binding of the antibody to a site on the receptor polypeptide that is distinct from the ligand binding epitope. However, binding to this site will induce a conformational change in the overall structure of the receptor that makes it more difficult or even impossible for the ligand to bind to its cognate recognition site.

The inventors of this application have raised antibodies against several parts of the Vps10p-domain receptors. The present invention is directed to antibodies against the unifying feature of this receptor family—the Vps10p domain. The below sequence alignment of the Vps10p-domain demonstrate the conservation within this receptor family.

TABLE 2

Antibodies against Vps10p-domain receptors

| Receptor | Name | Antigen | Species | Western | IH/IC | Ref. |
|---|---|---|---|---|---|---|
| SorLA | SORLA goat | extracellular domain | goat | X | X | Schmidt et. al., J. Biol. Chem. 282: 32956-67, 2007 |
| | Hale SORLA | Cytoplasmic domain | rabbit | X | | |
| | SORLA LA | Complement type repeat | rabbit | X | | |
| | Sol SORLA | extracellular domain | rabbit | X | X | Andersen et al., PNAS 103: 13461-6, 2005 |
| | SORLA tail | Cytoplasmic domain | rabbit | X | | |
| | SORLA VPS | VPS10p domain | rabbit | X | | |
| | #606870 | Peptide seq. in Vps10p-domain | rabbit | X | | |
| | #642739 | C-terminal | rabbit | X | | |
| | #643739 | Cytoplasmic tail | rabbit | X | | |
| | 20C11 | Extracellular domain | mouse | X | X | |
| | AG4 | Extracellular domain | mouse | X | | |
| Sortilin | #5264 | Extracellular domain | rabbit | X | X | Munck Petersen et al, EMBO J. 18: 595-604, 1999 |
| | #5448 | Cytoplasmic domain | rabbit | X | X | Jansen et al, Nature Neurosci. 10: 1449-1457, 2007 |
| | #5287 | Cytoplasmic domain | rabbit | X | | |
| | CP 96 334 SR 96 204 | propeptide | Rabbit | X | | Munck Petersen et al, EMBO J. 18: 595-604, 1999 |
| | #5438 | Vps10p | rabbit | X | | |
| | Sortilin goat/Laika | Extracellular domain | goat | X | | |
| | F9 | Extracellular domain | mouse | X | X | |
| | F11 | Extracellular domain | mouse | X | X | |
| | AF2934 | Extracellular domain | goat | X | X | R&D Systems, Jansen et al, Nature Neurosci. 10: 1449-1457, 2007 |
| | AF3154 | Extracellular domain | goat | X | X | R&D Systems; Jansen et al, Nature Neurosci. 10: 1449-1457, 2007 |

TABLE 2-continued

Antibodies against Vps10p-domain receptors

| Receptor | Name | Antigen | Species | Western | IH/IC | Ref. |
|---|---|---|---|---|---|---|
| | anti-NTR3 | Extracellular domain | mouse | X | X | BD Transduction Laboratories, |
| | ANT-009 | Extracellular domain | mouse | X | X | Alomone Labs; Nykjaer et al, Nature 427: 843-848, 2004 |
| SorCS1 | AF3457 | Extracellular domain | goat | X | X | BD Transduction Laboratories |
| | SorCS1 goat | Extracellular domain | goat | X | | |
| | L-SorCS1 | Extracellular domain | rabbit | X | X | Hermey et al, J. Biol. Chem. 279: 50221-50229, 2003 |
| | Leu-SorCS1 | Leucine-rich domain | rabbit | X | X | Hermey et al, J. Biol. Chem. 279: 50221-50229, 2003 |
| | #5466 | Extracellular domain | rabbit | X | X | |
| | 1D | Extracellular domain | mouse | X | | |
| | 4H | Extracellular domain | mouse | X | | |
| | 6B | Extracellular domain | mouse | X | | |
| | 4A | Extracellular domain | mouse | X | | |
| SorCS2 | AF4237 | Extracellular domain | sheep | X | | BD Transduction Laboratories |
| | SorCS2 goat | Extracellular domain | goat | X | X | |
| | #5422 | Extracellular domain | rabbit | X | X | Hermey et al, Biochem. J., 395: 285-93, 2006 |
| | #5431 | 28 C-terminal amino acids | rabbit | X | X | |
| | SorCS2-prp | propeptide | rabbit | X | | Schousboe Sjoegaard, Dissertation, Aarhus University, 2005 |
| | M1 | Extracellular domain | mouse | | X | Roland Holst, Master of Science Thesis, Aarhus University, 2006 |
| | M3 | Extracellular domain | mouse | | X | Roland Holst, Master of Science Thesis, Aarhus University, 2006 |
| | M4 | Extracellular domain | mouse | | X | Roland Holst, Master of Science Thesis, Aarhus University, 2006 |
| | M7 | Extracellular domain | mouse | | X | Roland Holst, Master of Science Thesis, Aarhus University, 2006 |
| | M9 | Extracellular domain | mouse | | X | Roland Holst, Master of Science Thesis, Aarhus University, |

TABLE 2-continued

Antibodies against Vps10p-domain receptors

| Receptor | Name | Antigen | Species | Western | IH/IC | Ref. |
|---|---|---|---|---|---|---|
| | M10 | Extracellular domain | mouse | | X | Roland Holst, Master of Science Thesis, Aarhus University, 2006 |
| | M13 | Extracellular domain | mouse | X | | Roland Holst, Master of Science Thesis, Aarhus University, 2006 |
| | M15 | Extracellular domain | mouse | | X | Roland Holst, Master of Science Thesis, Aarhus University, 2006 |
| | M18 | Extracellular domain | mouse | X | X | Roland Holst, Master of Science Thesis, Aarhus University, 2006 |
| | M19 | Extracellular domain | mouse | X | X | Roland Holst, Master of Science Thesis, Aarhus University, 2006 |
| | S21 | Extracellular domain | mouse | X | | Roland Holst, Master of Science Thesis, Aarhus University, 2006 |
| | SorCS2-GST-73aa | Extracellular domain | rabbit | X | | |
| | SorCS2-GST-100aa | Extracellular domain | rabbit | X | | |
| | SorCS2-GST-172aa | Extracellular domain | rabbit | X | | |
| SorCS3 | SorCS3-N | extracellular domain | rabbit | X | | |
| | SorCS3-C | 15 C-terminal aa | rabbit | X | | |
| | Sort3 N Term #5389 | N-terminal domain | rabbit | X | X | Westergaard et al, FEBS Lett. 579: 1172-6, 2005 |
| | #5432 | Extracellular domain | rabbit | X | X | |
| | MAB3067 | Extracellular domain | mouse | X | | BD Transduction Laboratories |
| | MAB30671 | Extracellular domain | mouse | X | | BD Transduction Laboratories |
| | AF3326 | Extracellular domain | goat | X | | BD Transduction Laboratories |
| | SorCS3 goat | Extracellular domain | goat | X | | |

Generic Use of an Antibody to Inhibit Binding of a Ligand

An antibody binds tightly to a particular target molecule, thereby either inactivating it directly or marking it for destruction. The antibody recognizes its target (antigen) with remarkable specificity and strength dictated by the sum of many chemical forces, including hydrogen bonds, hydrophobic and van der Waal's forces, as well as ionic interactions. In general, the more complex the target is chemically, the more immunogenic it will be. The antigenic determinant may encompass short linear amino acid stretches or a more complicated, three-dimensional protein module.

Procedures for Making Antibodies

Polyclonal and monoclonal antibodies directed against a specific antigen, or epitope of an antigen, can be produced according to standard procedures (see e.g. Antibodies—A laboratory Manual by Ed Harlow and David Lane, Cold Spring Harbor Laboratory 1998, ISBN 0-87969-314-2). The procedure for subsequent generation of humanized antibodies or fragments thereof has also been described (e.g. A. M. Scott et al, Cancer Research 60:3254-3261, 2000; A. Nissim and Y. Chemajovsky, Handb. Exp. Pharmacol. 181:3-18, 2008; A. Mountain and J. R. Adair, Biotechnol. Genet. Eng. Rev. 10:1-142, 1992).

General Expectations of Success in Making Antibodies

It is possible to generate antibodies against any peptide motif of choice using short synthetic oligopeptides that encompass the desired target epitope. Therefore, it is guaranteed that antibodies against ligand binding sites on receptors can be generated. Whether or not individual antibody species have the potential to inhibit ligand binding simply depends on the fact that the affinity of the immunoglobulin for the receptor exceeds that of the ligand. In the end, it is a matter of screening the inhibitory potential of a number of individual antibodies to find one with the desired properties.

Screening assays for inhibitory antibodies are common knowledge and typically involve a competitive enzyme linked immunosorbent assay (ELISA). In detail, the recombinant receptor or a fragment encompassing its ligand binding motif are immobilized in replicate wells of microtiter plates. Subsequently, the wells are incubated with a solution containing the ligand. Binding of the ligand to the immobilized receptor is confirmed using an antibody that recognizes the ligand and that is coupled with a color dye reaction. Binding of the ligand to the receptor is tested in the presence of various antibodies to identify those immunoglobulin species that block ligand binding to the receptor and hence prevent color reaction in the respective microtiter plate well.

Successful Clinical Use of Antibodies

A number of therapeutic antibodies are in clinical use. Examples include Genentech's Rituxan, an antibody directed against the CD20 receptor (used in rheumatoid arthritis), Johnson & Johnson's Remicade, an antibody directed against TNF alpha receptor (in Psoriasis), Roche's Avastin, an anti-VEGF antibody used for treatment of colorectal and lung cancer, as well as Herceptin, an antibody against the receptor HRE2 used in breast cancer therapy.

Assessing binding to a receptor is routine work for the person skilled in the biotechnical field. In this regard it has to be mentioned that pro-neurotrophins as well as the Vps10p-domain receptor family were known at the priority date of this invention and binding assays involving for example pro-neurotrophins has been mentioned in the prior art, for example in the article by Lee et al (2001) Science 294:1945-1948.

Accordingly, in an important embodiment the antagonist of the present invention is an antibody.

In a further embodiment the antibody is directed against an extracellular part of the Vps10p-domain receptor.

In a further embodiment the antibody is directed against an intracellular part of the Vps10p-domain receptor.

In a further embodiment the antibody is directed against an a transmembrane part of the Vps10p-domain receptor.

In one embodiment of the present invention the antibody as defined herein above is selected from the group consisting of: polyclonal antibodies, monoclonal antibodies, humanised antibodies, single chain antibodies, recombinant antibodies.

In another aspect, the invention relate to the use of at least one antagonist capable of binding to at least one amino acid residue of a Vps10p-domain receptor agonist selected from the group consisting of SEQ ID NOs. 6, 7, 8, 9, 10, 14 or 15 or a fragment or variant thereof, in the manufacture of a medicament, for the treatment and/or prevention of abnormal plasma lipid concentrations in an animal.

In aspect the present invention relates to an immunoconjugate comprising the antibody as defined herein above and a conjugate selected from the group consisting of: a cytotoxic agent such as a chemotherapeutic agent, a toxin, or a radioactive isotope; a member of a specific binding pair, such as avidin or streptavidin or an antigen.

Methods of Screening for Antagonists/Inhibitors of Vps10p-Domain Receptors

The present invention also relate to in vitro and in vivo methods of identifying an antagonist of a Vps10p-domain receptor, said antagonist being capable of binding to said Vps10p-domain receptor and thus inhibit binding of an endogenous agonist to said receptor, consequently preventing/inhibiting a physiological response associated with regulation of blood plasma lipid concentrations.

Accordingly, in one aspect, the invention concerns an in vitro method for screening for an antagonist capable of binding to a Vps10p-domain receptor, comprising the steps of:
 a) providing a Vps10p-domain receptor, and
 b) providing an agonist,
 c) providing a library of potential antagonists, and
 d) providing an assay for measuring the binding of an agonist to a Vps10p-domain receptor, and
 e) adding the library of potential antagonists to be tested to the assay, and
 f) determining the amount of agonist bound to the Vps10p-domain receptor, and
 g) comparing the amount determined in step f) with an amount measured in the absence of the antagonist to be tested,
 h) wherein the difference in the two amounts identifies an antagonist which alters the binding of the agonist to the Vps10p-domain receptor.

In yet another aspect the present invention relates to a method for determining the degree of inhibition of an antagonist on activity of a Vps10p-domain receptor in a cell culture expressing said receptor, wherein said Vps10p-domain receptor comprises an amino acid sequence having at least 60% sequence identity to SEQ ID NO. 1, SEQ ID NO. 2, SEQ ID NO. 3, SEQ ID NO. 4 or SEQ ID NO. 5, said method comprising the steps of:
 a) providing a cell culture expressing a Vps10p-domain receptor, and
 b) providing an agonist of the Vps10p-domain receptor, and
 c) providing a library of potential antagonists, and
 d) providing an assay for determination of binding to, internalisation of and signalling through, a Vps10p-domain receptor, said assay comprising
 e) adding the library of potential antagonists to be tested c) to the cell culture a), in the presence of the agonist b), and
 f) determining
  i) the amount of antagonist bound to the Vps10p-domain receptor, and/or
  ii) the amount of antagonist internalised by the Vps10p-domain receptor, and/or
  iii) the degree of signalling through the Vps10p-domain receptor, and
 g) comparing the amount determined in step f) with an amount measured in the absence of the antagonist to be tested,
 h) wherein the difference in the two amounts identifies an antagonist
  i) capable of binding to a Vps10p-domain receptor, and/or
  ii) capable of inhibiting signalling through a Vps10p-domain receptor, and/or
  iii) capable of inhibiting internalisation of an agonist of said Vps10p-domain receptor.

In a further aspect the present invention relates to a method for determining the degree of inhibition of an antagonist on activity of a Vps10p-domain receptor in a cell culture expressing said receptor and with the a cell culture lacking expression of said receptor, said method comprising the steps of:
  a) providing a cell culture expressing a Vps10p-domain receptor, and
  b) providing a cell culture not expressing a Vps10p-domain receptor, and
  c) optionally providing a cell culture overexpressing a Vps10p-domain receptor
  d) providing an agonist of the Vps10p-domain receptor, and
  e) providing a library of potential antagonists, and
  f) providing a first assay comprising a) and a second assay comprising b) and optionally a third assay comprising c), and
  g) adding the library of potential antagonists to be tested to the three assays, and
  h) determining
    i) the amount of antagonist bound to the Vps10p-domain receptor, and/or
    ii) the amount of antagonist internalised by the Vps10p-domain receptor, and/or
    iii) the degree of signalling through the Vps10p-domain receptor, and
  i) comparing the amount of antagonist determined in step g) using a) with the amount determined in g) using b) and the amount determined in g) using c),
  j) wherein the difference in the amounts identifies an antagonist
    i) capable of binding to a Vps10p-domain receptor, and/or
    ii) capable of inhibiting signalling through a Vps10p-domain receptor, and/or
    iii) capable of inhibiting internalisation of an agonist of said Vps10p-domain receptor.

In a further embodiment the agonist as defined herein above is selected from the group consisting of SEQ ID NO. 6 (proNGF), SEQ ID NO. 7 (proBDNF), SEQ ID NO. 8 (proNT3), SEQ ID NO. 9 (pro-NT4/5), SEQ ID NO. 14 (ApoE) or SEQ ID NO. 15 (LpL) or a fragment or variant thereof.

In a further aspect the present invention relates to a method for determining the degree of inhibition of an antagonist on activity of a Vps10p-domain receptor in a mammal expressing said receptor, said method comprising the steps of:
  a) administering said antagonist to a mammal naturally expressing the receptor,
  b) determining
    i) the amount of antagonist bound to the Vps10p-domain receptor, and/or
    ii) the amount of antagonist internalised by the Vps10p-domain receptor, and/or
    iii) the degree of signalling through the Vps10p-domain receptor, and
  c) comparing the measurement of step b) with a measurement obtained in the absence of the compound to be tested,
  d) wherein the difference in the two measurements identifies the effect of said antagonist on said mammal naturally expressing the receptor.

In yet another aspect the present invention relate to a method for determining the degree of inhibition of an antagonist on activity of a Vps10p-domain receptor in a mammal expressing said receptor with a second mammal, lacking expression of said receptor and a third mammal overexpressing said receptor, said method comprising the steps of:
  a) providing a mammal expressing a Vps10p-domain receptor, and
  b) providing a mammal not expressing a Vps10p-domain receptor, and
  c) providing a mammal overexpressing a Vps10p-domain receptor, and
  d) providing an agonist of the Vps10p-domain receptor, and
  e) providing a library of potential antagonists, and
  f) administering said library of antagonists to said mammal of a), b) and c) respectively, and
  g) determining
    i) the amount of antagonist bound to the Vps10p-domain receptor, and/or
    ii) the amount of antagonist internalised by the Vps10p-domain receptor, and/or
    iii) the degree of signalling through the Vps10p-domain receptor, in each of the mammals defined in a), b) and c), and
  h) comparing the amount of antagonist determined in step g) using a) with the amount determined in g) using b) with the amount determined in g) using c),
    i) wherein the difference in the amounts identifies an antagonist
      i) capable of binding to a Vps10p-domain receptor, and/or
      ii) capable of inhibiting signalling through a Vps10p-domain receptor, and/or
      iii) capable of inhibiting internalisation of an agonist of said Vps10p-domain receptor.

Pharmaceutical Composition

In a further aspect the present invention relates to a pharmaceutical composition comprising the antagonist of claim 1, said antagonist selected from the group consisting of small organic compounds, oligo-peptides, proteins and monoclonal or polyclonal antibodies.

The pharmaceutical composition according to claim 36 wherein said antagonist is an antagonist of a Vps10p-domain as defined in claim 2.

In a further embodiment the pharmaceutical composition as defined herein above comprises a pharmaceutically acceptable carrier.

In a further embodiment the pharmaceutical composition as defined herein above comprises a second active ingredient selected from but not limited to the group consisting of analgesics, opiods, adrenergic antagonists, antihypertensives and compounds capable of modulating plasma lipid concentrations.

In an important embodiment the compound capable of modulating plasma lipid concentrations is a statin selected from the group consisting of Atorvastatin, Cerivastatin, Fluvastatin, Lovastatin, Mevastatin, Pitavastatin, Pravastatin, Rosuvastatin, Simvastatin, Simvastatin/Ezetimibe combination, Lovastatin/Niacin combination and Atorvastatin/Amlodipine Besylate Caduet combination.

In a further embodiment the pH of the pharmaceutical composition defined herein above is between pH 5 and pH 9.

In an important aspect the present invention relate to the use of the pharmaceutical composition described herein above for the preparation of a medicament for the treatment or prevention of a disease or disorder associated with abnormal plasma lipid concentrations.

Method of Treatment

In one aspect the present invention relates to a method of treatment of a pathological condition of the cardiovascular system associated with abnormal plasma lipid concentrations in a subject comprising administering to an individual in need thereof a therapeutically effective amount of the pharmaceutical composition defined herein above.

In one embodiment of the present invention the abnormal plasma lipid concentration as defined herein above is abnormal concentrations of LDL-cholesterol In a further embodiment of the present invention the abnormal plasma lipid concentration as defined herein above is abnormal concentrations of triglycerides.

Kit of Parts

In one aspect the present invention relates to a kit in parts comprising:
 a pharmaceutical composition as defined herein above,
 a medical instrument or other means for administering the medicament,
 instructions on how to use the kit in parts.

In one embodiment the kit in parts as defined herein above comprises a second active ingredient.

In a further aspect the present invention relates to the use at least one antagonist wherein said antagonist is capable of inhibiting expression of a Vps10p-domain receptor in an animal.

Administration Forms

The main routes of drug delivery, in the treatment method are intravenous, oral, and topical. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compounds of the invention may be administered parenterally, that is by intravenous, intramuscular, subcutaneous intranasal, intrarectal, intravaginal or intraperitoneat administration. The subcutaneous and intramuscular forms of parenteral administration are generally preferred. Appropriate dosage forms for such administration may be prepared by conventional techniques. The compounds may also be administered by inhalation, which is by intranasal and oral inhalation administration. Appropriate dosage forms for such administration, such as an aerosol formulation or a metered dose inhaler, may be prepared by conventional techniques.

The compounds according to the invention may be administered with at least one other compound. The compounds may be administered simultaneously, either as separate formulations or combined in a unit dosage form, or administered sequentially.

Formulations

Whilst it is possible for the compounds or salts of the present invention to be administered as the raw chemical, it is preferred to present them in the form of a pharmaceutical formulation. Accordingly, the present invention further provides a pharmaceutical formulation, for medicinal application, which comprises a compound of the present invention or a pharmaceutically acceptable salt thereof, as herein defined, and a pharmaceutically acceptable carrier therefore.

The compounds of the present invention may be formulated in a wide variety of oral administration dosage forms. The pharmaceutical compositions and dosage forms may comprise the compounds of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, wetting agents, tablet disintegrating agents, or an encapsulating material.

Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. Powders and tablets preferably contain from one to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Drops according to the present invention may comprise sterile or non-sterile aqueous or oil solutions or suspensions, and may be prepared by dissolving the active ingredient in a suitable aqueous solution, optionally including a bactericidal and/or fungicidal agent and/or any other suitable preservative, and optionally including a surface active agent. The resulting solution may then be clarified by filtration, transferred to a suitable container which is then sealed and sterilized by autoclaving or maintaining at 98-100° C. for half an hour. Alternatively, the solution may be sterilized by filtration and transferred to the container aseptically. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, solubilizing agents, and the like.

Other forms suitable for oral administration include liquid form preparations including emulsions, syrups, elixirs, aqueous solutions, aqueous suspensions, toothpaste, gel dentifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by dissolving the active component in water and adding suitable colorants, flavours, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilizing agents, and the like.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compounds of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or nonionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active compound may be formulated into a suppository comprising, for example, about 0.5% to about 50% of a compound of the invention, disposed in a polyethylene glycol (PEG) carrier (e.g., PEG 1000 [96%] and PEG 4000 [4%].

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compounds of the present invention may be formulated for aerosol administration, particularly to the respiratory tract and including intranasal administration. The compound will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compounds, where they can be prepared, are also intended to be covered by this invention. These salts will be ones which are acceptable in their application to a pharmaceutical use. By that it is meant that the salt will retain the biological activity of the parent compound and the salt will not have untoward or deleterious effects in its application and use in treating diseases.

Pharmaceutically acceptable salts are prepared in a standard manner. If the parent compound is a base it is treated with an excess of an organic or inorganic acid in a suitable solvent. If the parent compound is an acid, it is treated with an inorganic or organic base in a suitable solvent.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

In one embodiment the pharmaceutical composition as desfined herein above is formulated for administration by injection, suppository, oral administration, sublingual tablet or spray, cutaneous administration, inhalation or for local administration using an implantable biocompatible capsule.

In a further embodiment the injection is intravenous, intramuscular, intraspinal, intraperitoneal, subcutaneous, a bolus or a continuous administration.

In one embodiment the pharmaceutical composition according to the present invention is administered at intervals of 30 minutes to 24 hours.

In a further embodiment the pharmaceutical composition according to the present invention is administered at intervals of 1 to 6 hours.

In a further embodiment the pharmaceutical composition according to the present invention is administered at intervals of 6 to 72 hours.

In another embodiment the pharmaceutical composition comprising the antagonist/inhibitor to the Vps10p-domain receptor according to the present invention is administered at a dosage of between 10 µg to 500 mg per kg body mass.

DETAILED DESCRIPTION OF THE DRAWINGS

FIG. 1: The Vps10p-domain receptor family. Their structural organization is indicated.

FIG. 2a: Cholesterol and triglyceride metabolism. Chylomicrons (CM) transport dietary triglycerides to tissues where they are removed by the action of lipoprotein lipase (LpL). Apolipoprotein C2 (C2) activates LpL. The resultant remnant particles (CMR) are removed by the liver. They bind to remnant receptors which recognize apo E (E), are internalized and catabolized. Apolipoproteins A (A) and B48 (B48) are synthesized in intetinal cells, whereas apoE is acquired from high-density lipoprotein particles (HDL) together with cholesterol. As triglycerides are removed from chylomicrons, apo A, apo C, cholesterol and phopholipids are relased from their surfaces and transferred to HDL where the cholesterol is esterified. Cholesteryl ester is transferred back to the remnant particle in exchange for triglycerides by cholesteryl ester transport protein.

FIG. 2b: Cholesterol and triglyceride metabolism. Very low density lipoprotein particles (VLDL) are synthesized in the liver and transport endogenous triglyceride from the liver to other tissues where it is removed by the action of lipoprotein lipase (LpL). At the same time, cholesterol, phospholipids and apo C(C2) and apo E (E) are released and transferred to high-density lipoprotein particles (HDL). By this process VLDL are converted IDL (not shown). Some IDL is removed by the liver but most has more triglyceride removed by hepatic lipase and is thereby converted into low-density lipoprotein particles (LDL) (not shown). Thus the triglyceride-rich VLDL particles are precursors of LDL, which comprise mainly cholesterol (cholesteryl esters) and apo B100. LDL is ultimately removed from the circulation by LDL receptors present in the liver but also in peripheral tissues.

FIG. 3: Plasma cholesterol levels in Sortilin knockout mice. Cholesterol levels were measured in wild-type mice (LDLR×Sort; +/+,+/+), mice lacking Sortilin expression (LDLR×Sort; +/+,−/−), mice devoid in the low-density liprotein receptor LDLR (LDLR×Sort; −/−,+/+), and double knockout mice lacking expression of both receptors (LDLR×Sort; −/−,−/−). The animals were fed a western-type diet rich in lipids for 4-6 weeks, fasted overnight and plasma samples were analysed for cholesterol. Sortilin knockout mice exhibit a border significant reduction in plasma cholesterol as compared to control littermates (wild-type) (p=0.06). In LDL receptor deficient mice, a mouse model of familiar hypercholesterolemia, the elevated cholesterol levels were diminished in the absence of Sortilin (LDLR×Sort; −/−,−/−) (p=0.02).

FIG. 4: Plasma triglyceride levels in Sortilin knockout mice. Triglycerides were measured in wild-type mice (LDLR×Sort; +/+,+/+), mice lacking Sortilin expression (LDLR×Sort; +/+,−/−), mice devoid in the low-density liprotein receptor, LDLR, (LDLR×Sort; −/−,+/+), and double knockout mice lacking expression of both receptors (LDLR×Sort; −/−,−/−). The animals were fed a western-type diet rich in lipids for 4-6 weeks, fasted overnight and plasma samples were analysed for cholesterol. Sortilin knockout mice showed a moderate increase in plasma triglycerides as compared to control littermates (wild-type). In LDL receptor Sortilin double knockout mice (LDLR×Sort; −/−,−/−), triglyceride levels were considerably elevated as compared to mice lacking only LDLR.

Figure 5A:
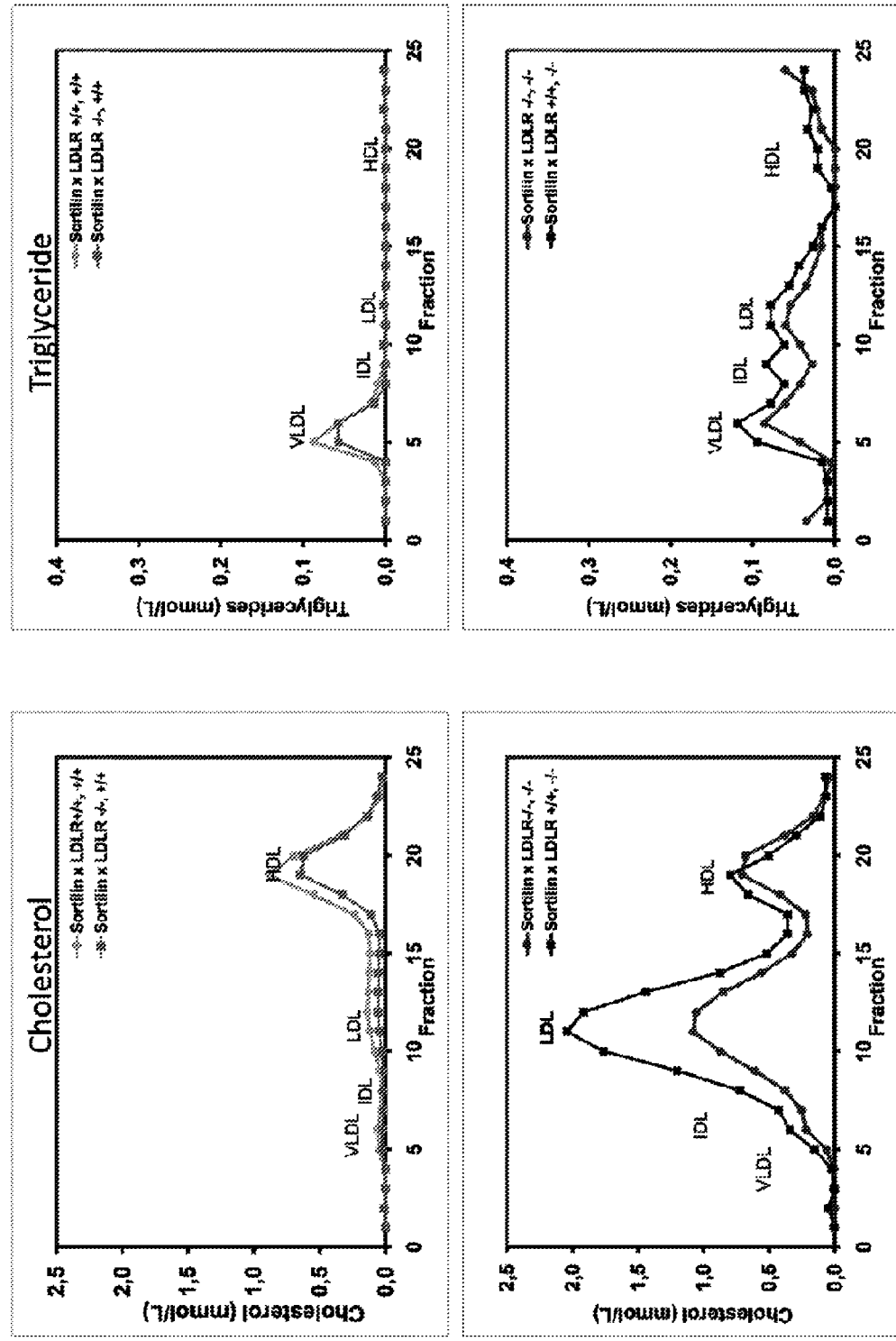

FIG. 5a: Lipoprotein profile—cholesterol (left) and triglyceride (right). FPLC profiles of mouse plasma lipoproteins from wild-type mice (LDLRxSort; +/+,+/+), mice lacking Sortilin expression (LDLRxSort; +/+,−/−), mice devoid in the low-density liprotein receptor, LDLR, (LDLRxSort; −/−,+/+), and double knockout mice lacking expression of both receptors (LDLRxSort; −/−,−/−). Mice with the indicated genotypes were fed a Western-type diet for 4-6 weeks and plasma samples were collected from each animal and subjected to gel filtration on FPLC. The cholesterol and triglyceride content in each fraction was subsequently measured. The retention time of the various lipoprotein particles are indicated.

FIG. 5b: Characterization of ApoB binding to recombinant human sortilin (30). Sortilin was immobilized on a BIAcore CM5 sensorchip at a density of 0.078 µmol/mm². A) After baseline calibration in running buffer (10 mM Hepes, 150 mM NaCl, 1 mM EGTA, 1.5 mM $CaCl_2$, 0.005% P20, pH 7.4) 10 µg/ml rabbit anti-sortilin IgG (12) or running buffer alone was applied to the chip. At t=700 sec the response units obtained in the presence of anti-sortilin IgG was arbitrarily set at 100 and 50 nM ApoB was applied to the flow cell pre-incubated with antibody or with buffer alone. Association of ApoB binding was measured until 1200 sec, after which the solute was changed to buffer to allow dissociation. B) Data extracted from panel A. Binding of ApoB at t=1200 sec to the flow cell following pre-incubation with running buffer alone (=maximum ApoB binding) was set at 100 relative response units. When pre-incubated with the inhibitory anti-sortilin antibody, no ApoB binding was observed. C) Surface plasmon resonance analysis of ApoB (10, 20, 50 nM) binding to immobilized sortilin. The on and off rates were recorded, and the $K_d$ value was 0.4 nM for binding to sortilin in the displayed experiment.

FIG. 6: Time-course for increase in cholesterol levels and FPLC profile in mice that over-express Sortilin. Data normalized to 100% at Day 0 (t=0). There is an increase in plasma cholesterol selectively in mice that received adenovirus with sortitin (round marker) and not in mice that received adenovirus with LacZ (square marker). On the right is a FPLC of plasma. Mice were subjected to WTD from day −14 to day 14 (28 days).

FIG. 7: Western Blot (WB) for apoproteins in mice that over-express Sortilin. Plasma was sampled 14 days after injection of either Adenovirus with Sortilin or LacZ (tail vein injection), and subsequently immunoblotted for ApoB and ApoE. There is a higher concentration of ApoB100 and, to a lesser extent, a higher concentration of ApoE in mice that received adenovirus with sortilin compared to adenovirus with ApoE. Mice were subjected to WTD from day −14 to day 14 (28 days).

Figure 8:
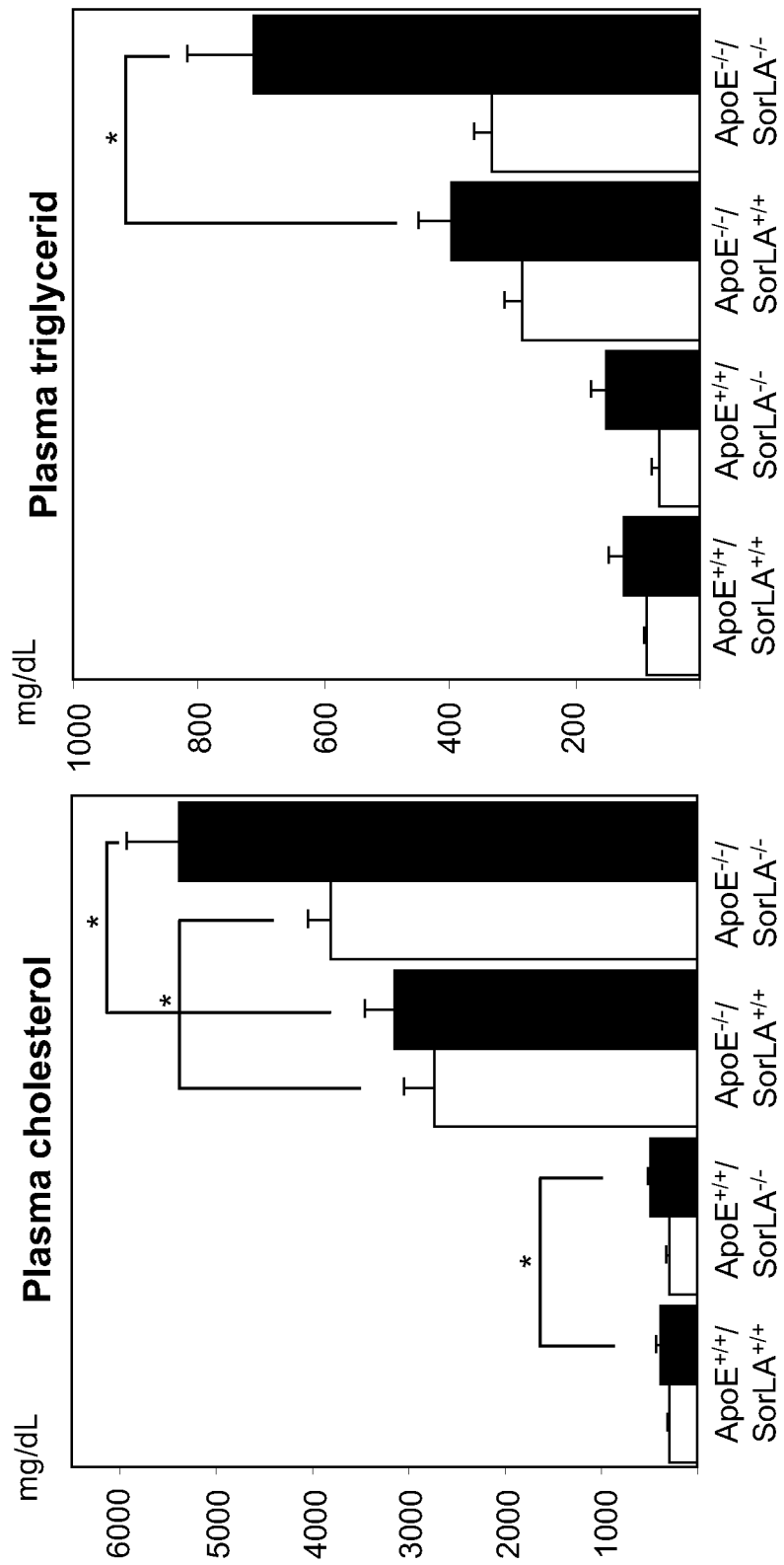

FIG. 8: Cholesterol and triglyceride levels in SorLA/ApoE double knockout mice. Lipids (cholesterol and triglycerides) were measured in wild-type mice (ApoExSorLA; +/+,+/+), mice lacking SorLA expression (ApoExSorLA; +/+,−/−), mice devoid in apolipoprotein E (ApoExSorLA; −/−,+/+), and double knockout mice lacking expression of both proteins (ApoExSorLA; −/−,−/−). The male mice were fed a western-type diet rich in lipids for 4-6 weeks, fasted overnight and plasma samples were analysed for cholesterol and triglycerides. SortLA knockout mice exhibit a significant increase in plasma cholesterol as compared to control littermates (wild-type) (p<0.05). In apoE deficient mice, cholesterol and triglycerides were increased in the absence of SorLA (ApoExSorLA; −/−,−/−) (p<0.001).

Figure 9:
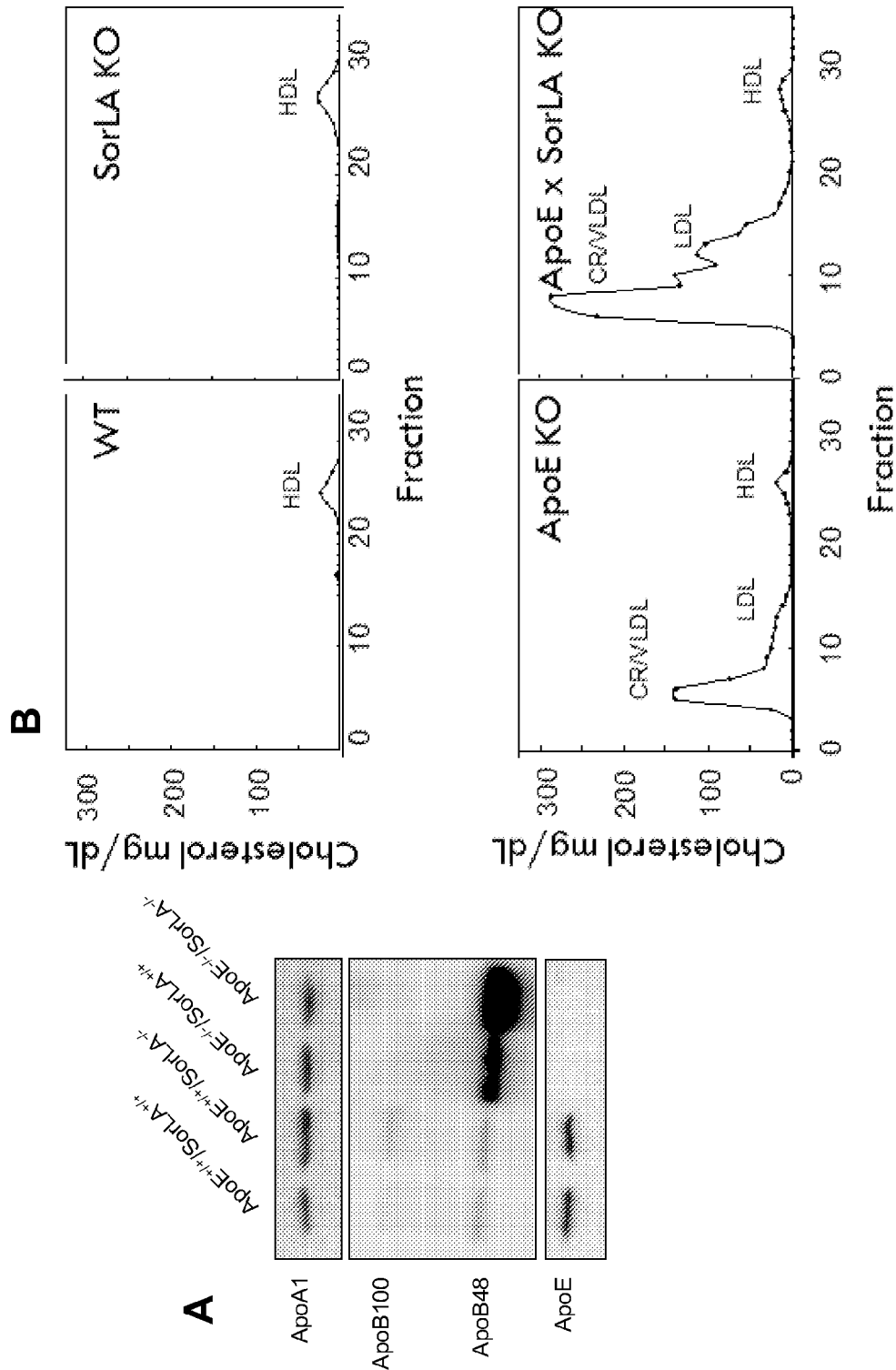

FIG. 9: Apoliporoteins and liprotein profiles SorLA/ApoE double knockout mice. Panel A) Serum from transgenic mice with the indicated genotypes fed a Western-type diet were allpied to reducing SDS-PAGE followed by Western blotting using antibodies against ApoA1, ApoB and ApoE. Panel B) Lipoprotein profiles—cholesterol. FPLC profiles of mouse plasma lipoproteins from wild-type mice (ApoExSorLA; +/+,+/+), mice lacking SorLAn expression ApoExSorLA; +/+,−/−), mice devoid in the apolipoprotein ApoE, (ApoExSorLA; −/−,+/+), and double knockout mice lacking expression of both proteins (ApoExSorLA; −/−,−/−). Mice with the indicated genotypes were fed a Western-type diet for 4-6 weeks and plasma samples were collected from each animal and subjected to gel filtration on FPLC. The cholesterol content in each fraction was subsequently measured. The retention time of the various lipoprotein particles are indicated.

FIG. 10: Competition of peptides with GST C-terminally tagged with Tyr-Ile-Leu (YIL). Binding to immobilized sSortilin was measured by surface plasmon resonance. 100% corresponds to the measured response units obtained for 100 nM GST-YIL in the absence of competing peptide. The EC50 values is the concentration of peptide at which the GST-YIL binding is reduced to 50%. Sequences are given for the peptides and for peptides that contain non-natural amino acids the structure is also shown.

Overview of Sequences
SEQ ID NO 1: Sortilin
SEQ ID NO 2: SorLA
SEQ ID NO 3: SorCS1
SEQ ID NO 4: SorCS2
SEQ ID NO 5: SorCS3
SEQ ID NO 6: pre-pro-NGF
SEQ ID NO 7: pre-pro-BDNF
SEQ ID NO 8: Neurotrophin-3
SEQ ID NO 9: Neurotrophin-4/5
SEQ ID NO 10: Neurotensin (1-13)
SEQ ID NO 11: PYIL (C-term. of Neurotensin)
SEQ ID NO 12: NT69L
SEQ ID NO 13: Receptor associated peptide (RAP)
SEQ ID NO 14: Apolipoprotein E (ApoE)
SEQ ID NO 15: Lipoprotein lipase (LpL)

EXAMPLES

Example 1

Determination of Plasma Concentration of Cholesterol and Cholesterol-Containing Lipoproteins 8-12 weeks old mice were during 4-6 weeks fed a Western-type diet whereafter measurements and determination of cholesterol and lipoprotein particles was made. The following strains were used: Wild-type mice and mice lacking Sortilin expression (Jansen et al, Nat. Neurosci. (2007) 10:1449-,), LDL receptor (LDLR) deficient mice (Ishibashi et al (1993) J. Clin. Invest. 92:883-), SorLA knockout mice (Andersen et al, PNAS (2005) 102:13461-) and mice with disrupted ApoE expression (Zhang et al, Science (1992) 258:468-). The mice were intercrossed to generate a line lacking Sortilin and LDLR expression and a line devoid in both ApoE and SorLA. Blood samples were taken in the morning after fasting 12 hours by retroorbital bleeding of ether-anesthetized animals. Blood was transferred to heparin coated tubes on ice. Following centrifugation at 5400 rpm (3000 g) for 15 minutes at 4° C., total cholesterol was determined using a cholesterol CHOD-PAP" kit from Roche/Hitachi. In brief, cholesterol was measured by mixing the samples with Cholesterol CHOD-PAP reagents. After incubation the optical density (O.D.) was measured at 492 nm. A calibration curve of a cholesterol standard was be made in the same experiment. FIG. 3 depicts decreased cholesterol levels in Sortilin knockout mice as compared to control littermates. Moreover, Sortilin/LDLR double deficient mice are protected against the increase in cholesterol levels observed in the LDLR knockouts. In contrast, mice lacking SorLA have increased plasma cholesterol levels and deficiency of both SorLA and ApoE results in higher cholesterol levels than deficiency for ApoE alone (FIG. 8).

Measurement of lipoprotein profiles by FPLC analysis were performed using an ÄKTA apparatus. Lipoproteins were separated on a Superose™ 6 PC3.2/30 column with an AKTA™ purifier10 using the TimeSuperose6 method in the Unicorn 5.11 program (GE Healthcare). In short: Plasma was diluted to <5 mmol/L cholesterol before injection. 50 µl of the diluted sample was injected onto the column. Analysis was performed in freshly prepared samples. Cholesterol was subsequently measured in the fractions (see above). FIG. 5a shows such an experiment. It is evident that Sortilin−/− mice are characterized by reduced LDL levels as compared to control mice. Likewise, mice lacking both Sortilin and LDLR have reduced LDL concentrations when compared to mice only lacking LDLR expression. Of note, SorLA/ApoE double knockouts are characterized by VLDL concentrations dramatically higher than that observed for mice lacking only ApoE−/− expression (FIGS. 9A and B). The data demonstrate that Sortilin and SorLA are capable of modifying cholesterol levels and LDL (for Sortilin) and VLDL (for SorLA) concentrations in vivo.

Example 2

Determination of Plasma Concentration of Triglycerides and Triglyceride-Containing Lipoproteins 8-12 weeks old mice were fed 4-6 weeks a Western-type diet and used cholesterol measurements and determination of lipoprotein particles. The following strains were used: Wild-type mice. Mice lacking Sortilin expression (Jansen et al, (2007) Nat. Neurosci. 10:1449-), LDL receptor (LDLR) deficient mice (Ishibashi et al (1993) J. Clin. Invest. 92:883-), SorLA knockout mice (Andersen et al, PNAS (2005) 102: 13461-) and mice with disrupted ApoE expression (Zhang et al, Science (1992) 258:468-). The mice were intercrossed to generate a line lacking Sortilin and LDLR expression and a line devoid in both ApoE and SorLA. Blood samples were taken in the morning after fasting 12 hours by retroorbital bleeding of ether-anesthetized animals. Blood was transferred to heparin coated tubes on ice. Following centrifugation at 5400 rpm (3000 g) for 15 minutes at 4° C., triglycerides were determined using a commercially available kit "Triglycerides GPO-PAP" kit (Roche/Hitachi). Total triglycerides were determined by mixing the samples with Triglycerides GPO-PAP reagents from Roche/Hitachi. After incubation the O.D. was measured at 492 nm. A calibration curve of a glycerol standard was made in the same experiment. FIG. 4 shows slightly increased triglyceride levels in LDLR−/− mice when compared to control littermates. Likewise, mice devoid in both ApoE and SorLA are characterized by higher triglyceride levels than animals lacking only ApoE contrast, mice lacking SorLA have increased plasma cholesterol levels and deficiency of both SorLA and ApoE results in higher cholesterol levels than deficiency for ApoE alone (FIG. 8). Measurement of triglyceride lipoproteins were performed using FPLC on an ÄKTA apparatus. Lipoproteins were separated on a Superose™ 6 PC3.2/30 column with an ÄKTA purifier10 using the TimeSuperose6 method in the Unicorn 5.11 program (GE Healthcare). In short: Plasma was diluted to <5 mmol/L cholesterol before injection. 50 µl of the diluted sample was injected onto the column. Analysis was performed in freshly prepared samples. Triglycerides was subsequently measured in the fractions (see above). FIG. 5a shows such an experiment.

Example 3

Evaluating Effect of Over-Expression of Sortilin Using Adenoviral Vectors 8 weeks old mice were during 4 weeks (day −14 to day 14) fed a Western-type diet whereafter measurements and determination of cholesterol (and triglyceride and ALAT) and lipoprotein particles was made (day 0, 7 and 14). Wild-type mice were used. Blood samples were taken in the morning after fasting 12 hours by retroorbital bleeding of ether-anesthetized animals. Blood was transferred to heparin coated tubes on ice. Following centrifugation at 5400 rpm (3000 g) for 15 minutes at 4° C., total cholesterol was determined using a cholesterol CHOD-PAP" kit from Roche/Hitachi. On day 0, mice were injected in the tail vein with either an adenoviral vector with sortilin or LacZ. Measurements of cholesterol were made on day 7 and 14 to evaluate the effect of the protein. In FIG. 6 the effect is illustrated. Mice with overexpression of sortilin exhibited a marked increase in cholesterol compared to day 0. This increase was not seen in mice that received LacZ. WB of livers were applied to verify the increased amount of sortilin, and staining for LacZ to check the mice that received the viral vector with LacZ. A WB of apoproteins B and E (FIG. 7) shows a marked increase in ApoB100 in mice that received the adenovirus with sortilin.

Example 4

In Vitro Screening Method for Identifying Vps10p-Domain Receptor Antagonists and Ligands Determination of direct binding of ligand to immobilized protein can be performed by e.g. surface plasmon resonance analysis (Biacore, Sweden) using CaHBS as standard running buffer (10 mM HEPES, pH 7.4, 140 mM NaCl, 2 mM CaCl2, 1 mM EGTA, and 0.005% Tween-20). A biosensor chip from Biacore (CM5, cat. no. BR-1000-14) is activated using the NHS/EDC method as described by supplier followed by coating with a receptor belonging to the Vps10p-domain receptor family. Several different approaches can be applied: Candidate receptor antagonist can be identified by comparing the binding signal (response units) to a chip immobilized with one of the receptors and comparing this signal to an empty flow cell. In another approach, inhibition of an established ligand can be monitored in the absence or presence of putative inhibitors. The difference in the signal depicts the inhibitory potential of the antagonist. The data collected are analysed by fitting of sensorgrams for affinity estimations and inhibitory potential using the Biaevaluation version 3.1 program. We evaluated the binding properties of ApoB to sortilin (FIG. 5b). A) After baseline calibration in running buffer (10 mM Hepes, 150 mM NaCl, 1 mM EGTA, 1.5 mM CaCl2, 0.005% P20, pH 7.4) 10 ug/ml rabbit anti-sortilin IgG (Nykjaer et al, Nature (2004) 427:843-848) or running buffer alone was applied to the chip. At t=700 sec the response units obtained in the presence of anti-sortilin IgG was arbitrarily set at 100 and 50 nM ApoB was applied to the flow cell pre-incubated with antibody or with buffer alone. Association of ApoB binding was measured until 1200 sec, after which the solute was changed to buffer to allow dissociation. B) Data extracted from panel A. Binding of ApoB at t=1200 sec to the flow cell following pre-incubation with running buffer alone (=maximum ApoB binding) was set at 100 relative response units. When pre-incubated with the inhibitory anti-sortilin antibody, no ApoB binding was observed. C) Surface plasmon resonance analysis of ApoB (10, 20, 50 nM) binding to immobilized sortilin. The on and off rates were recorded, and the $K_d$ value was 0.4 nM for binding to sortilin in the displayed experiment. So ApoB can bind with high affinity to Sortilin and this binding can be inhibited using either antibodies or neurotensin (NT).

The surface Plasmon resonance assay can easily be transformed into other assays in which the Vps10p-domain receptor, the ligand or the putative inhibitor is immobilized on a solid phase. For instance, receptors can be immobilized in e.g. Maxisorp microtiter wells from Nunc (cat. no. 439454) by incubation for 16 h at 4° C. in 50 mM $NaHCO_3$, pH 9.6. After blocking using 5% bovine serum albumin (Sigma, cat. no. A9647) for 2 h at room temperature, the wells are washed three times with MB buffer (10 mM HEPES, pH 7.4, 140 mM NaCl, 2 mM $CaCl_2$, and 1 mM $MgCl_2$) before incubation with a labelled ligand (e.g. iodinated) in the absence or presence of a various concentrations of a candidate inhibitor. Following incubation (e.g. overnight at 4° C.) and washing with MB buffer, bound radioactivity is released by adding 10% SDS. Nonspecific binding of tracer to wells coated only with bovine serum albumin is determined and subtracted from the values determined in the binding experiments. The binding data point can be fitted to binding equations using the Prism software from GraphPad, version 4. Likewise, the antagonist can be labelled and binding to the immobilized receptor directly measured. In yet another setup, the receptor, ligand or antagonist can be immobilized on scintillation beads and binding measured in a scintillation proximity assay in which the receptor-binding molecule has been labelled using radioactivity.

Example 5

A Cell Based Screening Method for Identifying Vps10p-Domain Receptor Antagonists Determination of binding, internalization or signaling by members of the Vps10p-domain receptor family can be performed in cellular systems. Cells expressing one of the receptors, either endogenously or following e.g. transfection with a plasmid containing the cDNA of the receptor are incubated with a radio-labeled ligand, in the absence and the presence respectively, of a candidate inhibitor/antagonist compound. After incubation, the cells are washed to remove unspecific binding and subsequently harvested. The degree of binding of the candidate antagonist/inhibitor to the receptor is determined by using a conventional radioligand assay well known to those skilled in the art. See e.g. Bylund and Toews (1993) Am J Physiol. 265(5 Pt 1):L421-9 entitled "Radioligand binding methods: practical guide and tips". Likewise, endocytosis/internalization may be determined as described in Nykjr et al (1992) FEBS 300:13- and Nielsen et al (2001) EMBO J., 20:2180-.

Example 6

An In Vivo Based Screening Method for Identifying Vps10p-Domain Receptor Antagonists Identification of candidate antagonists capable of inhibiting binding and/or internalization and/or signaling of a Vps10p-domain receptor is performed in wild type mice or another animal suitable for the purpose.

The animals are fed a western-type diet rich in lipids during a period of 4-6 weeks, during which period candidate antagonists potentially capable of inhibiting binding to, internalisation by and signalling through a Vps10p-domain receptor (selected from the group consisting of SEQ ID NO. 1 to 5), are administered to said animal. Control animals are fed a normal chow of a western-type diet rich in lipids during a period of 4-6 weeks in the absence of candidate antagonist compounds.

At the end of the period the animals are fasted over-night and plasma samples are taken and analysed for the level of cholesterol in the two groups of animals. The difference between the group to which the candidate antagonist has been administered and the control group indicate the degree of inhibition Example 7

An In Vivo Based Screening Method for Identifying Vps10p-Domain Receptor Antagonists Identification of candidate antagonists capable of inhibiting binding and/or internalization and/or signaling of a Vps10p-domain receptor is performed in wild type mice or another animal suitable for the purpose.

The animals are fed a western-type diet rich in lipids during a period of 4-6 weeks, during which period radiolabelled candidate antagonists potentially capable of inhibiting binding to, internalisation by and signalling through a Vps10p-domain receptor, are administered to said animal. Control animals are fed a western-type diet rich in lipids during a period of 4-6 weeks in the absence of said radiolabelled candidate antagonist compounds. At the end of the period the animals are fasted over-night and sacrificed whereafter representative tissues are dissected and determination of the amount of bound and/or accumulated radiolabelled ligand is determined using a conventional scintillation assay.

Example 8

An In Vivo Based Evaluation of the Potency of the Vps10p-Domain Receptor Antagonist A hypercholesterolemic patient is treated with a conventional (e.g. a statin) or dietary regime whereby the serum cholesterol level is determined. Subsequently, the patient replaces his statin treatment during one month by the Vps10p-domain receptor antagonist for up to 4-6 weeks with a preparation according to the present invention, whereby the cholesterol level is again determined and compared to the level obtained with or without the conventional treatment (e.g. a statin) or dietary regime.

Example 9

Method of Treatment

A 55-year-old man is diagnosed with severe hyperlipidemia. The physician in charge decides that the patient shall receive Vps10p-domain receptor antagonists to reduce the abnormal plasma lipid levels. A subcutaneous or intravenous bolus injection of a compound of this invention is administered. The dose is in the interval 0.5 mg/kg to 50 mg/kg. At the hospital, the plasma lipid levels as well as the general condition of the patient is continuously monitored until a stable normal level of the plasma lipid level is obtained. The patient is prescribed injection or an orally available equivalent of the compound of the invention injected at the hospital. The oral dose is in the interval 0.5 mg/kg to 50 mg/kg body weight.

Example 10

Method of Treatment

A 55-year-old man is diagnosed with hypercholesterolemia through a longer period. Conventional intervention has not lowered plasma cholesterol sufficiently. A measurement of sortilin in the liver shows high levels. It is decided at the department to lower the sortilin concentration in the liver using siRNA targeted to the liver. At the hospital, the plasma lipid levels as well as the general condition of the patient is continuously monitored until a stable normal level of the plasma lipid level is obtained. The patient is prescribed injection or an orally available equivalent of the compound of the invention injected at the hospital.

REFERENCES

1. Goldstein, J. L., Hobbs, H. H. and Brown, M. S. (2001). Familial Hypercholesteremia. In: Metabolic and Molecular Bases of Inherited Disease Eight edition, New York: McGraw-Hill, 2863-2913.
2. Tannock L R. Advances in the management of hyperlipidemia-induced atherosclerosis. Expert Rev Cardiovasc Ther. 2008 March; 6(3):369-83.
3. Charlton-Menys V, Durrington P N. Human cholesterol metabolism and therapeutic molecules. Exp Physiol. 2008 January; 93(1):27-42.
4. Baker S K, Samjoo I A. A neuromuscular approach to statin-related myotoxicity. Can J Neurol Sci. 2008 March; 35(1):8-21.
5. Radcliffe K A, Campbell W W. Statin myopathy. Curr Neurol Neurosci Rep. 2008 January; 8(1):66-72.
6. Petersen et al., J. Biol. Chem., 272:3599-3605 (1997)
7. Herman-Borgmeyer et al., Mol. Brain Res., 65:216-219 (1999)
8. Jacobsen et al., J. Biol. Chem., 271:31379-31383 (1996)
9. Marcusson, E. G., et al., Cell, 77:579-586 (1994)
10. J. Mazella et al., J Biol Chem 273, 26273 (1998).
11. C. Munck Petersen et al., Embo J 18, 595 (1999).
12. A. Nykjaer et al., Nature 427, 843 (2004).
13. H. K. Teng et al., J Neurosci 25, 5455 (2005).
14. U. B. Westergaard et al., J Biol Chem 279, 50221 (2004).
15. S. Maeda et al., J Cell Physiol 193, 73 (2002).
16. M. S. Nielsen, C. Jacobsen, G. Olivecrona, J. Gliemann, C. M. Petersen, J Biol Chem 274, 8832 (1999).
17. M. S. Nielsen et al., Embo J 20, 2180 (2001).
18. K. Nakamura, K. Namekata, C. Harada, T. Harada, Cell Death Differ 14, 1552 (2007).
19. P. Jansen et al., Nat Neurosci 10, 1449 (2007).
20. P. Chalon et al., FEBS Lett 386, 91 (1996).
21. L. Jacobsen et al., J Biol Chem 276, 22788 (2001).
22. K. Tanaka, M. Masu, S. Nakanishi, Neuron 4, 847 (1990).
23. J. P. Vincent, J. Mazella, P. Kitabgi, Trends Pharmacol Sci 20, 302 (1999).
24. Willer et al. (2008) Nature Genetics 40(2): 161-169
25. Kathiresan et al. (2008) Nature Genetics 40(2): 189-97
26. U. B. Westergaard, K. Kirkegaard, E. S. Sørensen, C. Jacobsen, M. S. Nielsen, C. M. Petersen, P. Madsen, (2005) FEBS Letters 579:1172-1176
27. Clee S M, Yandell B S, Schueler K M, Rabaglia O C, Richards O C, Raines S M, Kabara E A, Klass D M, Mui E T, Stapleton D S, Gray-Keller M P, Young M B, Stoehr J P, Lan H, Boronenkov I et al. Positional cloning of SorCS1, a type 2 diabetes quantitative trait locus. (2006) Nature Genetics 38:688-693
28. Goodarzi M O, Lehman D M, Taylor K D, Guo X, Cui J, Quinones M J, Clee S M, Blangero J, Hsuch W A, Attie A D, Stern M P, Rotter J I. SorCS1: a novel human type 2 diabetes susceptibility gene suggested by the mouse. (2007) Diabetes 56:1922-1929.
29. Granhall, C., Rosengren, A. H., Renstrom, E., Luthman, H. (2006) Diabetes 55: 3494-3500.
30. Quistgaard et al, Nat. Struc. Mol. Biol. (2009) 16: 96-98

The invention claimed is:

1. A method for identifying a desired antagonist for regulating plasma lipid concentrations, comprising the steps of:
    (1)(a) incubating cells that express a Vps10p-domain receptor that comprises an amino acid sequence having at least 95% sequence identity to SEQ ID NO:1 (Sortilin), said cells being in an in vitro cell culture, in the presence of a Vps10p-domain receptor agonist under conditions sufficient to permit:
        (i) agonist binding to said Vps10p-domain receptor;
        (ii) agonist internalization by said Vps10p-domain receptor; or
        (iii) agonist-promoted signalling by said Vps10p-domain receptor;
    wherein said cells and said agonist are further incubated in the presence of a candidate antagonist;
    (1)(b) determining whether the presence of said candidate antagonist affects:
        (i) the extent of binding between said Vps10p-domain receptor and said agonist;
        (ii) the extent of agonist internalization by said Vps10p-domain receptor; or
        (iii) the extent of agonist-promoted signalling by said Vps10p-domain receptor,
    wherein a decrease in the extent of said binding, said internalization or said signalling observed in the presence of said candidate antagonist relative to the extent of said binding, said internalization or said signalling occurring in the absence of said candidate antagonist identifies said candidate antagonist as being capable of inhibiting an activity of said Vps10p-domain receptor;
    (2)(a) administering said candidate antagonist to an animal expressing said Vps10p-domain receptor; and
    (2)(b) determining whether administration of said candidate antagonist to said animal alters the level of plasma cholesterol as compared to a control animal expressing said Vps10p-domain receptor, wherein said control animal is not administered said candidate antagonist,
    wherein a difference in the level of plasma cholesterol between said animal administered said candidate antagonist and said control animal identifies said candidate antagonist as being a desired antagonist capable of regulating plasma lipid concentrations, and wherein said agonist is SEQ ID NO:6 (proNGF) or a polypeptide having at least 95% sequence identity to SEQ ID NO:6.

2. The method of claim 1, wherein said cells naturally express said Vps10p-domain receptor, and wherein said method additionally comprises:
    (1)(c) incubating cells that do not express said Vps10p-domain receptor, said non-expressing cells being in an in vitro cell culture, in the presence of said agonist and in the absence of said candidate antagonist under said conditions;
    (1)(d) incubating said non-expressing cells in an in vitro culture in the presence of said agonist and said candidate antagonist under said conditions; and
    (1)(e) comparing a physiological response of said non-expressing cells incubated in the absence of said candidate antagonist to a physiological response of said non-expressing cells incubated in the presence of said candidate antagonist;
    wherein said candidate antagonist is a desired antagonist if the physiological responses of said non-expressing cells incubated in the absence and in the presence of said candidate antagonist are the same.

3. The method of claim 1, wherein said cells naturally express said Vps10p-domain receptor, and wherein said method additionally comprises:

(1)(c) incubating cells that overexpress said Vps10p-domain, said overexpressing cells being in an in vitro cell culture, in the presence of said agonist and in the absence of said candidate antagonist under said conditions;

(1)(d) incubating said overexpressing cells in an in vitro culture in the presence of said agonist and said candidate antagonist under said conditions; and (1)(e) determining whether the presence of said candidate antagonist affects:
  (i) the extent of binding between said overexpressing cells and said agonist;
  (ii) the extent of agonist internalization by said overexpressing cells; or
  (iii) the extent of agonist-promoted signalling by said overexpressing cells;

wherein, when said conditions are the same, an extent of said binding, said internalization or said signaling observed in the presence of said candidate antagonist by said cells that overexpress said Vps10p-domain relative to the extent of said binding, said internalization or said signalling occurring in the absence of said candidate antagonist by said cells that overexpress said Vps10p-domain, that is less than the extent of said binding, said internalization or said signaling observed in the presence of said candidate antagonist by said cells that naturally express said Vps10p-domain relative to the extent of said binding, said internalization or said signalling occurring in the absence of said candidate antagonist by said cells that naturally express said Vps10p-domain, identifies said candidate antagonist as being a desired-antagonist.

4. A method for identifying a desired antagonist for regulating plasma lipid concentrations, comprising the steps of:

(1)(a) providing a candidate Vps10p-domain receptor antagonist to a mammal having cells that express said Vps10p-domain receptor, wherein said Vps10p-domain receptor comprises an amino acid sequence having at least 95% sequence identity to SEQ ID NO:1, (1)(b) determining whether the presence of said candidate antagonist affects:
  (i) the amount of antagonist bound to the Vps10p-domain receptor of said cells of said mammal; and/or
  (ii) the amount of agonist internalised by the Vps10p-domain receptor of said cells of said mammal; and/or
  (iii) the degree of monist-promoted signalling through the Vps10p-domain receptor by said cells of said mammal, wherein said monist is SEQ ID NO:6 (proNGF) or a polypeptide having at least 95% sequence identity to SEQ ID NO:6, and wherein a decrease in the extent of said binding, said internalization or said signalling observed in the presence of said candidate antagonist relative to the extent of said binding, said internalization or said signalling occurring in the absence of said candidate antagonist identifies said candidate antagonist as being capable of inhibiting an activity of a Vps10p-domain receptor;

(2)(a) administering said candidate antagonist to an animal expressing said Vps10p-domain receptor; and (2)(b) determining whether administration of said candidate antagonist to said animal alters the level of plasma cholesterol as compared to a control animal expressing said Vps10p-domain receptor, wherein said control animal is not administered said candidate antagonist, wherein a difference in the level of plasma cholesterol between said animal administered said candidate antagonist and said control animal identifies said candidate antagonist as being a desired antagonist capable of regulating plasma lipid concentrations.

5. The method of claim 4, wherein said cells that express said Vps10p-domain do not naturally express said Vps10p-domain.

6. The method of claim 4, wherein said method additionally comprises:

(1)(c) providing said candidate Vps10p-domain receptor antagonist to a mammal not expressing said Vps10p-domain receptor, (1)(d) comparing a physiological response of cells of said non-expressing mammal in the presence of said candidate antagonist to a physiological response of cells of said non-expressing mammal in the absence of said candidate antagonist;

wherein said candidate antagonist is a desired antagonist if the physiological responses of said cells of said non-expressing mammal in the absence and in the presence of said candidate antagonist are the same.

7. The method according to claim 1, wherein said candidate antagonist is an antibody selected from the group consisting of a polyclonal antibody, a monoclonal antibody, a humanised antibody, a single chain antibody and a recombinant antibody.

8. The method according to claim 7, wherein the antibody is directed against the extracellular part of Sortilin.

9. The method according to claim 1, wherein the bioactive agent said candidate antagonist is capable of binding to a binding site of Sortilin comprising amino acid residues R325, S316, Y351, I353, K260, I327, F314, F350 to M363, S305, F306, T398 to G400, I303-G309, Q349-A356, Y395 and T402 of SEQ ID NO:1.

10. The method according to claim 1, wherein said candidate antagonist is capable of binding to a binding site of Sortilin comprising amino acid residues L572, L114, V112, R109 to S111, S115 to G118, T570, G571, W586, W597, T168-I174, L572, A573 and S584 to F588 of SEQ ID NO:1.

11. The method according to claim 1, wherein said candidate antagonist is capable of binding to a binding site of Sortilin comprising amino acid residues D403, S420, D422, N423, S424, I425, Q426, E444, T451, Y466, E470, I498, S499 and V500 of SEQ ID NO:1.

* * * * *

UNITED STATES PATENT AND TRADEMARK OFFICE
CERTIFICATE OF CORRECTION

PATENT NO. : 9,084,745 B2  
APPLICATION NO. : 12/993919  
DATED : July 21, 2015  
INVENTOR(S) : Anders Nykjaer et al.

Page 1 of 1

It is certified that error appears in the above-identified patent and that said Letters Patent is hereby corrected as shown below:

In the Claims:
Please amend claim 4, at column 107, line 42 to recite "agonist" in lieu of "antagonist";
Please amend claim 4, at column 107, line 46 to recite "agonist-promoted" in lieu of "monist-promoted";
Please amend claim 4, at column 107, line 49 to recite "agonist" in lieu of "monist"; and
Please amend claim 9, at column 108, lines 39-40 to delete "the bioactive agent".

Signed and Sealed this
Twenty-fourth Day of November, 2015

Michelle K. Lee
*Director of the United States Patent and Trademark Office*

SEQUENCE LISTING

```
<160> NUMBER OF SEQ ID NOS: 15

<210> SEQ ID NO 1
<211> LENGTH: 831
<212> TYPE: PRT
<213> ORGANISM: Homo sapiens
<220> FEATURE:
<221> NAME/KEY: SIGNAL
<222> LOCATION: (1)..(33)
<223> OTHER INFORMATION: Sortilin signal peptide
<220> FEATURE:
<221> NAME/KEY: PROPEP
<222> LOCATION: (34)..(77)
<223> OTHER INFORMATION: Sortilin propeptide
<220> FEATURE:
<221> NAME/KEY: MISC_FEATURE
<222> LOCATION: (78)..(755)
<223> OTHER INFORMATION: Extracellular part of Sortilin (sSortilin)
<220> FEATURE:
<221> NAME/KEY: TRANSMEM
<222> LOCATION: (756)..(778)
<223> OTHER INFORMATION: Membrane spanning part of Sortilin
<220> FEATURE:
<221> NAME/KEY: MISC_FEATURE
<222> LOCATION: (779)..(831)
<223> OTHER INFORMATION: Intracellular (cytoplasmic) domain of Sortilin
```

```
<400> SEQUENCE: 1

Met Glu Arg Pro Trp Gly Ala Ala Asp Gly Leu Ser Arg Trp Pro His
1               5                   10                  15

Gly Leu Gly Leu Leu Leu Leu Gln Leu Leu Pro Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60

Ala Gly Ala Phe Pro Arg Gly Gly Arg Trp Arg Arg Ser Ala Pro
65              70                  75                  80

Gly Glu Asp Glu Glu Cys Gly Arg Val Arg Asp Phe Val Ala Lys Leu
                85                  90                  95

Ala Asn Asn Thr His Gln His Val Phe Asp Asp Leu Arg Gly Ser Val
            100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
        130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
    210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
    290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
    370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415
```

-continued

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
            435                 440                 445

Asp Ala Thr Ala Lys Asn Lys Asn Glu Cys Ser Leu His Ile His Ala
450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ala His Gly Ser Val Gly Asp
                485                 490                 495

Ala Ile Ser Val Met Val Pro Asp Val Tyr Ile Ser Asp Gly Gly
            500                 505                 510

Tyr Ser Trp Thr Lys Met Leu Glu Gly Pro His Tyr Tyr Thr Ile Leu
            515                 520                 525

Asp Ser Gly Gly Ile Ile Val Ala Ile Glu His Ser Ser Arg Pro Ile
            530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
            595                 600                 605

Glu Arg Asn Cys Glu Glu Lys Asp Tyr Thr Ile Trp Leu Ala His Ser
            610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
            675                 680                 685

Val Glu Gln Pro Glu Leu Lys Gly His Asp Leu Glu Phe Cys Leu Tyr
690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
            755                 760                 765

Val Thr Val Val Ala Gly Val Leu Ile Val Lys Lys Tyr Val Cys Gly
            770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830

```
<210> SEQ ID NO 2
<211> LENGTH: 2214
<212> TYPE: PRT
<213> ORGANISM: Homo sapiens
<220> FEATURE:
<221> NAME/KEY: SIGNAL
<222> LOCATION: (1)..(28)
<223> OTHER INFORMATION: Signal peptide of SorLA
<220> FEATURE:
<221> NAME/KEY: PROPEP
<222> LOCATION: (29)..(81)
<223> OTHER INFORMATION: Propeptide of SorLA

<400> SEQUENCE: 2

Met Ala Thr Arg Ser Ser Arg Arg Glu Ser Arg Leu Pro Phe Leu Phe
1               5                   10                  15

Thr Leu Val Ala Leu Leu Pro Pro Gly Ala Leu Cys Glu Val Trp Thr
            20                  25                  30

Gln Arg Leu His Gly Gly Ser Ala Pro Leu Pro Gln Asp Arg Gly Phe
        35                  40                  45

Leu Val Val Gln Gly Asp Pro Arg Glu Leu Arg Leu Trp Ala Arg Gly
    50                  55                  60

Asp Ala Arg Gly Ala Ser Arg Ala Asp Glu Lys Pro Leu Arg Arg Lys
65                  70                  75                  80

Arg Ser Ala Ala Leu Gln Pro Glu Pro Ile Lys Val Tyr Gly Gln Val
                85                  90                  95

Ser Leu Asn Asp Ser His Asn Gln Met Val Val His Trp Ala Gly Glu
            100                 105                 110

Lys Ser Asn Val Ile Val Ala Leu Ala Arg Asp Ser Leu Ala Leu Ala
        115                 120                 125

Arg Pro Lys Ser Ser Asp Val Tyr Val Ser Tyr Asp Tyr Gly Lys Ser
    130                 135                 140

Phe Lys Lys Ile Ser Asp Lys Leu Asn Phe Gly Leu Gly Asn Arg Ser
145                 150                 155                 160

Glu Ala Val Ile Ala Gln Phe Tyr His Ser Pro Ala Asp Asn Lys Arg
                165                 170                 175

Tyr Ile Phe Ala Asp Ala Tyr Ala Gln Tyr Leu Trp Ile Thr Phe Asp
            180                 185                 190

Phe Cys Asn Thr Leu Gln Gly Phe Ser Ile Pro Phe Arg Ala Ala Asp
        195                 200                 205

Leu Leu Leu His Ser Lys Ala Ser Asn Leu Leu Gly Phe Asp Arg
    210                 215                 220

Ser His Pro Asn Lys Gln Leu Trp Lys Ser Asp Asp Phe Gly Gln Thr
225                 230                 235                 240

Trp Ile Met Ile Gln Glu His Val Lys Ser Phe Ser Trp Gly Ile Asp
                245                 250                 255

Pro Tyr Asp Lys Pro Asn Thr Ile Tyr Ile Glu Arg His Glu Pro Ser
            260                 265                 270

Gly Tyr Ser Thr Val Phe Arg Ser Thr Asp Phe Phe Gln Ser Arg Glu
        275                 280                 285

Asn Gln Glu Val Ile Leu Glu Glu Val Arg Asp Phe Gln Leu Arg Asp
    290                 295                 300

Lys Tyr Met Phe Ala Thr Lys Val Val His Leu Leu Gly Ser Glu Gln
305                 310                 315                 320

Gln Ser Ser Val Gln Leu Trp Val Ser Phe Gly Arg Lys Pro Met Arg
                325                 330                 335
```

```
Ala Ala Gln Phe Val Thr Arg His Pro Ile Asn Glu Tyr Tyr Ile Ala
            340                 345                 350

Asp Ala Ser Glu Asp Gln Val Phe Val Cys Val Ser His Ser Asn Asn
        355                 360                 365

Arg Thr Asn Leu Tyr Ile Ser Glu Ala Glu Gly Leu Lys Phe Ser Leu
    370                 375                 380

Ser Leu Glu Asn Val Leu Tyr Tyr Ser Pro Gly Gly Ala Gly Ser Asp
385                 390                 395                 400

Thr Leu Val Arg Tyr Phe Ala Asn Glu Pro Phe Ala Asp Phe His Arg
                405                 410                 415

Val Glu Gly Leu Gln Gly Val Tyr Ile Ala Thr Leu Ile Asn Gly Ser
            420                 425                 430

Met Asn Glu Glu Asn Met Arg Ser Val Ile Thr Phe Asp Lys Gly Gly
        435                 440                 445

Thr Trp Glu Phe Leu Gln Ala Pro Ala Phe Thr Gly Tyr Gly Glu Lys
    450                 455                 460

Ile Asn Cys Glu Leu Ser Gln Gly Cys Ser Leu His Leu Ala Gln Arg
465                 470                 475                 480

Leu Ser Gln Leu Leu Asn Leu Gln Leu Arg Arg Met Pro Ile Leu Ser
                485                 490                 495

Lys Glu Ser Ala Pro Gly Leu Ile Ile Ala Thr Gly Ser Val Gly Lys
            500                 505                 510

Asn Leu Ala Ser Lys Thr Asn Val Tyr Ile Ser Ser Ser Ala Gly Ala
        515                 520                 525

Arg Trp Arg Glu Ala Leu Pro Gly Pro His Tyr Tyr Thr Trp Gly Asp
    530                 535                 540

His Gly Gly Ile Ile Thr Ala Ile Ala Gln Gly Met Glu Thr Asn Glu
545                 550                 555                 560

Leu Lys Tyr Ser Thr Asn Glu Gly Glu Thr Trp Lys Thr Phe Ile Phe
                565                 570                 575

Ser Glu Lys Pro Val Phe Val Tyr Gly Leu Leu Thr Glu Pro Gly Glu
            580                 585                 590

Lys Ser Thr Val Phe Thr Ile Phe Gly Ser Asn Lys Glu Asn Val His
        595                 600                 605

Ser Trp Leu Ile Leu Gln Val Asn Ala Thr Asp Ala Leu Gly Val Pro
    610                 615                 620

Cys Thr Glu Asn Asp Tyr Lys Leu Trp Ser Pro Ser Asp Glu Arg Gly
625                 630                 635                 640

Asn Glu Cys Leu Leu Gly His Lys Thr Val Phe Lys Arg Arg Thr Pro
                645                 650                 655

His Ala Thr Cys Phe Asn Gly Glu Asp Phe Asp Arg Pro Val Val Val
            660                 665                 670

Ser Asn Cys Ser Cys Thr Arg Glu Asp Tyr Glu Cys Asp Phe Gly Phe
        675                 680                 685

Lys Met Ser Glu Asp Leu Ser Leu Glu Val Cys Val Pro Asp Pro Glu
    690                 695                 700

Phe Ser Gly Lys Ser Tyr Ser Pro Val Pro Cys Pro Val Gly Ser Thr
705                 710                 715                 720

Thr Tyr Arg Arg Thr Arg Gly Tyr Arg Lys Ile Ser Gly Asp Thr Cys
                725                 730                 735

Ser Gly Gly Asp Val Glu Ala Arg Leu Glu Gly Glu Leu Val Pro Cys
            740                 745                 750

Pro Leu Ala Glu Glu Asn Glu Phe Ile Leu Tyr Ala Val Arg Lys Ser
```

```
                    755                 760                 765
Ile Tyr Arg Tyr Asp Leu Ala Ser Gly Ala Thr Glu Gln Leu Pro Leu
770                 775                 780

Thr Gly Leu Arg Ala Ala Val Ala Leu Asp Phe Asp Tyr Glu His Asn
785                 790                 795                 800

Cys Leu Tyr Trp Ser Asp Leu Ala Leu Asp Val Ile Gln Arg Leu Cys
                    805                 810                 815

Leu Asn Gly Ser Thr Gly Gln Glu Val Ile Asn Ser Gly Leu Glu
                    820                 825                 830

Thr Val Glu Ala Leu Ala Phe Glu Pro Leu Ser Gln Leu Leu Tyr Trp
                    835                 840                 845

Val Asp Ala Gly Phe Lys Lys Ile Glu Val Ala Asn Pro Asp Gly Asp
850                 855                 860

Phe Arg Leu Thr Ile Val Asn Ser Ser Val Leu Asp Arg Pro Arg Ala
865                 870                 875                 880

Leu Val Leu Val Pro Gln Glu Gly Val Met Phe Trp Thr Asp Trp Gly
                    885                 890                 895

Asp Leu Lys Pro Gly Ile Tyr Arg Ser Asn Met Asp Gly Ser Ala Ala
                    900                 905                 910

Tyr His Leu Val Ser Glu Asp Val Lys Trp Pro Asn Gly Ile Ser Val
                    915                 920                 925

Asp Asp Gln Trp Ile Tyr Trp Thr Asp Ala Tyr Leu Glu Cys Ile Glu
930                 935                 940

Arg Ile Thr Phe Ser Gly Gln Gln Arg Ser Val Ile Leu Asp Asn Leu
945                 950                 955                 960

Pro His Pro Tyr Ala Ile Ala Val Phe Lys Asn Glu Ile Tyr Trp Asp
                    965                 970                 975

Asp Trp Ser Gln Leu Ser Ile Phe Arg Ala Ser Lys Tyr Ser Gly Ser
                    980                 985                 990

Gln Met Glu Ile Leu Ala Asn Gln Leu Thr Gly Leu Met Asp Met Lys
                    995                 1000                1005

Ile Phe Tyr Lys Gly Lys Asn Thr Gly Ser Asn Ala Cys Val Pro
    1010                1015                1020

Arg Pro Cys Ser Leu Leu Cys Leu Pro Lys Ala Asn Asn Ser Arg
    1025                1030                1035

Ser Cys Arg Cys Pro Glu Asp Val Ser Ser Val Leu Pro Ser
    1040                1045                1050

Gly Asp Leu Met Cys Asp Cys Pro Gln Gly Tyr Gln Leu Lys Asn
    1055                1060                1065

Asn Thr Cys Val Lys Glu Glu Asn Thr Cys Leu Arg Asn Gln Tyr
    1070                1075                1080

Arg Cys Ser Asn Gly Asn Cys Ile Asn Ser Ile Trp Trp Cys Asp
    1085                1090                1095

Phe Asp Asn Asp Cys Gly Asp Met Ser Asp Glu Arg Asn Cys Pro
    1100                1105                1110

Thr Thr Ile Cys Asp Leu Asp Thr Gln Phe Arg Cys Gln Glu Ser
    1115                1120                1125

Gly Thr Cys Ile Pro Leu Ser Tyr Lys Cys Asp Leu Glu Asp Asp
    1130                1135                1140

Cys Gly Asp Asn Ser Asp Glu Ser His Cys Glu Met His Gln Cys
    1145                1150                1155

Arg Ser Asp Glu Tyr Asn Cys Ser Ser Gly Met Cys Ile Arg Ser
    1160                1165                1170
```

-continued

Ser Trp Val Cys Asp Gly Asp Asn Asp Cys Arg Asp Trp Ser Asp
1175                 1180                1185

Glu Ala Asn Cys Thr Ala Ile Tyr His Thr Cys Glu Ala Ser Asn
1190                 1195                1200

Phe Gln Cys Arg Asn Gly His Cys Ile Pro Gln Arg Trp Ala Cys
1205                 1210                1215

Asp Gly Asp Thr Asp Cys Gln Asp Gly Ser Asp Glu Asp Pro Val
1220                 1225                1230

Asn Cys Glu Lys Lys Cys Asn Gly Phe Arg Cys Pro Asn Gly Thr
1235                 1240                1245

Cys Ile Pro Ser Ser Lys His Cys Asp Gly Leu Arg Asp Cys Ser
1250                 1255                1260

Asp Gly Ser Asp Glu Gln His Cys Glu Pro Leu Cys Thr His Phe
1265                 1270                1275

Met Asp Phe Val Cys Lys Asn Arg Gln Gln Cys Leu Phe His Ser
1280                 1285                1290

Met Val Cys Asp Gly Ile Ile Gln Cys Arg Asp Gly Ser Asp Glu
1295                 1300                1305

Asp Ala Ala Phe Ala Gly Cys Ser Gln Asp Pro Glu Phe His Lys
1310                 1315                1320

Val Cys Asp Glu Phe Gly Phe Gln Cys Gln Asn Gly Val Cys Ile
1325                 1330                1335

Ser Leu Ile Trp Lys Cys Asp Gly Met Asp Asp Cys Gly Asp Tyr
1340                 1345                1350

Ser Asp Glu Ala Asn Cys Glu Asn Pro Thr Glu Ala Pro Asn Cys
1355                 1360                1365

Ser Arg Tyr Phe Gln Phe Arg Cys Glu Asn Gly His Cys Ile Pro
1370                 1375                1380

Asn Arg Trp Lys Cys Asp Arg Glu Asn Asp Cys Gly Asp Trp Ser
1385                 1390                1395

Asp Glu Lys Asp Cys Gly Asp Ser His Ile Leu Pro Phe Ser Thr
1400                 1405                1410

Pro Gly Pro Ser Thr Cys Leu Pro Asn Tyr Tyr Arg Cys Ser Ser
1415                 1420                1425

Gly Thr Cys Val Met Asp Thr Trp Val Cys Asp Gly Tyr Arg Asp
1430                 1435                1440

Cys Ala Asp Gly Ser Asp Glu Glu Ala Cys Pro Leu Leu Ala Asn
1445                 1450                1455

Val Thr Ala Ala Ser Thr Pro Thr Gln Leu Gly Arg Cys Asp Arg
1460                 1465                1470

Phe Glu Phe Glu Cys His Gln Pro Lys Thr Cys Ile Pro Asn Trp
1475                 1480                1485

Lys Arg Cys Asp Gly His Gln Asp Cys Gln Asp Gly Arg Asp Glu
1490                 1495                1500

Ala Asn Cys Pro Thr His Ser Thr Leu Thr Cys Met Ser Arg Glu
1505                 1510                1515

Phe Gln Cys Glu Asp Gly Glu Ala Cys Ile Val Leu Ser Glu Arg
1520                 1525                1530

Cys Asp Gly Phe Leu Asp Cys Ser Asp Glu Ser Asp Glu Lys Ala
1535                 1540                1545

Cys Ser Asp Glu Leu Thr Val Tyr Lys Val Gln Asn Leu Gln Trp
1550                 1555                1560

```
Thr Ala Asp Phe Ser Gly Asp Val Thr Leu Thr Trp Met Arg Pro
1565                1570                1575

Lys Lys Met Pro Ser Ala Ser Cys Val Tyr Asn Val Tyr Tyr Arg
1580                1585                1590

Val Val Gly Glu Ser Ile Trp Lys Thr Leu Glu Thr His Ser Asn
1595                1600                1605

Lys Thr Asn Thr Val Leu Lys Val Leu Lys Pro Asp Thr Thr Tyr
1610                1615                1620

Gln Val Lys Val Gln Val Gln Cys Leu Ser Lys Ala His Asn Thr
1625                1630                1635

Asn Asp Phe Val Thr Leu Arg Thr Pro Glu Gly Leu Pro Asp Ala
1640                1645                1650

Pro Arg Asn Leu Gln Leu Ser Leu Pro Arg Glu Ala Glu Gly Val
1655                1660                1665

Ile Val Gly His Trp Ala Pro Pro Ile His Thr His Gly Leu Ile
1670                1675                1680

Arg Glu Tyr Ile Val Glu Tyr Ser Arg Ser Gly Ser Lys Met Trp
1685                1690                1695

Ala Ser Gln Arg Ala Ala Ser Asn Phe Thr Glu Ile Lys Asn Leu
1700                1705                1710

Leu Val Asn Thr Leu Tyr Thr Val Arg Val Ala Ala Val Thr Ser
1715                1720                1725

Arg Gly Ile Gly Asn Trp Ser Asp Ser Lys Ser Ile Thr Thr Ile
1730                1735                1740

Lys Gly Lys Val Ile Pro Pro Pro Asp Ile His Ile Asp Ser Tyr
1745                1750                1755

Gly Glu Asn Tyr Leu Ser Phe Thr Leu Thr Met Glu Ser Asp Ile
1760                1765                1770

Lys Val Asn Gly Tyr Val Val Asn Leu Phe Trp Ala Phe Asp Thr
1775                1780                1785

His Lys Gln Glu Arg Arg Thr Leu Asn Phe Arg Gly Ser Ile Leu
1790                1795                1800

Ser His Lys Val Gly Asn Leu Thr Ala His Thr Ser Tyr Glu Ile
1805                1810                1815

Ser Ala Trp Ala Lys Thr Asp Leu Gly Asp Ser Pro Leu Ala Phe
1820                1825                1830

Glu His Val Met Thr Arg Gly Val Arg Pro Pro Ala Pro Ser Leu
1835                1840                1845

Lys Ala Lys Ala Ile Asn Gln Thr Ala Val Glu Cys Thr Trp Thr
1850                1855                1860

Gly Pro Arg Asn Val Val Tyr Gly Ile Phe Tyr Ala Thr Ser Phe
1865                1870                1875

Leu Asp Leu Tyr Arg Asn Pro Lys Ser Leu Thr Thr Ser Leu His
1880                1885                1890

Asn Lys Thr Val Ile Val Ser Lys Asp Glu Gln Tyr Leu Phe Leu
1895                1900                1905

Val Arg Val Val Val Pro Tyr Gln Gly Pro Ser Ser Asp Tyr Val
1910                1915                1920

Val Val Lys Met Ile Pro Asp Ser Arg Leu Pro Pro Arg His Leu
1925                1930                1935

His Val Val His Thr Gly Lys Thr Ser Val Val Ile Lys Trp Glu
1940                1945                1950

Ser Pro Tyr Asp Ser Pro Asp Gln Asp Leu Leu Tyr Ala Ile Ala
```

-continued

```
               1955                1960                1965

Val Lys Asp Leu Ile Arg Lys Thr Asp Arg Ser Tyr Lys Val Lys
    1970                1975                1980

Ser Arg Asn Ser Thr Val Glu Tyr Thr Leu Asn Lys Leu Glu Pro
    1985                1990                1995

Gly Gly Lys Tyr His Ile Ile Val Gln Leu Gly Asn Met Ser Lys
    2000                2005                2010

Asp Ser Ser Ile Lys Ile Thr Thr Val Ser Leu Ser Ala Pro Asp
    2015                2020                2025

Ala Leu Lys Ile Ile Thr Glu Asn Asp His Val Leu Leu Phe Trp
    2030                2035                2040

Lys Ser Leu Ala Leu Lys Glu Lys His Phe Asn Glu Ser Arg Gly
    2045                2050                2055

Tyr Glu Ile His Met Phe Asp Ser Ala Met Asn Ile Thr Ala Tyr
    2060                2065                2070

Leu Gly Asn Thr Thr Asp Asn Phe Phe Lys Ile Ser Asn Leu Lys
    2075                2080                2085

Met Gly His Asn Tyr Thr Phe Thr Val Gln Ala Arg Cys Leu Phe
    2090                2095                2100

Gly Asn Gln Ile Cys Gly Glu Pro Ala Ile Leu Leu Tyr Asp Glu
    2105                2110                2115

Leu Gly Ser Gly Ala Asp Ala Ser Ala Thr Gln Ala Ala Arg Ser
    2120                2125                2130

Thr Asp Val Ala Ala Val Val Pro Ile Leu Phe Leu Ile Leu
    2135                2140                2145

Leu Ser Leu Gly Val Gly Phe Ala Ile Leu Tyr Thr Lys His Arg
    2150                2155                2160

Arg Leu Gln Ser Ser Phe Thr Ala Phe Ala Asn Ser His Tyr Ser
    2165                2170                2175

Ser Arg Leu Gly Ser Ala Ile Phe Ser Ser Gly Asp Asp Leu Gly
    2180                2185                2190

Glu Asp Asp Glu Asp Ala Pro Met Ile Thr Gly Phe Ser Asp Asp
    2195                2200                2205

Val Pro Met Val Ile Ala
    2210

<210> SEQ ID NO 3
<211> LENGTH: 1168
<212> TYPE: PRT
<213> ORGANISM: Homo Sapiens

<400> SEQUENCE: 3

Met Gly Lys Val Gly Ala Gly Gly Ser Gln Ala Arg Leu Ser Ala
1               5                   10                  15

Leu Leu Ala Gly Ala Gly Leu Leu Ile Leu Cys Ala Pro Gly Val Cys
                20                  25                  30

Gly Gly Gly Ser Cys Cys Pro Ser Pro His Pro Ser Ala Pro Arg
            35                  40                  45

Ser Ala Ser Thr Pro Arg Gly Phe Ser His Gln Gly Arg Pro Gly Arg
    50                  55                  60

Ala Pro Ala Thr Pro Leu Pro Leu Val Val Arg Pro Leu Phe Ser Val
65                  70                  75                  80

Ala Pro Gly Asp Arg Ala Leu Ser Leu Glu Arg Ala Arg Gly Thr Gly
                85                  90                  95
```

```
Ala Ser Met Ala Val Ala Ala Arg Ser Gly Arg Arg Arg Ser Gly
            100                 105                 110
Ala Asp Gln Glu Lys Ala Glu Arg Gly Glu Gly Ala Ser Arg Ser Pro
        115                 120                 125
Arg Gly Val Leu Arg Asp Gly Gln Gln Glu Pro Gly Thr Arg Glu
    130                 135                 140
Arg Asp Pro Asp Lys Ala Thr Arg Phe Arg Met Glu Glu Leu Arg Leu
145                 150                 155                 160
Thr Ser Thr Thr Phe Ala Leu Thr Gly Asp Ser Ala His Asn Gln Ala
                165                 170                 175
Met Val His Trp Ser Gly His Asn Ser Ser Val Ile Leu Ile Leu Thr
            180                 185                 190
Lys Leu Tyr Asp Tyr Asn Leu Gly Ser Ile Thr Glu Ser Ser Leu Trp
        195                 200                 205
Arg Ser Thr Asp Tyr Gly Thr Thr Tyr Glu Lys Leu Asn Asp Lys Val
    210                 215                 220
Gly Leu Lys Thr Ile Leu Gly Tyr Leu Tyr Val Cys Pro Thr Asn Lys
225                 230                 235                 240
Arg Lys Ile Met Leu Leu Thr Asp Pro Glu Ile Glu Ser Ser Leu Leu
                245                 250                 255
Ile Ser Ser Asp Glu Gly Ala Thr Tyr Gln Lys Tyr Arg Leu Asn Phe
            260                 265                 270
Tyr Ile Gln Ser Leu Leu Phe His Pro Lys Gln Glu Asp Trp Ile Leu
        275                 280                 285
Ala Tyr Ser Gln Asp Gln Lys Leu Tyr Ser Ser Ala Glu Phe Gly Arg
    290                 295                 300
Arg Trp Gln Leu Ile Gln Glu Gly Val Val Pro Asn Arg Phe Tyr Trp
305                 310                 315                 320
Ser Val Met Gly Ser Asn Lys Glu Pro Asp Leu Val His Leu Glu Ala
                325                 330                 335
Arg Thr Val Asp Gly His Ser His Tyr Leu Thr Cys Arg Met Gln Asn
            340                 345                 350
Cys Thr Glu Ala Asn Arg Asn Gln Pro Phe Pro Gly Tyr Ile Asp Pro
        355                 360                 365
Asp Ser Leu Ile Val Gln Asp His Tyr Val Phe Val Gln Leu Thr Ser
    370                 375                 380
Gly Gly Arg Pro His Tyr Tyr Val Ser Tyr Arg Arg Asn Ala Phe Ala
385                 390                 395                 400
Gln Met Lys Leu Pro Lys Tyr Ala Leu Pro Lys Asp Met His Val Ile
                405                 410                 415
Ser Thr Asp Glu Asn Gln Val Phe Ala Ala Val Gln Glu Trp Asn Gln
            420                 425                 430
Asn Asp Thr Tyr Asn Leu Tyr Ile Ser Asp Thr Arg Gly Val Tyr Phe
        435                 440                 445
Thr Leu Ala Leu Glu Asn Val Gln Ser Ser Arg Gly Pro Glu Gly Asn
    450                 455                 460
Ile Met Ile Asp Leu Tyr Glu Val Ala Gly Ile Lys Gly Met Phe Leu
465                 470                 475                 480
Ala Asn Lys Lys Ile Asp Tyr Gln Val Lys Thr Phe Ile Thr Tyr Asn
                485                 490                 495
Lys Gly Arg Asp Trp Arg Leu Leu Gln Ala Pro Asp Thr Asp Leu Arg
            500                 505                 510
Gly Asp Pro Val His Cys Leu Leu Pro Tyr Cys Ser Leu His Leu His
```

```
                515                 520                 525
Leu Lys Val Ser Glu Asn Pro Tyr Thr Ser Gly Ile Ile Ala Ser Lys
            530                 535                 540

Asp Thr Ala Pro Ser Ile Ile Val Ala Ser Gly Asn Ile Gly Ser Glu
545                 550                 555                 560

Leu Ser Asp Thr Asp Ile Ser Met Phe Val Ser Ser Asp Ala Gly Asn
                565                 570                 575

Thr Trp Arg Gln Ile Phe Glu Glu His Ser Val Leu Tyr Leu Asp
                580                 585                 590

Gln Gly Gly Val Leu Val Ala Met Lys His Thr Ser Leu Pro Ile Arg
            595                 600                 605

His Leu Trp Leu Ser Phe Asp Glu Gly Arg Ser Trp Ser Lys Tyr Ser
            610                 615                 620

Phe Thr Ser Ile Pro Leu Phe Val Asp Gly Val Leu Gly Glu Pro Gly
625                 630                 635                 640

Glu Glu Thr Leu Ile Met Thr Val Phe Gly His Phe Ser His Arg Ser
                645                 650                 655

Glu Trp Gln Leu Val Lys Val Asp Tyr Lys Ser Ile Phe Asp Arg Arg
            660                 665                 670

Cys Ala Glu Glu Asp Tyr Arg Pro Trp Gln Leu His Ser Gln Gly Glu
            675                 680                 685

Ala Cys Ile Met Gly Ala Lys Arg Ile Tyr Lys Lys Arg Lys Ser Glu
690                 695                 700

Arg Lys Cys Met Gln Gly Lys Tyr Ala Gly Ala Met Glu Ser Glu Pro
705                 710                 715                 720

Cys Val Cys Thr Glu Ala Asp Phe Asp Cys Asp Tyr Gly Tyr Glu Arg
                725                 730                 735

His Ser Asn Gly Gln Cys Leu Pro Ala Phe Trp Phe Asn Pro Ser Ser
            740                 745                 750

Leu Ser Lys Asp Cys Ser Leu Gly Gln Ser Tyr Leu Asn Ser Thr Gly
            755                 760                 765

Tyr Arg Lys Val Val Ser Asn Asn Cys Thr Asp Gly Val Arg Glu Gln
            770                 775                 780

Tyr Thr Ala Lys Pro Gln Lys Cys Pro Gly Lys Ala Pro Arg Gly Leu
785                 790                 795                 800

Arg Ile Val Thr Ala Asp Gly Lys Leu Thr Ala Glu Gln Gly His Asn
                805                 810                 815

Val Thr Leu Met Val Gln Leu Glu Glu Gly Asp Val Gln Arg Thr Leu
                820                 825                 830

Ile Gln Val Asp Phe Gly Asp Gly Ile Ala Val Ser Tyr Val Asn Leu
            835                 840                 845

Ser Ser Met Glu Asp Gly Ile Lys His Val Tyr Gln Asn Val Gly Ile
            850                 855                 860

Phe Arg Val Thr Val Gln Val Asp Asn Ser Leu Gly Ser Asp Ser Ala
865                 870                 875                 880

Val Leu Tyr Leu His Val Thr Cys Pro Leu Glu His Val His Leu Ser
                885                 890                 895

Leu Pro Phe Val Thr Thr Lys Asn Lys Glu Val Asn Ala Thr Ala Val
                900                 905                 910

Leu Trp Pro Ser Gln Val Gly Thr Leu Thr Tyr Val Trp Trp Tyr Gly
            915                 920                 925

Asn Asn Thr Glu Pro Leu Ile Thr Leu Glu Gly Ser Ile Ser Phe Arg
            930                 935                 940
```

```
Phe Thr Ser Glu Gly Met Asn Thr Ile Thr Val Gln Val Ser Ala Gly
945                 950                 955                 960

Asn Ala Ile Leu Gln Asp Thr Lys Thr Ile Ala Val Tyr Glu Glu Phe
                965                 970                 975

Arg Ser Leu Arg Leu Ser Phe Ser Pro Asn Leu Asp Asp Tyr Asn Pro
            980                 985                 990

Asp Ile Pro Glu Trp Arg Arg Asp Ile Gly Arg Val Ile Lys Lys Ser
        995                 1000                1005

Leu Val Glu Ala Thr Gly Val Pro Gly Gln His Ile Leu Val Ala
    1010                1015                1020

Val Leu Pro Gly Leu Pro Thr Thr Ala Glu Leu Phe Val Leu Pro
    1025                1030                1035

Tyr Gln Asp Pro Ala Gly Glu Asn Lys Arg Ser Thr Asp Asp Leu
    1040                1045                1050

Glu Gln Ile Ser Glu Leu Leu Ile His Thr Leu Asn Gln Asn Ser
    1055                1060                1065

Val His Phe Glu Leu Lys Pro Gly Val Arg Val Leu Val His Ala
    1070                1075                1080

Ala His Leu Thr Ala Ala Pro Leu Val Asp Leu Thr Pro Thr His
    1085                1090                1095

Ser Gly Ser Ala Met Leu Met Leu Leu Ser Val Val Phe Val Gly
    1100                1105                1110

Leu Ala Val Phe Val Ile Tyr Lys Phe Lys Arg Arg Val Ala Leu
    1115                1120                1125

Pro Ser Pro Pro Ser Pro Ser Thr Gln Pro Gly Asp Ser Ser Leu
    1130                1135                1140

Arg Leu Gln Arg Ala Arg His Ala Thr Pro Pro Ser Thr Pro Lys
    1145                1150                1155

Arg Gly Ser Ala Gly Ala Gln Tyr Ala Ile
    1160                1165

<210> SEQ ID NO 4
<211> LENGTH: 907
<212> TYPE: PRT
<213> ORGANISM: Homo Sapiens

<400> SEQUENCE: 4

Leu Ile Phe His Pro Lys Glu Glu Asp Lys Val Leu Ala Tyr Thr Lys
1               5                   10                  15

Glu Ser Lys Leu Tyr Val Ser Ser Asp Leu Gly Lys Lys Trp Thr Leu
            20                  25                  30

Leu Gln Glu Arg Val Thr Lys Asp His Val Phe Trp Ser Val Ser Gly
        35                  40                  45

Val Asp Ala Asp Pro Asp Leu Val His Val Glu Ala Gln Asp Leu Gly
    50                  55                  60

Gly Asp Phe Arg Tyr Val Thr Cys Ala Ile His Asn Cys Ser Glu Lys
65                  70                  75                  80

Met Leu Thr Ala Pro Phe Ala Gly Pro Ile Asp His Gly Ser Leu Thr
                85                  90                  95

Val Gln Asp Asp Tyr Ile Phe Phe Lys Ala Thr Ser Ala Asn Gln Thr
            100                 105                 110

Lys Tyr Tyr Val Ser Tyr Arg Arg Asn Glu Phe Val Leu Met Lys Leu
        115                 120                 125

Pro Lys Tyr Ala Leu Pro Lys Asp Leu Gln Ile Ile Ser Thr Asp Glu
```

```
            130                 135                 140
Ser Gln Val Phe Val Ala Val Gln Glu Trp Tyr Gln Met Asp Thr Tyr
145                 150                 155                 160

Asn Leu Tyr Gln Ser Asp Pro Arg Gly Val Arg Tyr Ala Leu Val Leu
                165                 170                 175

Gln Asp Val Arg Ser Ser Arg Gln Ala Glu Ser Val Leu Ile Asp
            180                 185                 190

Ile Leu Glu Val Arg Gly Val Lys Gly Val Phe Leu Ala Asn Gln Lys
            195                 200                 205

Ile Asp Gly Lys Val Met Thr Leu Ile Thr Tyr Asn Lys Gly Arg Asp
        210                 215                 220

Trp Asp Tyr Leu Arg Pro Pro Ser Met Asp Met Asn Gly Lys Pro Thr
225                 230                 235                 240

Asn Cys Lys Pro Pro Asp Cys His Leu His Leu His Leu Arg Trp Ala
                245                 250                 255

Asp Asn Pro Tyr Val Ser Gly Thr Val His Thr Lys Asp Thr Ala Pro
                260                 265                 270

Gly Leu Ile Met Gly Ala Gly Asn Leu Gly Ser Gln Leu Val Glu Tyr
            275                 280                 285

Lys Glu Glu Met Tyr Ile Thr Ser Asp Cys Gly His Thr Trp Arg Gln
            290                 295                 300

Val Phe Glu Glu Glu His His Ile Leu Tyr Leu Asp His Gly Gly Val
305                 310                 315                 320

Ile Val Ala Ile Lys Asp Thr Ser Ile Pro Leu Lys Ile Leu Lys Phe
                325                 330                 335

Ser Val Asp Glu Gly Leu Thr Trp Ser Thr His Asn Phe Thr Ser Thr
                340                 345                 350

Ser Val Phe Val Asp Gly Leu Leu Ser Glu Pro Gly Asp Glu Thr Leu
            355                 360                 365

Val Met Thr Val Phe Gly His Ile Ser Phe Arg Ser Asp Trp Glu Leu
        370                 375                 380

Val Lys Val Asp Phe Arg Pro Ser Phe Ser Arg Gln Cys Gly Glu Glu
385                 390                 395                 400

Asp Tyr Ser Ser Trp Glu Leu Ser Asn Leu Gln Gly Asp Arg Cys Ile
                405                 410                 415

Met Gly Gln Gln Arg Ser Phe Arg Lys Arg Lys Ser Thr Ser Trp Cys
            420                 425                 430

Ile Lys Gly Arg Ser Phe Thr Ser Ala Leu Thr Ser Arg Val Cys Glu
        435                 440                 445

Cys Arg Asp Ser Asp Phe Leu Cys Asp Tyr Gly Phe Glu Arg Ser Pro
    450                 455                 460

Ser Ser Glu Ser Ser Thr Asn Lys Cys Ser Ala Asn Phe Trp Phe Asn
465                 470                 475                 480

Pro Leu Ser Pro Pro Asp Asp Cys Ala Leu Gly Gln Thr Tyr Thr Ser
                485                 490                 495

Ser Leu Gly Tyr Arg Lys Val Val Ser Asn Val Cys Glu Gly Gly Val
            500                 505                 510

Asp Met Gln Gln Ser Gln Val Gln Leu Gln Cys Pro Leu Thr Pro Pro
        515                 520                 525

Arg Gly Leu Gln Val Ser Ile Gln Gly Glu Ala Val Ala Val Arg Pro
    530                 535                 540

Gly Glu Asp Val Leu Phe Val Val Arg Gln Glu Gln Gly Asp Val Leu
545                 550                 555                 560
```

```
Thr Thr Lys Tyr Gln Val Asp Leu Gly Asp Gly Phe Lys Ala Met Tyr
            565                 570                 575

Val Asn Leu Thr Leu Thr Gly Glu Pro Ile Arg His Arg Tyr Glu Ser
            580                 585                 590

Pro Gly Ile Tyr Arg Val Ser Val Arg Ala Glu Asn Thr Ala Gly His
            595                 600                 605

Asp Glu Ala Val Leu Phe Val Gln Val Asn Ser Pro Leu Gln Ala Leu
            610                 615                 620

Tyr Leu Glu Val Val Pro Val Ile Gly Leu Asn Gln Glu Val Asn Leu
625                 630                 635                 640

Thr Ala Val Leu Leu Pro Leu Asn Pro Asn Leu Thr Val Phe Tyr Trp
            645                 650                 655

Trp Ile Gly His Ser Leu Gln Pro Leu Leu Ser Leu Asp Asn Ser Val
            660                 665                 670

Thr Thr Arg Phe Ser Asp Thr Gly Asp Val Arg Val Thr Val Gln Ala
            675                 680                 685

Ala Cys Gly Asn Ser Val Leu Gln Asp Ser Arg Val Leu Arg Val Leu
            690                 695                 700

Asp Gln Phe Gln Val Met Pro Leu Gln Phe Ser Lys Glu Leu Asp Ala
705                 710                 715                 720

Tyr Asn Pro Asn Thr Pro Glu Trp Arg Glu Asp Val Gly Leu Val Val
            725                 730                 735

Thr Arg Leu Leu Ser Lys Glu Thr Ser Val Pro Gln Glu Leu Leu Val
            740                 745                 750

Thr Val Val Lys Pro Gly Leu Pro Thr Leu Ala Asp Leu Tyr Val Leu
            755                 760                 765

Leu Pro Pro Pro Arg Pro Thr Arg Lys Arg Ser Leu Ser Ser Asp Lys
770                 775                 780

Arg Leu Ala Ala Ile Gln Gln Val Leu Asn Ala Gln Lys Ile Ser Phe
785                 790                 795                 800

Leu Leu Arg Gly Gly Val Arg Val Leu Val Ala Leu Arg Asp Thr Gly
            805                 810                 815

Thr Gly Ala Glu Gln Leu Gly Gly Gly Gly Tyr Trp Ala Val Val
            820                 825                 830

Val Leu Phe Val Ile Gly Leu Phe Ala Ala Gly Ala Phe Ile Leu Tyr
            835                 840                 845

Lys Phe Lys Arg Lys Arg Pro Gly Arg Thr Val Tyr Ala Gln Met His
850                 855                 860

Asn Glu Lys Glu Gln Glu Met Thr Ser Pro Val Ser His Ser Glu Asp
865                 870                 875                 880

Val Gln Gly Ala Val Gln Gly Asn His Ser Gly Val Val Leu Ser Ile
            885                 890                 895

Asn Ser Arg Glu Met His Ser Tyr Leu Val Ser
            900                 905

<210> SEQ ID NO 5
<211> LENGTH: 1222
<212> TYPE: PRT
<213> ORGANISM: Homo Sapiens

<400> SEQUENCE: 5

Met Glu Ala Ala Arg Thr Glu Arg Pro Ala Gly Arg Pro Gly Ala Pro
1               5                   10                  15

Leu Val Arg Thr Gly Leu Leu Leu Leu Ser Thr Trp Val Leu Ala Gly
```

-continued

```
                20                  25                  30
Ala Glu Ile Thr Trp Asp Ala Thr Gly Gly Pro Gly Arg Pro Ala Ala
            35                  40                  45
Pro Ala Ser Arg Pro Ala Leu Ser Pro Leu Ser Pro Arg Ala Val
    50                  55                  60
Ala Ser Gln Trp Pro Glu Glu Leu Ala Ser Ala Arg Arg Ala Ala Val
65                  70                  75                  80
Leu Gly Arg Arg Ala Gly Pro Glu Leu Leu Pro Gln Gln Gly Gly
                85                  90                  95
Arg Gly Gly Glu Met Gln Val Glu Ala Gly Gly Thr Ser Pro Ala Gly
                100                 105                 110
Glu Arg Arg Gly Arg Gly Ile Pro Ala Pro Ala Lys Leu Gly Gly Ala
            115                 120                 125
Arg Arg Ser Arg Arg Ala Gln Pro Pro Ile Thr Gln Glu Arg Gly Asp
            130                 135                 140
Ala Trp Ala Thr Ala Pro Ala Asp Gly Ser Arg Gly Ser Arg Pro Leu
145                 150                 155                 160
Ala Lys Gly Ser Arg Glu Glu Val Lys Ala Pro Arg Ala Gly Gly Ser
                165                 170                 175
Ala Ala Glu Asp Leu Arg Leu Pro Ser Thr Ser Phe Ala Leu Thr Gly
            180                 185                 190
Asp Ser Ala His Asn Gln Ala Met Val His Trp Ser Gly His Asn Ser
            195                 200                 205
Ser Val Ile Leu Ile Leu Thr Lys Leu Tyr Asp Phe Asn Leu Gly Ser
    210                 215                 220
Val Thr Glu Ser Ser Leu Trp Arg Ser Thr Asp Tyr Gly Thr Thr Tyr
225                 230                 235                 240
Glu Lys Leu Asn Asp Lys Val Gly Leu Lys Thr Val Leu Ser Tyr Leu
                245                 250                 255
Tyr Val Asn Pro Thr Asn Lys Arg Lys Ile Met Leu Leu Ser Asp Pro
                260                 265                 270
Glu Met Glu Ser Ser Ile Leu Ile Ser Ser Asp Glu Gly Ala Thr Tyr
            275                 280                 285
Gln Lys Tyr Arg Leu Thr Phe Tyr Ile Gln Ser Leu Leu Phe His Pro
            290                 295                 300
Lys Gln Glu Asp Trp Val Leu Ala Tyr Ser Leu Asp Gln Lys Leu Tyr
305                 310                 315                 320
Ser Ser Met Asp Phe Gly Arg Arg Trp Gln Leu Met His Glu Arg Ile
                325                 330                 335
Thr Pro Asn Arg Phe Tyr Trp Ser Val Ala Gly Leu Asp Lys Glu Ala
                340                 345                 350
Asp Leu Val His Met Glu Val Arg Thr Thr Asp Gly Tyr Ala His Tyr
            355                 360                 365
Leu Thr Cys Arg Ile Gln Glu Cys Ala Glu Thr Thr Arg Ser Gly Pro
            370                 375                 380
Phe Ala Arg Ser Ile Asp Ile Ser Ser Leu Val Val Gln Asp Glu Tyr
385                 390                 395                 400
Ile Phe Ile Gln Val Thr Thr Ser Gly Arg Ala Ser Tyr Tyr Val Ser
                405                 410                 415
Tyr Arg Arg Glu Ala Phe Ala Gln Ile Lys Leu Pro Lys Tyr Ser Leu
            420                 425                 430
Pro Lys Asp Met His Ile Ile Ser Thr Asp Glu Asn Gln Val Phe Ala
            435                 440                 445
```

```
Ala Val Gln Glu Trp Asn Gln Asn Asp Thr Tyr Asn Leu Tyr Ile Ser
    450                 455                 460

Asp Thr Arg Gly Ile Tyr Phe Thr Leu Ala Met Glu Asn Ile Lys Ser
465                 470                 475                 480

Ser Arg Gly Leu Met Gly Asn Ile Ile Glu Leu Tyr Glu Val Ala
                    485                 490                 495

Gly Ile Lys Gly Ile Phe Leu Ala Asn Lys Lys Val Asp Asp Gln Val
                    500                 505                 510

Lys Thr Tyr Ile Thr Tyr Asn Lys Gly Arg Asp Trp Arg Leu Leu Gln
                515                 520                 525

Ala Pro Asp Val Asp Leu Arg Gly Ser Pro Val His Cys Leu Leu Pro
530                 535                 540

Phe Cys Ser Leu His Leu His Leu Gln Leu Ser Glu Asn Pro Tyr Ser
545                 550                 555                 560

Ser Gly Arg Ile Ser Ser Lys Glu Thr Ala Pro Gly Leu Val Val Ala
                565                 570                 575

Thr Gly Asn Ile Gly Pro Glu Leu Ser Tyr Thr Asp Ile Gly Val Phe
                580                 585                 590

Ile Ser Ser Asp Gly Gly Asn Thr Trp Arg Gln Ile Phe Asp Glu Glu
                595                 600                 605

Tyr Asn Val Trp Phe Leu Asp Trp Gly Gly Ala Leu Val Ala Met Lys
610                 615                 620

His Thr Pro Leu Pro Val Arg His Leu Trp Val Ser Phe Asp Glu Gly
625                 630                 635                 640

His Ser Trp Asp Lys Tyr Gly Phe Thr Ser Val Pro Leu Phe Val Asp
                645                 650                 655

Gly Ala Leu Val Glu Ala Gly Met Glu Thr His Ile Met Thr Val Phe
                660                 665                 670

Gly His Phe Ser Leu Arg Ser Glu Trp Gln Leu Val Lys Val Asp Tyr
                675                 680                 685

Lys Ser Ile Phe Ser Arg His Cys Thr Lys Glu Asp Tyr Gln Thr Trp
690                 695                 700

His Leu Leu Asn Gln Gly Glu Pro Cys Val Met Gly Glu Arg Lys Ile
705                 710                 715                 720

Phe Lys Lys Arg Lys Pro Gly Ala Gln Cys Ala Leu Gly Arg Asp His
                725                 730                 735

Ser Gly Ser Val Val Ser Glu Pro Cys Val Cys Ala Asn Trp Asp Phe
                740                 745                 750

Glu Cys Asp Tyr Gly Tyr Glu Arg His Gly Glu Ser Gln Cys Val Pro
                755                 760                 765

Ala Phe Trp Tyr Asn Pro Ala Ser Pro Ser Lys Asp Cys Ser Leu Gly
770                 775                 780

Gln Ser Tyr Leu Asn Ser Thr Gly Tyr Arg Arg Ile Val Ser Asn Asn
785                 790                 795                 800

Cys Thr Asp Gly Leu Arg Glu Lys Tyr Thr Ala Lys Ala Gln Met Cys
                805                 810                 815

Pro Gly Lys Ala Pro Arg Gly Leu His Val Val Thr Thr Asp Gly Arg
                820                 825                 830

Leu Val Ala Glu Gln Gly His Asn Ala Thr Phe Ile Ile Leu Met Glu
                835                 840                 845

Glu Gly Asp Leu Gln Arg Thr Asn Ile Gln Leu Asp Phe Gly Asp Gly
                850                 855                 860
```

```
Ile Ala Val Ser Tyr Ala Asn Phe Ser Pro Ile Glu Asp Gly Ile Lys
865                 870                 875                 880

His Val Tyr Lys Ser Ala Gly Ile Phe Gln Val Thr Ala Tyr Ala Glu
            885                 890                 895

Asn Asn Leu Gly Ser Asp Thr Ala Val Leu Phe Leu His Val Val Cys
        900                 905                 910

Pro Val Glu His Val His Leu Arg Val Pro Phe Val Ala Ile Arg Asn
        915                 920                 925

Lys Glu Val Asn Ile Ser Ala Val Val Trp Pro Ser Gln Leu Gly Thr
        930                 935                 940

Leu Thr Tyr Phe Trp Trp Phe Gly Asn Ser Thr Lys Pro Leu Ile Thr
945                 950                 955                 960

Leu Asp Ser Ser Ile Ser Phe Thr Phe Leu Ala Glu Gly Thr Asp Thr
            965                 970                 975

Ile Thr Val Gln Val Ala Ala Gly Asn Ala Leu Ile Gln Asp Thr Lys
        980                 985                 990

Glu Ile Ala Val His Glu Tyr Phe Gln Ser Gln Leu Leu Ser Phe Ser
        995                 1000                1005

Pro Asn Leu Asp Tyr His Asn Pro Asp Ile Pro Glu Trp Arg Lys
    1010                1015                1020

Asp Ile Gly Asn Val Ile Lys Arg Ala Leu Val Lys Val Thr Ser
    1025                1030                1035

Val Pro Glu Asp Gln Ile Leu Ile Ala Val Phe Pro Gly Leu Pro
    1040                1045                1050

Thr Ser Ala Glu Leu Phe Ile Leu Pro Pro Lys Asn Leu Thr Glu
    1055                1060                1065

Arg Arg Lys Gly Asn Glu Gly Asp Leu Glu Gln Ile Val Glu Thr
    1070                1075                1080

Leu Phe Asn Ala Leu Asn Gln Asn Leu Val Gln Phe Glu Leu Lys
    1085                1090                1095

Pro Gly Val Gln Val Ile Val Tyr Val Thr Gln Leu Thr Leu Ala
    1100                1105                1110

Pro Leu Val Asp Ser Ser Ala Gly His Ser Ser Ser Ala Met Leu
    1115                1120                1125

Met Leu Leu Ser Val Val Phe Val Gly Leu Ala Val Phe Leu Ile
    1130                1135                1140

Tyr Lys Phe Lys Arg Lys Ile Pro Trp Ile Asn Ile Tyr Ala Gln
    1145                1150                1155

Val Gln His Asp Lys Glu Gln Glu Met Ile Gly Ser Val Ser Gln
    1160                1165                1170

Ser Glu Asn Ala Pro Lys Ile Thr Leu Ser Asp Phe Thr Glu Pro
    1175                1180                1185

Glu Glu Leu Leu Asp Lys Glu Leu Asp Thr Arg Val Ile Gly Gly
    1190                1195                1200

Ile Ala Thr Ile Ala Asn Ser Glu Ser Thr Lys Glu Ile Pro Asn
    1205                1210                1215

Cys Thr Ser Val
    1220

<210> SEQ ID NO 6
<211> LENGTH: 241
<212> TYPE: PRT
<213> ORGANISM: Homo sapiens
<220> FEATURE:
<221> NAME/KEY: SIGNAL
```

```
<222> LOCATION: (1)..(18)
<223> OTHER INFORMATION: Signal peptide of NGF
<220> FEATURE:
<221> NAME/KEY: PROPEP
<222> LOCATION: (19)..(121)
<223> OTHER INFORMATION: Propeptide of NGF (NGFpro)
<220> FEATURE:
<221> NAME/KEY: MISC_FEATURE
<222> LOCATION: (19)..(241)
<223> OTHER INFORMATION: proNGF
<220> FEATURE:
<221> NAME/KEY: MISC_FEATURE
<222> LOCATION: (122)..(241)
<223> OTHER INFORMATION: Mature NGF

<400> SEQUENCE: 6

Met Ser Met Leu Phe Tyr Thr Leu Ile Thr Ala Phe Leu Ile Gly Ile
1               5                   10                  15

Gln Ala Glu Pro His Ser Glu Ser Asn Val Pro Ala Gly His Thr Ile
            20                  25                  30

Pro Gln Val His Trp Thr Lys Leu Gln His Ser Leu Asp Thr Ala Leu
        35                  40                  45

Arg Arg Ala Arg Ser Ala Pro Ala Ala Ala Ile Ala Ala Arg Val Ala
50                  55                  60

Gly Gln Thr Arg Asn Ile Thr Val Asp Pro Arg Leu Phe Lys Lys Arg
65                  70                  75                  80

Arg Leu Arg Ser Pro Arg Val Leu Phe Ser Thr Gln Pro Pro Arg Glu
                85                  90                  95

Ala Ala Asp Thr Gln Asp Leu Asp Phe Glu Val Gly Gly Ala Ala Pro
            100                 105                 110

Phe Asn Arg Thr His Arg Ser Lys Arg Ser Ser Ser His Pro Ile Phe
        115                 120                 125

His Arg Gly Glu Phe Ser Val Cys Asp Ser Val Ser Val Trp Val Gly
    130                 135                 140

Asp Lys Thr Thr Ala Thr Asp Ile Lys Gly Lys Glu Val Met Val Leu
145                 150                 155                 160

Gly Glu Val Asn Ile Asn Asn Ser Val Phe Lys Gln Tyr Phe Phe Glu
                165                 170                 175

Thr Lys Cys Arg Asp Pro Asn Pro Val Asp Ser Gly Cys Arg Gly Ile
            180                 185                 190

Asp Ser Lys His Trp Asn Ser Tyr Cys Thr Thr Thr His Thr Phe Val
        195                 200                 205

Lys Ala Leu Thr Met Asp Gly Lys Gln Ala Ala Trp Arg Phe Ile Arg
    210                 215                 220

Ile Asp Thr Ala Cys Val Cys Val Leu Ser Arg Lys Ala Val Arg Arg
225                 230                 235                 240

Ala

<210> SEQ ID NO 7
<211> LENGTH: 246
<212> TYPE: PRT
<213> ORGANISM: Homo sapiens
<220> FEATURE:
<221> NAME/KEY: SIGNAL
<222> LOCATION: (1)..(18)
<223> OTHER INFORMATION: Signal peptide of BDNF
<220> FEATURE:
<221> NAME/KEY: PROPEP
<222> LOCATION: (19)..(127)
<223> OTHER INFORMATION: Propeptide of BDNF (BDNFpro)
<220> FEATURE:
<221> NAME/KEY: MISC_FEATURE
```

<222> LOCATION: (19)..(246)
<223> OTHER INFORMATION: proBDNF
<220> FEATURE:
<221> NAME/KEY: MISC_FEATURE
<222> LOCATION: (128)..(246)
<223> OTHER INFORMATION: Mature peptide of BDNF

<400> SEQUENCE: 7

Met Thr Ile Leu Phe Leu Thr Met Val Ile Ser Tyr Phe Gly Cys Met
1               5                   10                  15

Lys Ala Ala Pro Met Lys Glu Ala Asn Ile Arg Gly Gln Gly Gly Leu
            20                  25                  30

Ala Tyr Pro Gly Val Arg Thr His Gly Thr Leu Glu Ser Val Asn Gly
        35                  40                  45

Pro Lys Ala Gly Ser Gly Leu Thr Ser Leu Ala Asp Thr Phe Glu His
    50                  55                  60

Val Ile Glu Glu Leu Leu Asp Glu Asp Gln Lys Val Arg Pro Asn Glu
65                  70                  75                  80

Glu Asn Asn Lys Asp Ala Asp Leu Tyr Thr Ser Arg Val Met Leu Ser
                85                  90                  95

Ser Gln Val Pro Leu Glu Pro Pro Leu Leu Phe Leu Leu Glu Glu Tyr
            100                 105                 110

Lys Asn Tyr Leu Asp Ala Ala Asn Met Ser Met Arg Val Arg Arg His
        115                 120                 125

Ser Asp Pro Ala Arg Arg Gly Glu Leu Ser Val Cys Asp Ser Ile Ser
    130                 135                 140

Glu Trp Val Thr Ala Ala Asp Lys Lys Thr Ala Val Asp Met Ser Gly
145                 150                 155                 160

Gly Thr Val Thr Val Leu Glu Lys Val Pro Val Ser Lys Gly Gln Leu
                165                 170                 175

Lys Gln Tyr Phe Tyr Glu Thr Lys Cys Asn Pro Met Gly Tyr Thr Lys
            180                 185                 190

Glu Gly Cys Arg Gly Ile Asp Lys Arg His Trp Asn Ser Gln Cys Arg
        195                 200                 205

Thr Thr Gln Ser Tyr Val Arg Ala Leu Thr Met Asp Ser Lys Lys Arg
    210                 215                 220

Ile Gly Trp Arg Phe Ile Arg Ile Asp Thr Ser Cys Val Cys Thr Leu
225                 230                 235                 240

Thr Ile Lys Arg Gly Arg
                245

<210> SEQ ID NO 8
<211> LENGTH: 257
<212> TYPE: PRT
<213> ORGANISM: Homo sapiens
<220> FEATURE:
<221> NAME/KEY: SIGNAL
<222> LOCATION: (1)..(16)
<223> OTHER INFORMATION: Signal peptide of NT3
<220> FEATURE:
<221> NAME/KEY: PROPEP
<222> LOCATION: (17)..(140)
<223> OTHER INFORMATION: Propeptide of NT3 (NT3pro)
<220> FEATURE:
<221> NAME/KEY: MISC_FEATURE
<222> LOCATION: (17)..(257)
<223> OTHER INFORMATION: proNT3
<220> FEATURE:
<221> NAME/KEY: MISC_FEATURE
<222> LOCATION: (141)..(257)
<223> OTHER INFORMATION: Mature peptide of NT3

-continued

```
<400> SEQUENCE: 8

Met Ser Ile Leu Phe Tyr Val Ile Phe Leu Ala Tyr Leu Arg Gly Ile
1               5                   10                  15

Gln Gly Asn Asn Met Asp Gln Arg Ser Leu Pro Glu Asp Ser Leu Asn
            20                  25                  30

Ser Leu Ile Ile Lys Leu Ile Gln Ala Asp Ile Leu Lys Asn Lys Leu
        35                  40                  45

Ser Lys Gln Met Val Asp Val Lys Glu Asn Tyr Gln Ser Thr Leu Pro
    50                  55                  60

Lys Ala Glu Ala Pro Arg Glu Pro Glu Arg Gly Gly Pro Ala Lys Ser
65                  70                  75                  80

Ala Phe Gln Pro Val Ile Ala Met Asp Thr Glu Leu Leu Arg Gln Gln
                85                  90                  95

Arg Arg Tyr Asn Ser Pro Arg Val Leu Leu Ser Asp Ser Thr Pro Leu
            100                 105                 110

Glu Pro Pro Pro Leu Tyr Leu Met Glu Asp Tyr Val Gly Ser Pro Val
        115                 120                 125

Val Ala Asn Arg Thr Ser Arg Arg Lys Arg Tyr Ala Glu His Lys Ser
    130                 135                 140

His Arg Gly Glu Tyr Ser Val Cys Asp Ser Glu Ser Leu Trp Val Thr
145                 150                 155                 160

Asp Lys Ser Ser Ala Ile Asp Ile Arg Gly His Gln Val Thr Val Leu
                165                 170                 175

Gly Glu Ile Lys Thr Gly Asn Ser Pro Val Lys Gln Tyr Phe Tyr Glu
            180                 185                 190

Thr Arg Cys Lys Glu Ala Arg Pro Val Lys Asn Gly Cys Arg Gly Ile
        195                 200                 205

Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr

<210> SEQ ID NO 9
<211> LENGTH: 210
<212> TYPE: PRT
<213> ORGANISM: Homo sapiens
<220> FEATURE:
<221> NAME/KEY: SIGNAL
<222> LOCATION: (1)..(24)
<223> OTHER INFORMATION: Signal peptide of NT4/5
<220> FEATURE:
<221> NAME/KEY: PROPEP
<222> LOCATION: (25)..(80)
<223> OTHER INFORMATION: Propeptide of NT4/5
<220> FEATURE:
<221> NAME/KEY: MISC_FEATURE
<222> LOCATION: (25)..(210)
<223> OTHER INFORMATION: proNT4/5
<220> FEATURE:
<221> NAME/KEY: MISC_FEATURE
<222> LOCATION: (81)..(210)
<223> OTHER INFORMATION: Mature peptide of NT4/5

<400> SEQUENCE: 9

Met Leu Pro Leu Pro Ser Cys Ser Leu Pro Ile Leu Leu Leu Phe Leu
1               5                   10                  15
```

```
Leu Pro Ser Val Pro Ile Glu Ser Gln Pro Pro Ser Thr Leu Pro
             20                  25                  30

Pro Phe Leu Ala Pro Glu Trp Asp Leu Leu Ser Pro Arg Val Val Leu
         35                  40                  45

Ser Arg Gly Ala Pro Ala Gly Pro Pro Leu Leu Phe Leu Leu Glu Ala
 50                  55                  60

Gly Ala Phe Arg Glu Ser Ala Gly Ala Pro Ala Asn Arg Ser Arg Arg
 65                  70                  75                  80

Gly Val Ser Glu Thr Ala Pro Ala Ser Arg Arg Gly Glu Leu Ala Val
                 85                  90                  95

Cys Asp Ala Val Ser Gly Trp Val Thr Asp Arg Thr Ala Val Asp
                100                 105                 110

Leu Arg Gly Arg Glu Val Glu Val Leu Gly Glu Val Pro Ala Ala Gly
                115                 120                 125

Gly Ser Pro Leu Arg Gln Tyr Phe Phe Glu Thr Arg Cys Lys Ala Asp
    130                 135                 140

Asn Ala Glu Glu Gly Pro Gly Ala Gly Gly Gly Cys Arg Gly
145                 150                 155                 160

Val Asp Arg Arg His Trp Val Ser Glu Cys Lys Ala Lys Gln Ser Tyr
                165                 170                 175

Val Arg Ala Leu Thr Ala Asp Ala Gln Gly Arg Val Gly Trp Arg Trp
            180                 185                 190

Ile Arg Ile Asp Thr Ala Cys Val Cys Thr Leu Leu Ser Arg Thr Gly
            195                 200                 205

Arg Ala
    210

<210> SEQ ID NO 10
<211> LENGTH: 13
<212> TYPE: PRT
<213> ORGANISM: Homo Sapiens
<220> FEATURE:
<221> NAME/KEY: MISC_FEATURE
<222> LOCATION: (1)..(13)
<223> OTHER INFORMATION: Neurotensin

<400> SEQUENCE: 10

Gln Leu Tyr Glu Asn Lys Pro Arg Arg Pro Tyr Ile Leu
1               5                   10

<210> SEQ ID NO 11
<211> LENGTH: 4
<212> TYPE: PRT
<213> ORGANISM: Homo Sapiens
<220> FEATURE:
<221> NAME/KEY: MISC_FEATURE
<222> LOCATION: (1)..(4)
<223> OTHER INFORMATION: Four C-terminal amino acids of Neurotensin

<400> SEQUENCE: 11

Pro Tyr Ile Leu
1

<210> SEQ ID NO 12
<211> LENGTH: 6
<212> TYPE: PRT
<213> ORGANISM: Artificial Sequence
<220> FEATURE:
<223> OTHER INFORMATION: Synthetically generated peptide
<220> FEATURE:
<221> NAME/KEY: VARIANT
<222> LOCATION: (1)..(1)
```

```
<223> OTHER INFORMATION: Xaa = N-methyl-Arg
<220> FEATURE:
<221> NAME/KEY: MISC_FEATURE
<222> LOCATION: (1)..(6)
<223> OTHER INFORMATION: NT69L
<220> FEATURE:
<221> NAME/KEY: VARIANT
<222> LOCATION: (4)..(4)
<223> OTHER INFORMATION: Xaa = L-neo-Trp
<220> FEATURE:
<221> NAME/KEY: VARIANT
<222> LOCATION: (5)..(5)
<223> OTHER INFORMATION: Xaa = tert-Leu

<400> SEQUENCE: 12

Xaa Lys Pro Xaa Xaa Leu
1               5

<210> SEQ ID NO 13
<211> LENGTH: 357
<212> TYPE: PRT
<213> ORGANISM: Homo Sapiens
<220> FEATURE:
<221> NAME/KEY: MISC_FEATURE
<222> LOCATION: (1)..(357)
<223> OTHER INFORMATION: RAP

<400> SEQUENCE: 13

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
                20                  25                  30

Gly Lys Tyr Ser Arg Glu Lys Asn Gln Pro Lys Pro Ser Pro Lys Arg
            35                  40                  45

Glu Ser Gly Glu Glu Phe Arg Met Glu Lys Leu Asn Gln Leu Trp Glu
        50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
225                 230                 235                 240

Val Ser His Gln Gly Tyr Ser Thr Glu Ala Glu Phe Glu Glu Pro Arg
                245                 250                 255
```

```
Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
            275                 280                 285

Glu Lys His Asn His Tyr Gln Lys Gln Leu Glu Ile Ala His Glu Lys
            290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
                340                 345                 350

Arg His Asn Glu Leu
                355

<210> SEQ ID NO 14
<211> LENGTH: 475
<212> TYPE: PRT
<213> ORGANISM: Homo sapiens
<220> FEATURE:
<221> NAME/KEY: MISC_FEATURE
<222> LOCATION: (1)..(475)
<223> OTHER INFORMATION: LPL

<400> SEQUENCE: 14

Met Glu Ser Lys Ala Leu Leu Val Leu Thr Leu Ala Val Trp Leu Gln
1               5                   10                  15

Ser Leu Thr Ala Ser Arg Gly Gly Val Ala Ala Ala Asp Gln Arg Arg
            20                  25                  30

Asp Phe Ile Asp Ile Glu Ser Lys Phe Ala Leu Arg Thr Pro Glu Asp
            35                  40                  45

Thr Ala Glu Asp Thr Cys His Leu Ile Pro Gly Val Ala Glu Ser Val
        50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110

Trp Leu Ser Arg Ala Gln Glu His Tyr Pro Val Ser Ala Gly Tyr Thr
            115                 120                 125

Lys Leu Val Gly Gln Asp Val Ala Arg Phe Ile Asn Trp Met Glu Glu
    130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
            195                 200                 205

Leu His Thr Phe Thr Arg Gly Ser Pro Gly Arg Ser Ile Gly Ile Gln
        210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
```

```
                  245                 250                 255
Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
            275                 280                 285

Tyr Arg Cys Ser Ser Lys Glu Ala Phe Glu Lys Gly Leu Cys Leu Ser
            290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
            355                 360                 365

Thr Val Ala Glu Ser Glu Asn Ile Pro Phe Thr Leu Pro Glu Val Ser
            370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
            435                 440                 445

Lys Val Ser His Leu Gln Lys Gly Lys Ala Pro Ala Val Phe Val Lys
            450                 455                 460

Cys His Asp Lys Ser Leu Asn Lys Lys Ser Gly
465                 470                 475

<210> SEQ ID NO 15
<211> LENGTH: 317
<212> TYPE: PRT
<213> ORGANISM: Homo sapiens
<220> FEATURE:
<221> NAME/KEY: MISC_FEATURE
<222> LOCATION: (1)..(317)
<223> OTHER INFORMATION: Apo E

<400> SEQUENCE: 15

Met Lys Val Leu Trp Ala Ala Leu Leu Val Thr Phe Leu Ala Gly Cys
1               5                   10                  15

Gln Ala Lys Val Glu Gln Ala Val Glu Thr Glu Pro Glu Pro Glu Leu
            20                  25                  30

Arg Gln Gln Thr Glu Trp Gln Ser Gly Gln Arg Trp Glu Leu Ala Leu
        35                  40                  45

Gly Arg Phe Trp Asp Tyr Leu Arg Trp Val Gln Thr Leu Ser Glu Gln
    50                  55                  60

Val Gln Glu Glu Leu Leu Ser Ser Gln Val Thr Gln Glu Leu Arg Ala
65                  70                  75                  80

Leu Met Asp Glu Thr Met Lys Glu Leu Lys Ala Tyr Lys Ser Glu Leu
                85                  90                  95

Glu Glu Gln Leu Thr Pro Val Ala Glu Glu Thr Arg Ala Arg Leu Ser
            100                 105                 110

Lys Glu Leu Gln Ala Ala Gln Ala Arg Leu Gly Ala Asp Met Glu Asp
        115                 120                 125
```

-continued

```
Val Cys Gly Arg Leu Val Gln Tyr Arg Gly Glu Val Gln Ala Met Leu
    130                 135                 140

Gly Gln Ser Thr Glu Glu Leu Arg Val Arg Leu Ala Ser His Leu Arg
145                 150                 155                 160

Lys Leu Arg Lys Arg Leu Leu Arg Asp Ala Asp Asp Leu Gln Lys Arg
                165                 170                 175

Leu Ala Val Tyr Gln Ala Gly Ala Arg Glu Gly Ala Glu Arg Gly Leu
            180                 185                 190

Ser Ala Ile Arg Glu Arg Leu Gly Pro Leu Val Glu Gln Gly Arg Val
            195                 200                 205

Arg Ala Ala Thr Val Gly Ser Leu Ala Gly Gln Pro Leu Gln Glu Arg
    210                 215                 220

Ala Gln Ala Trp Gly Glu Arg Leu Arg Ala Arg Met Glu Glu Met Gly
225                 230                 235                 240

Ser Arg Thr Arg Asp Arg Leu Asp Glu Val Lys Glu Gln Val Ala Glu
                245                 250                 255

Val Arg Ala Lys Leu Glu Glu Gln Ala Gln Gln Ile Arg Leu Gln Ala
                260                 265                 270

Glu Ala Phe Gln Ala Arg Leu Lys Ser Trp Phe Glu Pro Leu Val Glu
            275                 280                 285

Asp Met Gln Arg Gln Trp Ala Gly Leu Val Glu Lys Val Gln Ala Ala
            290                 295                 300

Val Gly Thr Ser Ala Ala Pro Val Pro Ser Asp Asn His
305                 310                 315
```